(12) United States Patent
Praetorius et al.

(10) Patent No.: US 11,913,050 B2
(45) Date of Patent: Feb. 27, 2024

(54) SCALABLE BIOTECHNOLOGICAL PRODUCTION OF DNA SINGLE STRAND MOLECULES OF DEFINED SEQUENCE AND LENGTH

(71) Applicant: TECHNISCHE UNIVERSITÄT MÜNCHEN, Munich (DE)

(72) Inventors: Florian Praetorius, Munich (DE); Hendrik Dietz, Haar (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 471 days.

(21) Appl. No.: 16/329,495

(22) PCT Filed: Jul. 17, 2017

(86) PCT No.: PCT/EP2017/068051
§ 371 (c)(1),
(2) Date: Feb. 28, 2019

(87) PCT Pub. No.: WO2018/054571
PCT Pub. Date: Mar. 29, 2018

(65) Prior Publication Data
US 2019/0203242 A1    Jul. 4, 2019

(30) Foreign Application Priority Data
Sep. 21, 2016    (EP) .................................. 16189976

(51) Int. Cl.
| | |
|---|---|
| C12P 19/34 | (2006.01) |
| C12N 15/10 | (2006.01) |
| C12N 15/73 | (2006.01) |
| C12Q 1/6876 | (2018.01) |

(52) U.S. Cl.
CPC .............. *C12P 19/34* (2013.01); *C12N 15/10* (2013.01); *C12N 15/73* (2013.01); *C12Q 1/6876* (2013.01); *C12N 2795/14042* (2013.01)

(58) Field of Classification Search
None
See application file for complete search history.

(56) References Cited

FOREIGN PATENT DOCUMENTS

CN        103276074 A        9/2013

OTHER PUBLICATIONS

Jupin et al., "Abundant, easy and reproducible production of single-stranded DNA from phagemids using helper phage-infected competent cells" 23(3) Nucleic Acids Research 535-536 (Year: 1995).*
Dahlgren et al., "Development of Scale-Down Techniques for Investigation of Recombinant *Escherichia coli* Fermentations: Acid Metabolites in Shake Flasks and Stirred Bioreactors" 9 Biotechnology Progress 580-586 (Year: 1993).*
Qi et al., "Phagemid Vectors for Phage Display: Properties Characteristics and Construction" 417 Journal of Molecular Biology 129-143 (Year: 2012).*
Ducani, C., et al., "Enzymatic Production of Monoclonal Stoichiometric Single-Stranded DNA Oligonucleotides." Nat Methods, Jul. 2013, 10(7): 1-20, doi:10.1038/nmeth.2503.
Gu, H., et al., "Production of single-stranded DNAs by self-cleavage of rolling-circle amplification products." BioTechniques, Jun. 2013, 54(6): 337-343.
Kick, Benjamin, et al., "Efficient Production of Single-Stranded Phage DNA as Scaffolds for DNA Origami." NANO Letters, 2015, 15: 4672-4676.
Marchi, A.N., et al., "Toward Larger DNA Origami." NANO Letters, 2014, 14: 5740-5747.
Schmidt, T.L., et al., "Scalable amplification of strand subsets from chip-synthesized oligonucleotide libraries." Nature Communications, 2015, 6(8634): 1-7.
Stahl, E., et al., "Facile and Scalable Preparation of Pure and Dense DNA Origami Solutions." Angew. Chem. Int. Ed., 2014, 53: 12735-12740.
Office Action issued by the Japanese Patent Office in parallel Japanese Patent Application 2019-515435.

* cited by examiner

*Primary Examiner* — Nancy J Leith
(74) *Attorney, Agent, or Firm* — SALIWANCHIK, LLOYD & EISENSCHENK

(57) ABSTRACT

IN The present invention relates to a method for the recombinant production of DNA single stranded molecules, comprising the steps of (1) providing a pseudogene nucleic acid; (2) integrating the pseudogene nucleic acid into a vector, transforming bacterial cells with said vector and producing a precursor ssDNA from said vector under bacterial culture conditions; (3) isolating the precursor ssDNA from the bacterial culture; (4) digesting the precursor ss DNA under reaction conditions where self-cleaving DNA sequences become active; and (5) separating and obtaining the target single stranded DNA oligo- or polynucleotide(s). The method of the present invention is suitable for the mass production of DNA single stranded molecules. The present invention further relates to the use of the target single stranded DNA oligo- or polynucleotide(s), in particular in DNA nanotechnology, or as research tools.

16 Claims, 9 Drawing Sheets
Specification includes a Sequence Listing.

SEQUENCE LISTING

```
<160> NUMBER OF SEQ ID NOS: 35

<210> SEQ ID NO 1
<211> LENGTH: 12
<212> TYPE: DNA
<213> ORGANISM: Artificial Sequence
<220> FEATURE:
<223> OTHER INFORMATION: DNAzyme

<400> SEQUENCE: 1
tagttgagct gt                                                            12

<210> SEQ ID NO 2
<211> LENGTH: 9
<212> TYPE: DNA
<213> ORGANISM: Artificial Sequence
<220> FEATURE:
<223> OTHER INFORMATION: DNAzyme

<400> SEQUENCE: 2 acgttgaag                                                                 9

<210> SEQ ID NO 3
<211> LENGTH: 105
<212> TYPE: DNA
<213> ORGANISM: Artificial Sequence
<220> FEATURE:
<223> OTHER INFORMATION: Oligonucleotide

<400> SEQUENCE: 3
tactcttaga agtgtcccaa ctacactaga aggacagtgg cgagaggatt acgcgcctag        60
atcaacttta atgttgactc gtgcacccaa catgcttttt agctc                        105

<210> SEQ ID NO 4
<211> LENGTH: 105
<212> TYPE: DNA
<213> ORGANISM: Artificial Sequence
<220> FEATURE:
<223> OTHER INFORMATION: Oligonucleotide

<400> SEQUENCE: 4
gcacattgag ggctgctatt aagacacgac ttatcccttt ctcaaaaggc cagcaaagcg        60
atctggcccc aatagggaa caagaggcag aacatatcaa agcga                        105
```

<210> SEQ ID NO 5
<211> LENGTH: 105
<212> TYPE: DNA
<213> ORGANISM: Artificial Sequence
<220> FEATURE:
<223> OTHER INFORMATION: Oligonucleotide

<400> SEQUENCE: 5
cttaccgaga atagacaccc gccttacagc gaggcgaagg gctttaaatc aatctagagc    60
atcataccag gcgtttcgtt cttggcgccg caaccacctg tatgc                  105

<210> SEQ ID NO 6
<211> LENGTH: 105
<212> TYPE: DNA
<213> ORGANISM: Artificial Sequence
<220> FEATURE:
<223> OTHER INFORMATION: Oligonucleotide

<400> SEQUENCE: 6
tagaccgcga aaatgacgg ggaaagcctg gcgaataact acgttgcctg actcccgggg     60
atattctcat agctcactaa ctattgtgct gtagagctcc gtcta                  105

<210> SEQ ID NO 7
<211> LENGTH: 105
<212> TYPE: DNA
<213> ORGANISM: Artificial Sequence
<220> FEATURE:
<223> OTHER INFORMATION: Oligonucleotide

<400> SEQUENCE: 7
ggcgaccaaa ctctcagggt tattgtctga tttatcgcgt ccggcggtgc tacagacccc    60
tggtccgccc ccctgacaag tataaaacca gcatttatca aggat                  105

<210> SEQ ID NO 8
<211> LENGTH: 105
<212> TYPE: DNA
<213> ORGANISM: Artificial Sequence
<220> FEATURE:
<223> OTHER INFORMATION: Oligonucleotide

<400> SEQUENCE: 8
tcagggcata atcgcgtta atattttgcg cggggattaa gttgcgcctt atccgggctg     60
tagtatccac agaatcacgc gtatgtttgt cattgtaaaa agaa                   105

<210> SEQ ID NO 9
<211> LENGTH: 105
<212> TYPE: DNA
<213> ORGANISM: Artificial Sequence
<220> FEATURE:
<223> OTHER INFORMATION: Oligonucleotide

<400> SEQUENCE: 9
cttcggtgtt tggtccatcc aaaaaggatc ttcacagaaa aatgtttgca agcagcagta    60
tttcattcag aaagcggtct gtgactggtg ataacccaat actca                  105

<210> SEQ ID NO 10
<211> LENGTH: 105
<212> TYPE: DNA
<213> ORGANISM: Artificial Sequence
<220> FEATURE:
<223> OTHER INFORMATION: Oligonucleotide

<400> SEQUENCE: 10
aaggagcggg aaggcaatga tgaggcacct atctcaaggc cacggatacc tgtccggcca    60
ctggtgcggg agggaagcac tattaaagaa ccagtttggt tccgc    105

<210> SEQ ID NO 11
<211> LENGTH: 112
<212> TYPE: DNA
<213> ORGANISM: Artificial Sequence
<220> FEATURE:
<223> OTHER INFORMATION: Oligonucleotide

<400> SEQUENCE: 11
ctacaggaag ttggctgcat aattctcttt caccaaatgc cgcaaaaaaa attgttgtgt    60
cacccagtta ccttcggaaa ccactgatct tttctacgtt aagggagcta ga    112

<210> SEQ ID NO 12
<211> LENGTH: 91
<212> TYPE: DNA
<213> ORGANISM: Artificial Sequence
<220> FEATURE:
<223> OTHER INFORMATION: Oligonucleotide

<400> SEQUENCE: 12
agaggcgtgg gcgctcttcc gatacggtgt atctcagttc ggcgaccgct gggtaaccct    60
aaacactacg tgaaccaccg aaattcgcgt t    91

<210> SEQ ID NO 13
<211> LENGTH: 105
<212> TYPE: DNA
<213> ORGANISM: Artificial Sequence
<220> FEATURE:
<223> OTHER INFORMATION: Oligonucleotide

<400> SEQUENCE: 13
tcatgaggat ccttcgctgg tagcggtggc tgaaggctcg tccctccgaa tgccatccgt    60
aagtgatctt agggcgacac ggaatccgcc tatggcttgg tatct    105

<210> SEQ ID NO 14
<211> LENGTH: 105
<212> TYPE: DNA
<213> ORGANISM: Artificial Sequence
<220> FEATURE:
<223> OTHER INFORMATION: Oligonucleotide

<400> SEQUENCE: 14
aaacttgcat aggcaagctc cctcgtgcgt atgtacattc gctgtagcgt cttgcccggc    60
gtcggaaaac ggatacatat ttgagaccca cgctgcgcat tagca    105

<210> SEQ ID NO 15
<211> LENGTH: 105
<212> TYPE: DNA
<213> ORGANISM: Artificial Sequence
<220> FEATURE:
<223> OTHER INFORMATION: Oligonucleotide

<400> SEQUENCE: 15
ttcgttcatg tgagcccttc gggaagcgcc cggtacgcca gcggcgaacc caacgtcaaa    60
gggagatagg aaagtgccac ctaagtgtag aaggggacg tcttg    105

<210> SEQ ID NO 16
<211> LENGTH: 105
<212> TYPE: DNA
<213> ORGANISM: Artificial Sequence

```
<220> FEATURE:
<223> OTHER INFORMATION: Oligonucleotide

<400> SEQUENCE: 16
tcgacgcatg aagtcgagcg ccctttttga tccagttcga tggtactcac catgttgtgc    60
aaactccggt gtcctgcctt ttaaattaaa atcaagtcaa acccg                   105

<210> SEQ ID NO 17
<211> LENGTH: 105
<212> TYPE: DNA
<213> ORGANISM: Artificial Sequence
<220> FEATURE:
<223> OTHER INFORMATION: Oligonucleotide

<400> SEQUENCE: 17
taaaaagaat cagtaccgcg tatgtattaa gtgctcatca ttaatacgga gggcgctggc    60
aagcattcag gctcaccagt taccaatgct tgccgcgttg ttccg                   105

<210> SEQ ID NO 18
<211> LENGTH: 105
<212> TYPE: DNA
<213> ORGANISM: Artificial Sequence
<220> FEATURE:
<223> OTHER INFORMATION: Oligonucleotide

<400> SEQUENCE: 18
acaggaccta cggcgatcaa gtgatcccac caagtcattc tgctgttgac aatattattg    60
aagccagccg gcttaataag tggtggccta atataaagac aaaaa                   105

<210> SEQ ID NO 19
<211> LENGTH: 105
<212> TYPE: DNA
<213> ORGANISM: Artificial Sequence
<220> FEATURE:
<223> OTHER INFORMATION: Oligonucleotide

<400> SEQUENCE: 19
accctgctaa caggaactgt tgggcgctga taataccgcg ccactttaat agaaaaataa    60
acaagtgctg gcgatcggca gcagccactg gcgcttacgg aaccg                   105

<210> SEQ ID NO 20
<211> LENGTH: 105
<212> TYPE: DNA
<213> ORGANISM: Artificial Sequence
<220> FEATURE:
<223> OTHER INFORMATION: Oligonucleotide

<400> SEQUENCE: 20
gcgctctgtt ttttaaggat ctcaagaaat tatcagtcta ttgggaatac agcatctttt    60
acttactgtc tcgttgtcag aagtcatcgt ggccgggaat tttgg                   105

<210> SEQ ID NO 21
<211> LENGTH: 105
<212> TYPE: DNA
<213> ORGANISM: Artificial Sequence
<220> FEATURE:
<223> OTHER INFORMATION: Oligonucleotide

<400> SEQUENCE: 21
gagcgaggct ctcctgctgg cgttttttcgt ctgacggctc cacatgagcg ttcttcgggg    60
cgagagttgc gtcacgctgc gcgttacagg gcagcaatta tgagt                   105
```

```
<210> SEQ ID NO 22
<211> LENGTH: 105
<212> TYPE: DNA
<213> ORGANISM: Artificial Sequence
<220> FEATURE:
<223> OTHER INFORMATION: Oligonucleotide

<400> SEQUENCE: 22
agtccaatgg cgctacgcag gaaagaacat ccatagatac ggtccccgag ttgagtgttg    60
ttcgtggact gtggcgagaa aggacctctt ctaccatctg tctat                   105

<210> SEQ ID NO 23
<211> LENGTH: 91
<212> TYPE: DNA
<213> ORGANISM: Artificial Sequence
<220> FEATURE:
<223> OTHER INFORMATION: Oligonucleotide

<400> SEQUENCE: 23
ttcagcctgt aggtactcaa aggcggtact tcctcgccaa cgttaaaatc ggcaaaatcc    60
cttgatggcc gggagccccc gattcaaggc g                                  91

<210> SEQ ID NO 24
<211> LENGTH: 2630
<212> TYPE: DNA
<213> ORGANISM: Artificial Sequence
<220> FEATURE:
<223> OTHER INFORMATION: Phagemid backbone that serves as scaffold

<400> SEQUENCE: 24
gttgtcgtct ctgaagatgt gagctacaac gtcgtgactg ggaaaaccct ggcgttaccc    60
aacttaatcg ccttgcagca catccccctt tcgccagctg gcgtaatagc gaagaggccc   120
gcaccgatcg cccttcccaa cagttgcgca gcctgaatgg cgaatgggac gcgccctgta   180
gcggcgcatt aagcgcggcg ggtgtggtgg ttacgcgcag cgtgaccgct acacttgcca   240
gcgccctagc gcccgctcct ttcgctttct tcccttcctt tctcgccacg ttcgccggct   300
ttccccgtca gctctaaat cgggggctcc ctttagggtt ccgatttagt gctttacggc   360
acctcgaccc caaaaaactt gattagggtg atggttcacg tagtgggcca tcgccctgat   420
agacggtttt tcgccctttg acgttggagt ccacgttctt taatagtgga ctcttgttcc   480
aaactggaac aacactcaac cctatctcgg tctattcttt tgatttataa gggattttgc   540
cgatttcggc ctattggtta aaaaatgagc tgatttaaca aaaatttaac gcgaatttta   600
acaaaatatt aacgcttaca atttaggtgg cacttttcgg ggaaatgtgc gcggaacccc   660
tatttgttta tttttctaaa tacattcaaa tatgtatccg ctcatgagac aataaccctg   720
ataaatgctt caataatatt gaaaaaggaa gagtatgagt attcaacatt tccgtgtcgc   780
ccttattccc ttttttgcgg cattttgcct tcctgttttt gctcacccag aaacgctggt   840
gaaagtaaaa gatgctgaag atcagttggg tgcacgagtg ggttacatcg aactggatct   900
caacagcggt aagatccttg agagttttcg ccccgaagaa cgttttccaa tgatgagcac   960
ttttaaagtt ctgctatgtg gcgcggtatt atcccgtatt gacgccgggc aagagcaact  1020
cggtcgccgc atacactatt ctcagaatga cttggttgag tactcaccag tcacagaaaa  1080
gcatcttacg gatggcatga cagtaagaga attatgcagt gctgccataa ccatgagtga  1140
taacactgcg gccaacttac ttctgacaac gatcggagga ccgaaggagc taaccgcttt  1200
tttgcacaac atgggggatc atgtaactcg ccttgatcgt tgggaaccgg agctgaatga  1260
```

```
agccatacca aacgacgagc gtgacaccac gatgcctgta gcaatggcaa caacgttgcg    1320
caaactatta actggcgaac tacttactct agcttcccgg caacaattaa tagactggat    1380
ggaggcggat aaagttgcag gaccacttct gcgctcggcc cttccggctg ctggtttat     1440 tgctgataaa tctggagccg gtgagcgtgg gtcacgcggt atcattgcag cactggggcc    1500
agatggtaag ccctcccgta tcgtagttat ctacacgacg gggagtcagg caactatgga    1560
tgaacgaaat agacagatcg ctgagatagg tgcctcactg attaagcatt ggtaactgtc    1620
agaccaagtt tactcatata ctttagat tgatttaaaa cttcattttt aatttaaaag      1680
gatctaggtg aagatccttt ttgataatct catgaccaaa atcccttaac gtgagttttc    1740
gttccactga gcgtcagacc ccgtagaaaa gatcaaagga tcttcttgag atcctttttt    1800
tctgcgcgta atctgctgct tgcaaacaaa aaaaccaccg ctaccagcgg tggtttgttt    1860
gccggatcaa gagctaccaa ctcttttttcc gaaggtaact ggcttcagca gagcgcagat    1920
accaaatact gtccttctag tgtagccgta gttaggccac cacttcaaga actctgtagc    1980
accgcctaca tacctcgctc tgctaatcct gttaccagtg gctgctgcca gtggcgataa    2040
gtcgtgtctt accgggttgg actcaagacg atagttaccg gataaggcgc agcggtcggg    2100
ctgaacgggg ggttcgtgca cacagcccag cttggagcga acgacctaca ccgaactgag    2160
atacctacag cgtgagctat gagaaagcgc cacgcttccc gaagggagaa aggcggacag    2220
gtatccggta agcggcaggg tcggaacagg agagcgcacg agggagcttc caggggga aa   2280 cgcctggtat ctttatagtc ctgtcgggtt tcgccacctc tgacttgagc gtcgattttt    2340
gtgatgctcg tcaggggggc ggagcctatg gaaaaacgcc agcaacgcgg cctttttacg    2400
gttcctggcc ttttgctggc cttttgctca catgttcttt cctgcgttat cccctgattc    2460
tgtggataac cgtattaccg cctttgagtg agctgatacc gctcgccgca gccgaacgac    2520
cgagcgcagc gagtcagtga gcgaggaagc ggaagagcgc ccaatacgca aaccgcctct    2580
ccccgcgcgt tggccgattc attaacttaa ttgcagcaag agacgcttct                2630
```

<210> SEQ ID NO 25
<211> LENGTH: 6813
<212> TYPE: DNA
<213> ORGANISM: Artificial Sequence
<220> FEATURE:
<223> OTHER INFORMATION: Full phagemid ssDNA sequence

<400> SEQUENCE: 25

```
ttttccaatg atgagcactt ttaaagttct gctatgtggc gcggtattat cccgtattga      60
cgccgggcaa gagcaactcg gtcgccgcat acactattct cagaatgact tggttgagta    120
ctcaccagtc acagaaaagc atcttacgga tggcatgaca gtaagagaat tatgcagtgc    180
tgccataacc atgagtgata acactgcggc caacttactt ctgacaacga tcggaggacc    240
gaaggagcta accgcttttt tgcacaacat ggggatcat gtaactcgcc ttgatcgttg      300
ggaaccggag ctgaatgaag ccataccaaa cgacgagcgt gacaccacga tgcctgtagc    360
aatggcaaca acgttgcgca aactattaac tggcgaacta cttactctag cttcccggca    420
acaattaata gactggatgg aggcggataa agttgcagga ccacttctgc gctcggccct    480
tccggctggc tggtttattg ctgataaatc tggagccggt gagcgtgggt ctcgcggtat    540
cattgcagca ctggggccag atggtaagcc ctcccgtatc gtagttatct acacgacggg    600
gagtcaggca actatggatg aacgaaatag acagatcgct gagataggtg cctcactgat    660
```

```
taagcattgg taactgtcag accaagttta ctcatatata ctttagattg atttaaaact    720
tcatttttaa tttaaaagga tctaggtgaa gatccttttt gataatctca tgaccaaaat    780
cccttaacgt gagttttcgt tccactgagc gtcagacccc gtagaaaaga tcaaaggatc    840
ttcttgagat cctttttttc tgcgcgtaat ctgctgcttg caaacaaaaa aaccaccgct    900
accagcggtg gtttgtttgc cggatcaaga gctaccaact cttttccga aggtaactgg     960
cttcagcaga gcgcagatac caaatactgt ccttctagtg tagccgtagt taggccacca   1020
cttcaagaac tctgtagcac cgcctacata cctcgctctg ctaatcctgt taccagtggc   1080
tgctgccagt ggcgataagt cgtgtcttac cgggttggac tcaagacgat agttaccgga   1140
taaggcgcag cggtcgggct gaacggggggg ttcgtgcaca cagcccagct tggagcgaac  1200
gacctacacc gaactgagat acctacagcg tgagctatga gaaagcgcca cgcttcccga   1260
agggagaaag gcggacaggt atccggtaag cggcagggtc ggaacaggag agcgcacgag   1320
ggagcttcca gggggaaacg cctggtatct ttatagtcct gtcgggtttc gccacctctg   1380
acttgagcgt cgatttttgt gatgctcgtc aggggggcgg agcctatgga aaaacgccag   1440
caacgcggcc ttttacggt tcctggcctt ttgctggcct tttgctcaca tgttctttcc    1500
tgcgttatcc cctgattctg tggataaccg tattaccgcc tttgagtgag ctgataccgc   1560
tcgccgcagc cgaacgaccg agcgcagcga gtcagtgagc gaggaagcgg aagagcgccc   1620
aatacgcaaa ccgcctctcc ccgcgcgttg gccgattcat taacttaatt gcacgttgaa   1680
gcgttacctg ttaggtaacg tagttgagct gtgcaattaa ttttttaaga gtatagttga   1740
gctgtcacag aatgtgacgt tgaagtactc ttagaagtgt cccaactaca ctagaaggac   1800
agtggcgaga ggattacgcg cctagatcaa ctttaatgtt gactcgtgca cccaacatgc   1860
tttttagctc acgttgaagc gttacctgtt aggtaacgta gttgagctgt gagctaaatt   1920
ttttcaatgt gtagttgagc tgtcacagaa tgtgacgttg aagcacattg agggctgcta   1980
ttaagacacg acttatccct ttctcaaaag gccagcaaag cgatctggcc ccaatagggg   2040
aacaagaggc agaacatatc aaagcgacgt tgaagcgtta cctgttaggt aacgtagttg   2100
agctgtcgct ttgatttttt cggtaagtag ttgagctgtc acagaatgtg acgttgaagc   2160
ttaccgagaa tagacacccg ccttacagcg aggcgaaggg ctttaaatca atctagagca   2220
tcataccagg cgtttcgttc ttggcgccgc aaccacctgt atgcacgttg aagcgttacc   2280
tgttaggtaa cgtagttgag ctgtgcatac agttcctgcg gtctatagtt gagctgtcac   2340
agaatgtgac gttgaagtag accgcgaaaa atgacgggga aagcctggcg aataactacg   2400
ttgcctgact cccggggata ttctcatagc tcactaacta ttgtgctgta gagctccgtc   2460
tacgttgaag cgttacctgt taggtaacgt agttgagctg tagacggagt ttttttggtc   2520
gctagttgag ctgtcacaga atgtgacgtt gaaggcgacc aaactctcag ggttattgtc   2580
tgatttatcg cgtccggcgg tgctacagac ccctggtccg ccccccctgac aagtataaaa  2640
ccagcattta tcaaggatac gttgaagcgt tacctgttag gtaacgtagt tgagctgtat   2700
ccttgatttt ttgccctgat agttgagctg tcacagaatg tgacgttgaa gtcagggcat   2760
aaatcgcgtt aatattttgc gcggggatta agttgcgcct tatccgggct gtagtatcca   2820
cagaatcacg cgtatgtttg tcattgtaaa aaagaacgtt gaagcgttac ctgttaggta   2880
acgtagttga gctgttcttt ttttttttca ccgaagtagt tgagctgtca cagaatgtga   2940
cgttgaagct tcggtgtttg gtccatccaa aaaggatctt cacagaaaaa tgtttgcaag   3000
cagcagtatt tcattcagaa agcggtctgt gactggtgat aacccaatac tcacgttgaa   3060
```

```
gcgttacctg ttaggtaacg tagttgagct gtgagtattg tttttcgctc ctttagttga    3120
gctgtcacag aatgtgacgt tgaagaagga gcgggaaggc aatgatgagg cacctatctc    3180
aaggccacgg atacctgtcc ggccactggt gcgggaggga agcactatta aagaaccagt    3240
ttggttccgc acgttgaagc gttacctgtt aggtaacgta gttgagctgt gcggaacctt    3300
ttttcctgta gtagttgagc tgtcacagaa tgtgacgttg aagctacagg aagttggctg    3360
cataattctc tttcaccaaa tgccgcaaaa aaaattgttg tgtcacccag ttaccttcgg    3420
aaaccactga tcttttctac gttaagggag ctagacgttg aagcgttacc tgttaggtaa    3480
cgtagttgag ctgtctagct cctttttcca cgccttagtt gagctgtcac agaatgtgac    3540
gttgaagagg cgtgggcgct cttccgatac ggtgtatctc agttcggcga ccgctgggta    3600
accctaaaca ctacgtgaac caccgaaatt cgcgttacgt gaagcgtta  cctgttaggt    3660 aacgtagttg agctgtaacg cgaaccttc  ctcatgatag ttgagctgtc acagaatgtg    3720
acgttgaagt catgaggatc cttcgctggt agcggtggct gaaggctcgt ccctccgaat    3780
gccatccgta agtgatctta gggcgacacg gaatccgcct atggcttggt atctacgttg    3840
aagcgttacc tgttaggtaa cgtagttgag ctgtagatac cattttttgca agttttagtt    3900 gagctgtcac agaatgtgac gttgaagaaa cttgcatagg caagctccct cgtgcgtatg    3960
tacattcgct gtagcgtctt gcccggcgtc ggaaaacgga tacatatttg agacccacgc    4020
tgcgcattag cacgttgaag cgttacctgt taggtaacgt agttgagctg tgctaatgct    4080
tttttgaacg aatagttgag ctgtcacaga atgtgacgtt gaagttcgtt catgtgagcc    4140
cttcgggaag cgcccggtac gccagcggcg aacccaacgt caaagggaga taggaaagtg    4200
ccacctaagt gtagaagggg gacgtcttga cgttgaagcg ttacctgtta ggtaacgtag    4260
ttgagctgtc aagacgtttt tttgcgtcga tagttgagct gtcacagaat gtgacgttga    4320
agtcgacgca tgaagtcgag cgcccttttt gatccagttc gatggtactc accatgttgt    4380
gcaaactccg gtgtcctgcc ttttaaatta aaatcaagtc aaacccgacg ttgaagcgtt    4440
acctgttagg taacgtagtt gagctgtcgg gtttgttttt tctttttata gttgagctgt    4500
cacagaatgt gacgttgaag taaaaagaat cagtaccgcg tatgtattaa gtgctcatca    4560
ttaatacgga gggcgctggc aagcattcag gctcaccagt taccaatgct tgccgcgttg    4620
ttccgacgtt gaagcgttac ctgttaggta acgtagttga gctgtcggaa caattttggg    4680
tcctgttagt tgagctgtca cagaatgtga cgttgaagac aggacctacg gcgatcaagt    4740
gatcccacca agtcattctg ctgttgacaa tattattgaa gccagccggc ttaataagtg    4800
gtggcctaat ataaagacaa aaacgttgaa gcgttacctg ttaggtaacg tagttgagct    4860 gttttgtct cctcagcag ggttagttga gctgtcacag aatgtgacgt tgaagaccct    4920
gctaacagga actgttgggc gctgataata ccgcgccact ttaatagaaa ataaacaag    4980 tgctggcgat cggcagcagc cactggcgct tacggaaccg acgttgaagc gttacctgtt    5040
aggtaacgta gttgagctgt cggttccgtt tttacagagc gtagttgagc tgtcacagaa    5100
tgtgacgttg aagcgctctg ttttttaagg atctcaagaa attatcagtc tattgggaat    5160
acagcatctt ttacttactg tctcgttgtc agaagtcatc gtggccggga atttggacg    5220 ttgaagcgtt acctgttagg taacgtagtt gagctgtcca aaatttttt gcctcgctta    5280 gttgagctgt cacagaatgt gacgttgaag agcgaggctc tcctgctggc gttttcgtc    5340 tgacggctcc acatgagcgt tcttcggggc gagagttgcg tcacgctgcg cgttacaggg    5400
```

```
cagcaattat gagtacgttg aagcgttacc tgttaggtaa cgtagttgag ctgtactcat    5460
aacctttcca ttggatagtt gagctgtcac agaatgtgac gttgaagtcc aatggcgcta    5520
cgcaggaaag aacatccata gatacggtcc ccgagttgag tgttgttcgt ggactgtggc    5580
gagaaaggac ctcttctacc atctgtctat acgttgaagc gttacctgtt aggtaacgta    5640
gttgagctgt atagacagtt tttaggctga atagttgagc tgtcacagaa tgtgacgttg    5700
aagttcagcc tgtaggtact caaaggcggt acttcctcgc caacgttaaa atcggcaaaa    5760
tcccttgatg gccgggagcc cccgattcaa ggcgacgttg aagcgttacc tgttaggtaa    5820
cgtagttgag ctgtcgcctt gattttgct cacattagtt gagctgtcac agaatgtgac    5880
gttgaagatg tgagctacaa cgtcgtgact gggaaaaccc tggcgttacc caacttaatc    5940
gccttgcagc acatccccct ttcgccagct ggcgtaatag cgaagaggcc cgcaccgatc    6000
gcccttccca acagttgcgc agcctgaatg gcgaatggga cgcgccctgt agcggcgcat    6060
taagcgcggc gggtgtggtg gttacgcgca gcgtgaccgc tacacttgcc agcgccctag    6120
cgcccgctcc tttcgctttc ttcccttcct ttctcgccac gttcgccggc tttccccgtc    6180
aagctctaaa tcggggggctc cctttagggt tccgatttag tgctttacgg cacctcgacc    6240
ccaaaaaact tgattagggt gatggttcac gtagtgggcc atcgccctga tagacggttt    6300
ttcgcccttt gacgttggag tccacgttct ttaatagtgg actcttgttc caaactggaa    6360
caacactcaa ccctatctcg gtctattctt ttgatttata agggattttg ccgatttcgg    6420
cctattggtt aaaaaatgag ctgatttaac aaaaatttaa cgcgaatttt aacaaaatat    6480
taacgcttac aatttaggtg cacttttcg gggaaatgtg cgcggaaccc ctatttgttt    6540 attttctaa atacattcaa atatgtatcc gctcatgaga caataaccct gataaatgct    6600
tcaataatat tgaaaagga agagtatgag tattcaacat ttccgtgtcg cccttattcc    6660
cttttttgcg cattttgcc ttcctgtttt tgctcaccca gaaacgctgg tgaaagtaaa    6720
agatgctgaa gatcagttgg gtgcacgagt gggttacatc gaactggatc tcaacagcgg    6780
taagatcctt gagagttttc gccccgaaga acg                                 6813

<210> SEQ ID NO 26
<211> LENGTH: 58
<212> TYPE: DNA
<213> ORGANISM: Artificial Sequence
<220> FEATURE:
<223> OTHER INFORMATION: DNAzyme oligonucleotide

<400> SEQUENCE: 26 tttttttgccc tgatagttga gctgtcacag aatgtgacgt tgaagtcagg gcataaat    58

<210> SEQ ID NO 27
<211> LENGTH: 58
<212> TYPE: DNA
<213> ORGANISM: Artificial Sequence
<220> FEATURE:
<223> OTHER INFORMATION: DNAzyme oligonucleotide

<400> SEQUENCE: 27 tttttttgccc tgatagttga gctatcacag aatgtgatgt tgaagtcagg gcataaat    58

<210> SEQ ID NO 28
<211> LENGTH: 6813
<212> TYPE: DNA
<213> ORGANISM: Artificial Sequence
<220> FEATURE:
<223> OTHER INFORMATION: Phagemid
```

<400> SEQUENCE: 28

```
ttttccaatg atgagcactt ttaaagttct gctatgtggc gcggtattat cccgtattga      60
cgccgggcaa gagcaactcg gtcgccgcat acactattct cagaatgact tggttgagta     120
ctcaccagtc acagaaaagc atcttacgga tggcatgaca gtaagagaat tatgcagtgc     180
tgccataacc atgagtgata acactgcggc caacttactt ctgacaacga tcggaggacc     240
gaaggagcta accgcttttt tgcacaacat gggggatcat gtaactcgcc ttgatcgttg     300
ggaaccggag ctgaatgaag ccataccaaa cgacgagcgt gacaccacga tgcctgtagc     360
aatggcaaca acgttgcgca aactattaac tggcgaacta cttactctag cttcccggca     420
acaattaata gactggatgg aggcggataa agttgcagga ccacttctgc gctcggccct     480
tccggctggc tggtttattg ctgataaatc tggagccggt gagcgtgggt ctcgcggtat     540
cattgcagca ctggggccag atggtaagcc ctcccgtatc gtagttatct acacgacggg     600
gagtcaggca actatggatg aacgaaatag acagatcgct gagataggtg cctcactgat     660
taagcattgg taactgtcag accaagttta ctcatatata ctttagattg atttaaaact     720
tcattttaa tttaaaagga tctaggtgaa gatcctttt gataatctca tgaccaaaat     780
cccttaacgt gagttttcgt tccactgagc gtcagacccc gtagaaaaga tcaaaggatc     840
ttcttgagat cctttttttc tgcgcgtaat ctgctgcttg caaacaaaaa aaccaccgct     900
accagcggtg gtttgtttgc cggatcaaga gctaccaact cttttccga aggtaactgg     960
cttcagcaga gcgcagatac caaatactgt ccttctagtg tagccgtagt taggccacca    1020
cttcaagaac tctgtagcac cgcctacata cctcgctctg ctaatcctgt taccagtggc    1080
tgctgccagt ggcgataagt cgtgtcttac cgggttggac tcaagacgat agttaccgga    1140
taaggcgcag cggtcgggct gaacggggg ttcgtgcaca cagcccagct tggagcgaac    1200
gacctacacc gaactgagat acctacagcg tgagctatga aaagcgcca cgcttcccga    1260
agggagaaag gcggacaggt atccggtaag cggcagggtc ggaacaggag agcgcacgag    1320
ggagcttcca gggggaaacg cctggtatct ttatagtcct gtcgggtttc gccacctctg    1380
acttgagcgt cgatttttgt gatgctcgtc aggggggcgg agcctatgga aaaacgccag    1440
caacgcggcc ttttacggtt cctggccttt tgctggcctt tttgctcaca tgttctttcc    1500
tgcgttatcc cctgattctg tggataaccg tattaccgcc tttgagtgag ctgataccgc    1560
tcgccgcagc cgaacgaccg agcgcagcga gtcagtgagc gaggaagcgg aagagcgccc    1620
aatacgcaaa ccgcctctcc ccgcgcgttg gccgattcat taacttaatt gcacgttgaa    1680
gcgttacctg ttaggtaacg tagttgagct gtgcaattaa ttttttaaga gtatagttga    1740
gctgtcacag aatgtgacgt tgaagtactc ttagaagtgt cccaactaca ctagaaggac    1800
agtggcgaga ggattacgcg cctagatcaa ctttaatgtt gactcgtgca cccaacatgc    1860
ttttagctc acgttgaagc gttacctgtt aggtaacgta gttgagctgt gagctaaatt    1920
ttttcaatgt gtagttgagc tgtcacagaa tgtgacgttg aagcacattg agggctgcta    1980
ttaagacacg acttatccct ttctcaaaag gccagcaaag cgatctggcc ccaataggggg    2040
aacaagaggc agaacatatc aaagcgacgt tgaagcgtta cctgttaggt aacgtagttg    2100
agctgtcgct ttgattttt cggtaagtag ttgagctgtc acagaatgtg acgttgaagc    2160
ttaccgagaa tagacacccg ccttacgcg aggcgaaggg ctttaaatca atctagagca    2220
tcataccagg cgtttcgttc ttggcgccgc aaccacctgt atgcacgttg aagcgttacc    2280
```

```
tgttaggtaa cgtagttgag ctgtgcatac agttcctgcg gtctatagtt gagctgtcac    2340
agaatgtgac gttgaagtag accgcgaaaa atgacgggga aagcctggcg aataactacg    2400
ttgcctgact cccggggata ttctcatagc tcactaacta ttgtgctgta gagctccgtc    2460
tacgttgaag cgttacctgt taggtaacgt agttgagctg tagacggagt ttttttggtc    2520
gctagttgag ctgtcacaga atgtgacgtt gaaggcgacc aaactctcag ggttattgtc    2580
tgatttatcg cgtccggcgg tgctacagac ccctggtccg ccccctgac aagtataaaa     2640 ccagcattta tcaaggatac gttgaagcgt tacctgttag gtaacgtagt tgagctgtat    2700
ccttgatttt ttgccctgat agttgagctg tcacagaatg tgacgttgaa gtcagggcat    2760
aaatcgcgtt aatattttgc gcggggatta agttgcgcct tatccgggct gtagtatcca    2820
cagaatcacg cgtatgtttg tcattgtaaa aagaacgtt gaagcgttac ctgttaggta     2880
acgtagttga gctgttcttt ttttttttca ccgaagtagt tgagctgtca cagaatgtga    2940
cgttgaagct tcggtgtttg gtccatccaa aaaggatctt cacagaaaaa tgtttgcaag    3000
cagcagtatt tcattcagaa agcggtctgt gactggtgat aacccaatac tcacgttgaa    3060
gcgttacctg ttaggtaacg tagttgagct gtgagtattg tttttcgctc ctttagttga    3120
gctgtcacag aatgtgacgt tgaagaagga gcgggaaggc aatgatgagg cacctatctc    3180
aaggccacgg atacctgtcc ggccactggt gcgggaggga agcactatta aagaaccagt    3240
ttggttccgc acgttgaagc gttacctgtt aggtaacgta gttgagctgt gcggaacctt    3300
ttttcctgta gtagttgagc tgtcacagaa tgtgacgttg aagctacagg aagttggctg    3360
cataattctc tttcaccaaa tgccgcaaaa aaaattgttg tgtcacccag ttaccttcgg    3420
aaaccactga tcttttctac gttaagggag ctagacgttg aagcgttacc tgttaggtaa    3480
cgtagttgag ctgtctagct cctttttcca cgccttagtt gagctgtcac agaatgtgac    3540
gttgaagagg cgtgggcgct cttccgatac ggtgtatctc agttcggcga ccgctgggta    3600
accctaaaca ctacgtgaac caccgaaatt cgcgttacgt tgaagcgtta cctgttaggt    3660
aacgtagttg agctgtaacg cgaacctttc tcatgatag ttgagctgtc acagaatgtg     3720
acgttgaagt catgaggatc cttcgctggt agcggtggct gaaggctcgt ccctccgaat    3780
gccatccgta agtgatctta gggcgacacg gaatccgcct atggcttggt atctacgttg    3840
aagcgttacc tgttaggtaa cgtagttgag ctgtagatac cattttttgca agttttagtt    3900 gagctgtcac agaatgtgac gttgaagaaa cttgcatagg caagctccct cgtgcgtatg    3960
tacattcgct gtagcgtctt gcccggcgtc ggaaaacgga tacatatttg agacccacgc    4020
tgcgcattag cacgttgaag cgttacctgt taggtaacgt agttgagctg tgctaatgct    4080
tttttgaacg aatagttgag ctgtcacaga atgtgacgtt gaagttcgtt catgtgagcc    4140
cttcgggaag cgcccggtac gccagcggcg aacccaacgt caaagggaga taggaaagtg    4200
ccacctaagt gtagaagggg gacgtcttga cgttgaagcg ttacctgtta ggtaacgtag    4260
ttgagctgtc aagacgtttt tttgcgtcga tagttgagct gtcacagaat gtgacgttga    4320
agtcgacgca tgaagtcgag cgccctttt gatccagttc gatggtactc accatgttgt     4380
gcaaactccg gtgtcctgcc ttttaaatta aaatcaagtc aaacccgacg ttgaagcgtt    4440
acctgttagg taacgtagtt gagctgtcgg gtttgttttt tcttttata gttgagctgt      4500 cacagaatgt gacgttgaag taaaagaat cagtaccgcg tatgtattaa gtgctcatca     4560
ttaatacgga gggcgctggc aagcattcag gctcaccagt taccaatgct tgccgcgttg    4620
ttccgacgtt gaagcgttac ctgttaggta acgtagttga gctgtcggaa caatttttgg    4680
```

```
tcctgttagt tgagctgtca cagaatgtga cgttgaagac aggacctacg gcgatcaagt    4740
gatcccacca agtcattctg ctgttgacaa tattattgaa gccagccggc ttaataagtg    4800
gtggcctaat ataaagacaa aaacgttgaa gcgttacctg ttaggtaacg tagttgagct    4860 gttttttgtct ccttcagcag ggttagttga gctgtcacag aatgtgacgt tgaagacct    4920 gctaacagga actgttgggc gctgataata ccgcgccact ttaatagaaa aataaacaag    4980
tgctggcgat cggcagcagc cactggcgct tacggaaccg acgttgaagc gttacctgtt    5040
aggtaacgta gttgagctgt cggttccgtt tttacagagc gtagttgagc tgtcacagaa    5100
tgtgacgttg aagcgctctg ttttttaagg atctcaagaa attatcagtc tattgggaat    5160
acagcatctt ttacttactg tctcgttgtc agaagtcatc gtggccggga attttggacg    5220
ttgaagcgtt acctgttagg taacgtagtt gagctgtcca aaattttttt gcctcgctta    5280
gttgagctgt cacagaatgt gacgttgaag agcgaggctc tcctgctggc gttttttcgtc    5340 tgacggctcc acatgagcgt tcttcggggc gagagttgcg tcacgctgcg cgttacaggg    5400
cagcaattat gagtacgttg aagcgttacc tgttaggtaa cgtagttgag ctgtactcat    5460
aacctttcca ttggatagtt gagctgtcac agaatgtgac gttgaagtcc aatggcgcta    5520
cgcaggaaag aacatccata gatacggtcc ccgagttgag tgttgttcgt ggactgtggc    5580
gagaaaggac ctcttctacc atctgtctat acgttgaagc gttacctgtt aggtaacgta    5640
gttgagctgt atagacagtt tttaggctga atagttgagc tgtcacagaa tgtgacgttg    5700
aagttcagcc tgtaggtact caaaggcggt acttcctcgc caacgttaaa atcggcaaaa    5760
tcccttgatg gccgggagcc cccgattcaa ggcgacgttg aagcgttacc tgttaggtaa    5820
cgtagttgag ctgtcgcctt gattttttgct cacattagtt gagctgtcac agaatgtgac    5880
gttgaagatg tgagctacaa cgtcgtgact gggaaaaccc tggcgttacc caacttaatc    5940
gccttgcagc acatccccct ttcgccagct ggcgtaatag cgaagaggcc cgcaccgatc    6000
gcccttccca acagttgcgc agcctgaatg gcgaatggga cgcgccctgt agcggcgcat    6060
taagcgcggc gggtgtggtg gttacgcgca gcgtgaccgc tacacttgcc agcgccctag    6120
cgcccgctcc tttcgctttc ttcccttcct ttctcgccac gttcgccggc tttccccgtc    6180
aagctctaaa tcggggggctc cctttagggt tccgatttag tgctttacgg cacctcgacc    6240
ccaaaaaact tgattagggt gatggttcac gtagtgggcc atcgccctga tagacggttt    6300
ttcgcccttt gacgttggag tccacgttct ttaatagtgg actcttgttc caaactggaa    6360
caacactcaa ccctatctcg gtctattctt ttgatttata agggattttg ccgatttcgg    6420
cctattggtt aaaaaatgag ctgatttaac aaaaatttaa cgcgaatttt aacaaaatat    6480
taacgcttac aatttaggtg gcacttttcg gggaaatgtg cgcggaaccc ctatttgttt    6540 attttctaa atacattcaa atatgtatcc gctcatgaga caataaccct gataaatgct    6600
tcaataatat tgaaaaagga agagtatgag tattcaacat ttccgtgtcg cccttattcc    6660
cttttttgcg gcattttgcc ttcctgtttt tgctcaccca gaaacgctgg tgaaagtaaa    6720
agatgctgaa gatcagttgg gtgcacgagt gggttacatc gaactggatc tcaacagcgg    6780
taagatcctt gagagttttc gccccgaaga acg                                 6813
```

<210> SEQ ID NO 29  
<211> LENGTH: 6731  
<212> TYPE: DNA  
<213> ORGANISM: Artificial Sequence  
<220> FEATURE:

<223> OTHER INFORMATION: Phagemid

<400> SEQUENCE: 29

```
ttagattgat ttaaaacttc attttttaatt taaaaggatc taggtgaaga tccttttttga      60
taatctcatg accaaaatcc cttaacgtga gttttcgttc cactgagcgt cagacccgt       120
agaaaagatc aaaggatctt cttgagatcc ttttttttctg cgcgtaatct gctgcttgca     180
aacaaaaaaa ccaccgctac cagcggtggt ttgtttgccg gatcaagagc taccaactct     240
tttccgaag gtaactggct tcagcagagc gcagatacca aatactgtcc ttctagtgta       300
gccgtagtta ggccaccact tcaagaactc tgtagcaccg cctacatacc tcgctctgct     360
aatcctgtta ccagtggctg ctgccagtgg cgataagtcg tgtcttaccg ggttggactc     420
aagacgatag ttaccggata aggcgcagcg gtcgggctga acggggggtt cgtgcacaca     480
gcccagcttg gagcgaacga cctacaccga actgagatac ctacagcgtg agctatgaga     540
aagcgccacg cttcccgaag ggagaaaggc ggacaggtat ccggtaagcg gcagggtcgg     600
aacaggagag cgcacgaggg agcttccagg gggaaacgcc tggtatcttt atagtcctgt     660
cgggtttcgc cacctctgac ttgagcgtcg attttttgtga tgctcgtcag gggggcggag     720
cctatggaaa aacgccagca acgcggcctt tttacggttc ctggcctttt gctggccttt     780
tgctcacatg ttctttcctg cgttatcccc tgattctgtg ataaccgta ttaccgcctt      840
tgagtgagct gataccgctc gccgcagccg aacgaccgag cgcagcgagt cagtgagcga     900
ggaagcggaa gagcgcccaa tacgcaaacc gcctctcccc gcgcgttggc cgattcatta     960
acttaattgc gttgaagcgt tacctgttag gtaacgtagt tgagctgcaa ttaatttttt    1020
aagagtatag ttgagctgtc acagaatgtg acgttgaagt actcttagaa gtgtcccaac    1080
tacactagaa ggacagtggc gagaggatta cgcgcctaga tcaactttaa tgttgactcg    1140
tgcacccaac atgcttttta gctcgttgaa gcgttacctg ttaggtaacg tagttgagct    1200
gagctaaatt ttttcaatgt gtagttgagc tgtcacagaa tgtgacgttg aagcacattg    1260
agggctgcta ttaagacacg acttatccct ttctcaaaag gccagcaaag cgatctggcc    1320
ccaatagggg aacaagaggc agaacatatc aaagcgagtt gaagcgttac ctgttaggta    1380
acgtagttga gcttcgcttt gttttttttcgg taagtagttg agctgtcaca gaatgtgacg    1440
ttgaagctta ccgagaatag acacccgcct tacagcgagg cgaagggctt taaatcaatc    1500
tagagcatca taccaggcgt ttcgttcttg gcgccgcaac cacctgtatg cgttgaagcg    1560
ttacctgtta ggtaacgtag ttgagctgca tacagttttt gcggtctata gttgagctgt    1620
cacagaatgt gacgttgaag tagaccgcga aaaatgacgg ggaaagcctg gcgaataact    1680
acgttgcctg actcccgggg atattctcat agctcactaa ctattgtgct gtagagctcc    1740
gtctagttga agcgttacct gttaggtaac gtagttgagc ttagacggat tttattggtc    1800
gctagttgag ctgtcacaga atgtgacgtt gaaggcgacc aaaactctcag ggttattgtc    1860
tgatttatcg cgtccggcgg tgctacagac ccctggtccg ccccctgac aagtataaaa     1920
ccagcattta tcaaggatgt tgaagcgtta cctgttaggt aacgtagttg agctatcctt    1980
gattttttgc cctgatagtt gagctgtcac agaatgtgac gttgaagtca gggcataaat    2040
cgcgttaata ttttgcgcgg ggattaagtt gcgccttatc cgggctgtag tatccacaga    2100
atcacgcgta tgtttgtcat tgtaaaaaag aagttgaagc gttacctgtt aggtaacgta    2160
gttgagcttt cttttttttt tcaccgaagt agttgagctg tcacagaatg tgacgttgaa    2220
gcttcggtgt ttggtccatc caaaaaggat cttcacagaa aaatgtttgc aagcagcagt    2280
```

```
atttcattca gaaagcggtc tgtgactggt gataacccaa tactcagttg aagcgttacc    2340
tgttaggtaa cgtagttgag cttgagtatt tttttcgctc ctttagttga gctgtcacag    2400
aatgtgacgt tgaagaagga gcgggaaggc aatgatgagg cacctatctc aaggccacgg    2460 ataccctgtcc ggccactggt gcgggaggga agcactatta agaaccagt ttggttccgc    2520 gttgaagcgt tacctgttag gtaacgtagt tgagctgcgg aacctttat cctgtagtag    2580 ttgagctgtc acagaatgtg acgttgaagc tacaggaagt tggctgcata attctctttc    2640
accaaatgcc gcaaaaaaaa ttgttgtgtc acccagttac cttcggaaac cactgatctt    2700
ttctacgtta agggagctag agttgaagcg ttacctgtta ggtaacgtag ttgagcttct    2760
agctcttttt ccacgcctta gttgagctgt cacagaatgt gacgttgaag aggcgtgggc    2820
gctcttccga tacggtgtat ctcagttcgg cgaccgctgg gtaaccctaa acactacgtg    2880
aaccaccgaa attcgcgttg ttgaagcgtt acctgttagg taacgtagtt gagctaacgc    2940
gaaaattacc tcatgatagt tgagctgtca cagaatgtga cgttgaagtc atgaggatcc    3000
ttcgctggta gcggtggctg aaggctcgtc cctccgaatg ccatccgtaa gtgatcttag    3060
ggcgacacgg aatccgccta tggcttggta tctgttgaag cgttacctgt taggtaacgt    3120
agttgagcta gataccattt tagcaagttt tagttgagct gtcacagaat gtgacgttga    3180
agaaacttgc ataggcaagc tccctcgtgc gtatgtacat tcgctgtagc gtcttgcccg    3240
gcgtcggaaa acggatacat atttgagacc cacgctgcgc attagcagtt gaagcgttac    3300
ctgttaggta acgtagttga gcttgctaat gttttttgaa cgaatagttg agctgtcaca    3360
gaatgtgacg ttgaagttcg ttcatgtgag cccttcggga agcgcccggt acgccagcgg    3420
cgaacccaac gtcaaaggga gataggaaag tgccacctaa gtgtagaagg gggacgtctt    3480
ggttgaagcg ttacctgtta ggtaacgtag ttgagctcaa gacgtttttt tgcgtcgata    3540
gttgagctgt cacagaatgt gacgttgaag tcgacgcatg aagtcgagcg cccttttga    3600 tccagttcga tggtactcac catgttgtgc aaactccggt gtcctgcctt ttaaattaaa    3660
atcaagtcaa acccggttga agcgttacct gttaggtaac gtagttgagc tcgggtttgt    3720
tttatctttt tatagttgag ctgtcacaga atgtgacgtt gaagtaaaaa gaatcagtac    3780
cgcgtatgta ttaagtgctc atcattaata cggagggcgc tggcaagcat tcaggctcac    3840
cagttaccaa tgcttgccgc gttgttccgg ttgaagcgtt acctgttagg taacgtagtt    3900
gagctcggaa caatttttgg tcctgttagt tgagctgtca cagaatgtga cgttgaagac    3960
aggacctacg gcgatcaagt gatcccacca agtcattctg ctgttgacaa tattattgaa    4020
gccagccggc ttaataagtg gtggcctaat ataaagacaa aaagttgaag cgttacctgt    4080
taggtaacgt agttgagctt ttttgtcaat taagcagggt tagttgagct gtcacagaat    4140
gtgacgttga agaccctgct aacaggaact gttgggcgct gataataccg cgccacttta    4200
atagaaaaat aaacaagtgc tggcgatcgg cagcagccac tggcgcttac ggaaccggtt    4260
gaagcgttac ctgttaggta acgtagttga gctcggttcc gattttacag agcgtagttg    4320
agctgtcaca gaatgtgacg ttgaagcgct ctgttttta aggatctcaa gaaattatca    4380
gtctattggg aatacagcat cttttactta ctgtctcgtt gtcagaagtc atcgtggccg    4440
ggaattttgg gttgaagcgt tacctgttag gtaacgtagt tgagctccaa aattttttg    4500 cctcgcttag ttgagctgtc acagaatgtg acgttgaaga gcgaggctct cctgctggcg    4560 ttttttcgtct gacggctcca catgagcgtt cttcggggcg agagttgcgt cacgctgcgc    4620
```

```
gttacagggc agcaattatg agtgttgaag cgttacctgt taggtaacgt agttgagcta    4680
ctcataaatt tccattggat agttgagctg tcacagaatg tgacgttgaa gtccaatggc    4740
gctacgcagg aaagaacatc catagatacg gtccccgagt tgagtgttgt tcgtggactg    4800
tggcgagaaa ggacctcttc taccatctgt ctatgttgaa gcgttacctg ttaggtaacg    4860
tagttgagct atagacagtt tttaggctga atagttgagc tgtcacagaa tgtgacgttg    4920
aagttcagcc tgtaggtact caaaggcggt acttcctcgc caacgttaaa atcggcaaaa    4980
tcccttgatg gccgggagcc cccgattcaa ggcggttgaa gcgttacctg ttaggtaacg    5040
tagttgagct cgccttgatt tttgctcaca ttagttgagc tgtcacagaa tgtgacgttg    5100
aagatgtgag ctacaacgtc gtgactggga aaaccctggc gttacccaac ttaatcgcct    5160
tgcagcacat cccctttcg ccagctggcg taatagcgaa gaggcccgca ccgatcgccc    5220
ttcccaacag ttgcgcagcc tgaatggcga atgggacgcg ccctgtagcg gcgcattaag    5280
cgcggcgggt gtggtggtta cgcgcagcgt gaccgctaca cttgccagcg ccctagcgcc    5340
cgctcctttc gctttcttcc cttcctttct cgccacgttc gccggctttc cccgtcaagc    5400
tctaaatcgg gggctccctt tagggttccg atttagtgct ttacggcacc tcgaccccaa    5460
aaaacttgat tagggtgatg gttcacgtag tgggccatcg ccctgataga cggttttttcg    5520
cccctttgacg ttggagtcca cgttctttaa tagtggactc ttgttccaaa ctggaacaac    5580
actcaaccct atctcggtct attctttga tttataaggg attttgccga tttcggccta    5640
ttggttaaaa aatgagctga tttaacaaaa atttaacgcg aattttaaca aaatattaac    5700
gcttacaatt taggtggcac ttttcgggga aatgtgcgcg gaaccccctat tgtttattt    5760
ttctaaatac attcaaatat gtatccgctc atgagacaat aaccctgata aatgcttcaa    5820
taatattgaa aaaggaagag tatgagtatt caacatttcc gtgtcgccct tattcccttt    5880
tttgcggcat tttgccttcc tgtttttgct cacccagaaa cgctggtgaa agtaaaagat    5940
gctgaagatc agttgggtgc acgagtgggt tacatcgaac tggatctcaa cagcggtaag    6000
atccttgaga gttttcgccc cgaagaacgt tttccaatga tgagcacttt taaagttctg    6060
ctatgtggcg cggtattatc ccgtattgac gccgggcaag agcaactcgg tcgccgcata    6120
cactattctc agaatgactt ggttgagtac tcaccagtca cagaaaagca tcttacggat    6180
ggcatgacag taagagaatt atgcagtgct gccataacca tgagtgataa cactgcggcc    6240
aacttacttc tgacaacgat cggaggaccg aaggagctaa ccgcttttttt gcacaacatg    6300
ggggatcatg taactcgcct tgatcgttgg gaaccggagc tgaatgaagc cataccaaac    6360
gacgagcgtg acaccacgat gcctgtagca atggcaacaa cgttgcgcaa actattaact    6420
ggcgaactac ttactctagc ttcccggcaa caattaatag actggatgga ggcggataaa    6480
gttgcaggac cacttctgcg ctcggccctt ccggctggct ggtttattgc tgataaatct    6540
ggagccggtg agcgtgggtc acgcggtatc attgcagcac tggggccaga tggtaagccc    6600
tcccgtatcg tagttatcta cacgacgggg agtcaggcaa ctatggatga acgaaataga    6660
cagatcgctg agataggtgc ctcactgatt aagcattggt aactgtcaga ccaagtttac    6720
tcatatatac t                                                        6731
```

<210> SEQ ID NO 30  
<211> LENGTH: 9059  
<212> TYPE: DNA  
<213> ORGANISM: Artificial Sequence  
<220> FEATURE:  
<223> OTHER INFORMATION: Phagemid 48helix tube

<400> SEQUENCE: 30

```
gacgtaacgg tgctgtctaa catcgagact gcaattaccc cgccagacct ttgcacttcc    60
acactaattt ggtcgatctt tgcttaaccg ggaactatgt agtctatatg agaatattga   120
gcataaggtg tcagccagcc tttatccttg aggcagatca ggtctattcg ctcagagtaa   180
gatgctaaca cccagtagat gacgacgttt aattagggcc gagagaccaa tgtcacgcat   240
taagcgcggc gggtgtggtg gttacgcgca gcgtgaccgc tacacttgcc agcgccctag   300
cgcccgctcc tttcgctttc ttcccttcct ttctcgccac gttcgccggc tttccccgtc   360
aagctctaaa tcgggggctc cctttagggt tccgatttag tgctttacgg cacctcgacc   420
ccaaaaaact tgattagggt gatggttcac gtagtgggcc atcgccctga tagacggttt   480
ttcgcccttt gacgttggag tccacgttct ttaatagtgg actcttgttc caaactggaa   540
caacactcaa ccctatctcg gtctattctt ttgatttata agggattttg ccgatttcgg   600
cctattggtt aaaaaatgag ctgatttaac aaaaatttaa cgcgaatttt aacaaaatat   660
taacgcttac aatttaggtg gcacttttcg gggaaatgtg cgcggaacct tgatcgggca   720
cgtaagaggt tccaactttc accataatga aataagatca ctaccgggcg tattttttga   780
gttatcgaga ttttcaggag ctaaggaagc taaaatggag aaaaaaatca ctggatatac   840
caccgttgat atatcccaat ggcatcgtaa agaacatttt gaggcatttc agtcagttgc   900
tcaatgtacc tataaccaga ccgttcagct ggatattacg gcctttttaa agaccgtaaa   960
gaaaaataag cacaagtttt atccggcctt tattcacatt cttgcccgcc tgatgaatgc  1020
tcatccggaa tttcgtatgg caatgaaaga cggtgagctg gtgatatggg atagtgttca  1080
cccttgttac accgttttcc atgagcaaac tgaaacgttt tcatcgctct ggagtgaata  1140
ccacgacgat ttccggcagt ttctacacat atattcgcaa gatgtggcgt gttacggtga  1200
aaacctggcc tatttcccta aagggtttat tgagaatatg ttttcgtct cagccaatcc  1260
ctgggtgagt ttcaccagtt ttgatttaaa cgtggccaat atggacaact tcttcgcccc  1320
cgttttcacc atgggcaaat attatacgca aggcgacaag gtgctgatgc cgctggcgat  1380
tcaggttcat catgccgttt gtgatggctt ccatgtcggc agaatgctta atgaattaca  1440
acagtactgc gatgagtggc agggcggggc gtaatttgat atcgagctcg cttggactcc  1500
tgttgataga tccagtaatg acctcagaac tccatctgga tttgttcaga acgctcggtt  1560
gccgccgggc gttttttatt ggtgagaatc caagcctcga gctgtcagac caagtttact  1620
catatatact ttagattgat ttaaaacttc attttaatt taaaaggatc taggtgaaga  1680
tcctttttga taatctcatg accaaaatcc cttaacgtga gttttcgttc cactgagcgt  1740
cagacccccg agaaaagatc aaaggatctt cttgagatcc ttttttctg cgcgtaatct  1800
gctgcttgca acaaaaaaa ccaccgctac cagcggtggt ttgtttgccg gatcaagagc  1860
taccaactct ttttccgaag gtaactggct tcagcagagc gcagatacca aatactgttc  1920
ttctagtgta gccgtagtta ggccaccact tcaagaactc tgtagcaccg cctacatacc  1980
tcgctctgct aatcctgtta ccagtggctg ctgccagtgg cgataagtcg tgtcttaccg  2040
ggttggactc aagacgatag ttaccggata aggcgcagcg tcgggctga acgggggggtt  2100
cgtgcacaca gcccagcttg gagcgaacga cctacaccga actgagatac ctacagcgtg  2160
agctatgaga agcgccacg cttcccgaag ggagaaaggc ggacaggtat ccggtaagcg  2220
gcagggtcgg aacaggagag cgcacgaggg agcttccagg gggaaacgcc tggtatcttt  2280
```

```
atagtcctgt cgggtttcgc cacctctgac ttgagcgtcg attttttgtga tgctcgtcag    2340 gggggcggag cctatggaaa aacgccagca acgcggcctt tttacggttc ctggccttt     2400 gctggccttt tgctcacctt agcaagagcc gcacgacgac cagaggccag ttatccagag    2460
ttaggatacc tcaatgtgca tccgctcggt tctaaggaca ttatttcagt cctttaagat    2520
ctcccgtata gaagcctcac gttaggggc gccgtgcctt cacgccctcc catttaggaa     2580
taccttgtct ccgccgtctt tattcagtag ccctatgcat tacgatgtgg cgcttccccc    2640
gcgtgggcgc agaaatttac tgaggcggat tcgaaacgac tgtgagggca ggataggtga    2700
gcaggcactg gcacgtaatc aaccaacgga ctcacccgtg tgcaggccta aaaacagccc    2760
tcgaagggca cttggatatg aatgaaccca cttgttttga ctcgtggagg cgtggtttta    2820
ttactgtgct cagttaacgc cgcatgaatt tagctctgat caccgtaagg gtaactgcac    2880
tagacatgtt gtgggcattt aagtcctgca gtatcttttt gttaggtgga acggcctagg    2940
ggtaccttcc gtgagaaact cccagatgat gcatgttcga gtacttgtga aatggatggt    3000
cgcatcccct cctctcacac attacactgt ctcgcgcggg ttgcgtcttg accggtacaa    3060
gttgtgtaac cttacacctc tagaaacatt ttagcagtcg ctccaattga taccacgacc    3120
tcagcgcgcg ttgggagacc gttgccaaac ctagacgttaa agcgttacc tgttaggtaa    3180 cgtagttgag ctgtctaggt tttttttgca tctggtagtt gagctgtcac agaatgtgac    3240
gttgaagcca gatgcaccaa tgtatataaa tagatccttt taaattaaat aaatcaatcg    3300
taatactgaa ctaggttctc ccaaggtgta accgtaaacc gccccacgtt gaagcgttac    3360
ctgttaggta acgtagttga ctgtggggc ggttttttaa tccaagtagt tgagctgtca    3420
cagaatgtga cgttgaagct tggattctga gttctgcacg gctcaattcg cgttaaattt    3480
ttggcgaggg cgtgaaggag gtcattactg gtaagctcga ggacgttgaa gcgttacctg    3540
ttaggtaacg tagttgagct gtcctcgagc ttttttcccgt agatagttga gctgtcacag    3600
aatgtgacgt tgaagtctac ggggtctata atatttgaag ttgtggccca agttttttgg    3660
ggtcaaggga gttttcggaa aaagagaaac tctggccaca cgttgaagcg ttacctgtta    3720
ggtaacgtag ttgagctgtg tggccagttt ttaaaaaaaa tagttgagct gtcacagaat    3780
gtgacgttga agttttttt tttttttttt ttaggatcta ttacgctttt tttttttttt    3840 tttttttgcct gcatcgaggg tttttttttt tttttttttt acgttgaagc gttacctgtt    3900
aggtaacgta gttgagctgt aaaaaaaatt ttttaccgct atagttgagc tgtcacagaa    3960
tgtgacgttg aagtagcggt aaacaaaaca agtgcgcctc ctgcagttgc ccacacaaaa    4020
agcacgaact tctcatagct cactctccct catccatcag tgtacggtca attctagacg    4080
cgcgcacgtt gaagcgttac ctgttaggta acgtagttga ctgtgcgcg cgtttttgga    4140 gggttttagt tgagctgtca cagaatgtga cgttgaagaa accctccccc gagcgaacgt    4200
ggcgcgctcc agatgcgaat atatgtgaag ccagttacca gggaaataca catctgcgat    4260
gaacgttgaa gcgttacctg ttaggtaacg tagttgagct gttcatcgca tttttatact    4320
gtttagttga gctgtcacag aatgtgacgt tgaagaacag tatacggcta gagttctatg    4380
tagcaacccg aactatcgcc cgaccgctgc gctgtgtgat actgcgtacc cctaggccga    4440
tgcgactcgg gaaaagctcc acgttgaagc gttacctgtt aggtaacgta gttgagctgt    4500
ggagcttttt tttcgcgtgt ttagttgagc tgtcacagaa tgtgacgttg aagaacacgc    4560
ggccaggtct caattgagac ggggcgaagc ccatgccttg tcgccttgcc ctgaattatc    4620 agggactcc acgttgaagc gttacctgtt aggtaacgta gttgagctgt ggagtccctt     4680
```

```
tttagtttct atagttgagc tgtcacagaa tgtgacgttg aagtagaaac tgccgtggcc   4740
taactttggt aatccggcgg ttttttttgtt aaaactggtg ttggtaaaat cggacgttga   4800
agcgttacct gttaggtaac gtagttgagc tgtccgattt ttttttttttc catgtagttg   4860 agctgtcaca gaatgtgacg ttgaagcatg gaaaaacgtt aaagccgttt agagctaatc   4920
actacgtgaa ccgtccgcca gcactgttgt aattcacccc gccatagggt aatcccttct   4980
cgatgaagtg cagcaaaggt gatctcctta gcacgttgaa gcgttacctg ttaggtaacg   5040
tagttgagct gtgctaagga ttttttacacc gtttagttga gctgtcacag aatgtgacgt   5100
tgaagaacgt gtaacagcc actggtgtat tcagcgttaa accctagag gtgcattacg   5160 tgccaggatc catatacccca gggattggca cgttgaagcg ttacctgtta ggtaacgtag   5220
ttgagctgtg ccaatccttt ttaaaaaaaa tagttgagct gtcacagaat gtgacgttga   5280
agtttttttt tttttttttt ttcaccgtca tcccattttt ttttttttttt tttttgggc   5340 gctaagaaag tttttttttt tttttttttt acgttgaagc gttacctgtt aggtaacgta   5400
gttgagctgt aaaaaaaatt tttctcatcc gtagttgagc tgtcacagaa tgtgacgttg   5460
aagcggatga gcattttatc cggtgtaaga ccttaaatac ccttacggtg atcagtaatg   5520
ggaaatcgtc gtgaacagga atcgccaacg ttgaagcgtt acctgttagg taacgtagtt   5580
gagctgttgg cgatttttttt ctggagcgta gttgagctgt cacagaatgt gacgttgaag   5640
cgctccagta tctcagttcg gtaccggaaa catgcgataa aggctggcgg tcagaggtgg   5700
cacaatctcg ataaccgttt ttcccgctca acgcgagatt cacaaacgga agaggtaacc   5760
accacaacgt tgaagcgtta cctgttaggt aacgtagttg agctgttgtg gtggttttta   5820
acaggtatag ttgagctgtc acagaatgtg acgttgaagt acctgttgtt ccgaccctgc   5880
cagaaacccg acaggactat agctctcccc gccttgctgt agagctgggc ccatcaggcg   5940
ggcaagaatg ggtcgttccc gccgtctggg agtttctcgt actcgacgtt gaagcgttac   6000
ctgttaggta acgtagttga gctgtcgagt acgtttttg cacgagtagt tgagctgtca   6060
cagaatgtga cgttgaagct cgtgcaagat acaaatcgaa taggctaagg ccgaaaaggc   6120
ggataactgg cctctagaac ctgaggtcga atcttcaac gttaaagaca acgtgaaaca   6180
aatacgttga agcgttacct gttaggtaac gtagttgagc tgtatttgtt tttttcttc   6240 aggatagttg agctgtcaca gaatgtgacg ttgaagtcct gaaggtggta cctcaagata   6300
ctgggtgtta gggtacattg agccttgaaa ggccgtaata tccagcggtt atacatctta   6360
atagacctat agacccggtt aaaaggtccc acctaagctc atacgttgaa gcgttacctg   6420
ttaggtaacg tagttgagct gtatgagctt tttttcctcc gcttagttga gctgtcacag   6480
aatgtgacgt tgaagagcgg aggactgaaa taatggcccc ctggcggaga cgggaagcgc   6540
cacatctaaa aaaaaacgcc cggccgttct gggcttcttc ttaaatgcac attaactctc   6600
agcaaaacgt tgaagcgtta cctgttaggt aacgtagttg agctgttttg ctgatttta   6660 accttgttag ttgagctgtc acagaatgtg acgttgaaga caaggtttac gtcgtggtat   6720
caattatata ttttgttaac ttggtcgtcg tgcatcaagg ttagcgttat agtgtggtta   6780
gacacgttga agcgttacct gttaggtaac gtagttgagc tgtgtctaac cttttctga   6840 cgtttagttg agctgtcaca gaatgtgacg ttgaagaacg tcagaccgag ctgccacgct   6900
cgatatcaaa tatctatcga aatcgttaaa tcaattgtac cgcgcaacct cttacgtgcc   6960
cccggtaatc gaccgctcaa tacgttgaag cgttacctgt taggtaacgt agttgagctg   7020
```

```
tattgagcgt ttttattaat agtagttgag ctgtcacaga atgtgacgtt gaagctatta      7080
atgttccaac ttggtctgac cgttaagcat gatgaagtga cgctcagtgg aacgaaacat      7140
cacatatcct ggagtccaac gttgaagcgt tacctgttag gtaacgtagt tgagctgttg      7200
gactcctttt ttgattcgat agttgagctg tcacagaatg tgacgttgaa gtcgaatcaa      7260
tttctgcgcc cacgcggaac cctcacgagt ccgtctgcaa gcagcagcaa gaagttaagg      7320
gattttggat caaaaacgtt gaagcgttac ctgttaggta acgtagttga gctgttttg      7380
atcttttttgc tttacgtagt tgagctgtca cagaatgtga cgttgaagcg taaagcatcc      7440
aagtgccctc acgggtagtc gttaggatct tcaccgcact cacgatcctt tgatctttgt      7500
ttaaattggt tgacgttgaa gcgttacctg ttaggtaacg tagttgagct gtcaaccaat      7560
tttttgtgct cagtagttga gctgtcacag aatgtgacgt tgaagctgag cacagagctg      7620
tcacgctgcg cgaacgactt ttagcagagc gaggttgaag taaaaccagg ttcattcata      7680
ctgctcttgt ctgcgctctg ctgacgttga agcgttacct gttaggtaac gtagttgagc      7740
tgtcagcaga gttttttatga attttagttg agctgtcaca gaatgtgacg ttgaagaaat      7800
tcatgagaaa ggaagggagg gcgctgcgtg ataccggtctt taatatgaat aagccatacg      7860
aaattcctgg cagtgtagcg acgttgaagc gttacctgtt aggtaacgta gttgagctgt      7920
cgctacactt tttattaagc gtagttgagc tgtcacagaa tgtgacgttg aagcgcttaa      7980
tggcaagcaa gggtgaacac ttttcattag gccggataaa acttttcttc attggttaat      8040
taaacgtcgt catctcaacg ttgaagcgtt acctgttagg taacgtagtt gagctgttga      8100
gatgattttt atgagaatta gttgagctgt cacagaatgt gacgttgaag attctcatga      8160
tctgtatcca gccattggga tatatcgaac tgactgaaat gcctcatacg atgtgatttt      8220
ttagctttat ttcaagttgg acatttccac gttgaagcgt tacctgttag gtaacgtagt      8280
tgagctgtgg aaatgttttt tggttgcgtt agttgagctg tcacagaatg tgacgttgaa      8340
gacgcaaccc tgacacctta taaggagcga ctgctggtca aaaaatacgc gggctcttgc      8400
taaggtgagc cgttgctaaa atgtacgttg aagcgttacc tgttaggtaa cgtagttgag      8460
ctgtacattt tatttttaaa aaaaatagtt gagctgtcac agaatgtgac gttgaagttt      8520
tttttttttt tttttttctt gtacatgtgt gttttttttt ttttttttt tatcacaaca      8580
ggcgtttttt tttttttttt ttttacgtt gaagcgttac ctgttaggta acgtagttga      8640
gctgtaaaaa aaatttttaa aaaaaatagt tgagctgtca cagaatgtga cgttgaagtt      8700
tttttttttt ttttttttat tgcagtataa attttttttt tttttttttt ttataggcca      8760
acaggatttt tttttttttt tttttacgt tgaagcgtta cctgttaggt aacgtagttg      8820
agctgtaaaa aaaattttta atcggtgtag ttgagctgtc acagaatgtg acgttgaagc      8880
accgattcct aaatggaatg agtgtagaac gtgctgcctg ctcaccaacg gcattctgcc      8940
gacatggtga gtaagtttgg aacgttgaag cgttacctgt taggtaacgt agttgagctg      9000
ttccaaactt ttttgtcgaa attagttgag ctgtcacaga atgtgacgtt gaagatttc      9059
```

<210> SEQ ID NO 31
<211> LENGTH: 8027
<212> TYPE: DNA
<213> ORGANISM: Artificial Sequence
<220> FEATURE:
<223> OTHER INFORMATION: Phagemid pointer - part 1

<400> SEQUENCE: 31

```
atgagtattc aacatttccg tgtcgccctt attcccttt ttgcggcatt ttgccttcct        60
```

```
gtttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta gcattggta actgtcagac caagtttact catatatact ttagattgat    900
ttaaaacttc attttaatt taaaaggatc taggtgaaga tcctttttga taatctcatg    960
accaaaatcc cttaacgtga gttttcgttc cactgagcgt cagacccgt agaaaagatc    1020 aaaggatctt cttgagatcc ttttttttctg cgcgtaatct gctgcttgca acaaaaaaa    1080 ccaccgctac cagcggtggt ttgtttgccg gatcaagagc taccaactct ttttccgaag    1140
gtaactggct tcagcagagc gcagatacca atactgtcc ttctagtgta gccgtagtta    1200
ggccaccact tcaagaactc tgtagcaccg cctacatacc tcgctctgct aatcctgtta    1260
ccagtggctg ctgccagtgg cgataagtcg tgtcttaccg ggttggactc aagacgatag    1320
ttaccggata aggcgcagcg gtcgggctga acggggggt cgtgcacaca gcccagcttg    1380
gagcgaacga cctacaccga actgagatac ctacagcgtg agctatgaga aagcgccacg    1440
cttcccgaag ggagaaaggc ggacaggtat ccggtaagcg gcagggtcgg aacaggagag    1500
cgcacgaggg agcttccagg gggaaacgcc tggtatcttt atagtcctgt cgggtttcgc    1560
cacctctgac ttgagcgtcg attttttgtga tgctcgtcag ggggcggag cctatggaaa    1620 aacgccagca acgcggcctt tttacggttc ctggcctttt gctggccttt tgctcactgc    1680
cctttgtagt tgagctgtca cagaatgtga cgttgaagca aagggcgggt gcctcgctca    1740
ctgcttaatg ttgcatgcgg tcacgttgac gttgaagcgt tacctgttag gtaacgtagt    1800
tgagctgtca acgtgatttt tacaacaatt agttgagctg tcacagaatg tgacgttgaa    1860
gattgttgtt ccgccaacc agggtggtgc aagcgacag gaagccggaa cgttgaagcg    1920
ttacctgtta ggtaacgtag ttgagctgtt ccggcttttt ttaaaaaaaa tagttgagct    1980
gtcacagaat gtgacgttga agttttttttt tgggtgaga cgggcgagtt tttttttaa    2040 agggtcgtgc cgaggatccc cgggttttta cgttgaagcg ttacctgtta ggtaacgtag    2100
ttgagctgta aaaacccttt ttcgatttcg tagttgagct gtcacagaat gtgacgttga    2160
agcgaaatcg cctggccctt gccccagagt aaaataacat cacttacgtt gaagcgttac    2220
ctgttaggta acgtagttga gctgtaagtg atgttttttct gattttttagt tgagctgtca    2280 cagaatgtga cgttgaagaa aatcagcccc cggcaggcga aaatcctgac gctggttgag    2340
agagggacgt tgaagcgtta cctgttaggt aacgtagttg agctgtccct ctcttttttt    2400
```

```
tacggcctag ttgagctgtc acagaatgtg acgttgaagg gccgtaaagc actaaatttt    2460
ttttttttcgg aaccggaaag ccggcgattt ttacgttgaa gcgttacctg ttaggtaacg   2520
tagttgagct gtaaaaatcg tttttgctaa aaatagttga gctgtcacag aatgtgacgt    2580
tgaagttttt agcggtcctt tttttttttt tgatggtggt tcaatagccc ttgggcacgt    2640
tgaagcgtta cctgttaggt aacgtagttg agctgtgccc aaggttttc gtaaaaatag    2700
ttgagctgtc acagaatgtg acgttgaagt tttacgtgg caacagctga gaagttttcc    2760
tttttttttt cagtcacgac gttgtacgtt gaagcgttac ctgttaggta acgtagttga    2820
gctgtacaac gtcttttttcc cgcgcgtagt tgagctgtca cagaatgtga cgttgaagcg    2880
cgcggggacg tgcttcgccg ctacagcttt caataggaat tgcggacgtt gaagcgttac    2940
ctgttaggta acgtagttga gctgtccgca atttttttaa aaccgctagt tgagctgtca    3000
cagaatgtga cgttgaaggc ggtttttttt ttttgcgta gagtttttttt tttatagggt    3060
tgagtaaaga acttacgttg aagcgttacc tgttaggtaa cgtagttgag ctgtaagttc    3120
tttttttctt aggtttagtt gagctgtcac agaatgtgac gttgaagaac ctaagggttt    3180
ttttttttaag aaagcgaaag gtcacgctag ctcttttttt tttgaattcg taatacgttg    3240
aagcgttacc tgttaggtaa cgtagttgag ctgtattacg aatttttatt caacgtagtt    3300
gagctgtcac agaatgtgac gttgaagcgt tgaatgagtg taaagtgtaa ttgttaagga    3360
agatgataat catgacgttg aagcgttacc tgttaggtaa cgtagttgag ctgtcatgat    3420
tattttttggc gggtttagtt gagctgtcac agaatgtgac gttgaagaac ccgccgcgcc    3480
cgctttaatg aatcagtttg gccttataaa tcaaaacgtt gaagcgttac ctgttaggta    3540
acgtagttga gctgttttga tttttttga gttaaatagt tgagctgtca cagaatgtga    3600
cgttgaagtt taactcgcgt ctttttttt ttgaaatgga tcaccatcaa ctgttttttt    3660
tttatagcaa acatacgttg aagcgttacc tgttaggtaa cgtagttgag ctgtatgttt    3720
gcttttacg ttttgtagtt gagctgtcac agaatgtgac gttgaagcaa aacgttaaaa    3780
ctagcttgag agatctggag ctcattgaat ccccctcgaa tcgacgttga agcgttacct    3840
gttaggtaac gtagttgagc tgtcgattcg atttttctta gagttagttg agctgtcaca    3900
gaatgtgacg ttgaagactc taagctgcat tccagtcgcg tgaaccgtct atcagggcga    3960
tgtttttttt ttgcccacta ggaacgttga agcgttacct gttaggtaac gtagttgagc    4020
tgttcctagt gttttttgtaa aaaatagttg agctgtcaca gaatgtgacg ttgaagtttt    4080
ttaccggcgc gtaaacaacc cgaaattttt taaaaattct gagtacgttg aagcgttacc    4140
tgttaggtaa cgtagttgag ctgtactcag aattttttcta cactgtagtt gagctgtcac    4200
agaatgtgac gttgaagcag tgtagcggag cgggcgctag ggcgaaaaac caacaagagt    4260
ccactacgtt gaagcgttac ctgttaggta acgtagttga gctgtagtgg actttttga    4320
taaaattagt tgagctgtca cagaatgtga cgttgaagat tttatcctcg ttcgtgcatc    4380
tggtgtagca ccagcactca gagcaaacgt tgaagcgtta cctgttaggt aacgtagttg    4440
agctgtttgc tctgtttttg ttaaaaatag ttgagctgtc acagaatgtg acgttgaagt    4500
ttttaaccag aggaatttt ttttaaacg ctccatcacc tcattagacg ttgaagcgtt    4560
acctgttagg taacgtagtt gagctgtcta atgagttttt cttctactta gttgagctgt    4620
cacagaatgt gacgttgaag agtagaaggt tgggtaacgc ctttttttt tagggtgttt    4680
ttatccaacg ttgaagcgtt acctgttagg taacgtagtt gagctgttgg ataaattttt    4740
atcaaagata gttgagctgt cacagaatgt gacgttgaag tctttgatta gtaagagtct    4800
```

```
gtgggcgatc ccaggcaaca ataacccaac gttgaagcgt tacctgttag gtaacgtagt    4860
tgagctgttg ggttattttt tgctgccagt agttgagctg tcacagaatg tgacgttgaa    4920
gctggcagct ttcgcgcgag caacaccgct cctgatttag aacctgaacg ttgaagcgtt    4980
acctgttagg taacgtagtt gagctgttca ggttcttttt ttcgtaatta gttgagctgt    5040
cacagaatgt gacgttgaag attacgaatc agtgcagaat cctgattgcc ttcaccaggt    5100
cgaggtatca cccaaatcaa gttttttacg ttgaagcgtt acctgttagg taacgtagtt    5160
gagctgtaaa aaactttttt tgcaaaaata gttgagctgt cacagaatgt gacgttgaag    5220
tttttgcaac gctagtttga catatctttt ttttttggt cagttggcac cgacgttgaa     5280
gcgttacctg ttaggtaacg tagttgagct gtcggtgcca tttttattaa tcgtagttga    5340
gctgtcacag aatgtgacgt tgaagcgatt aatagctcaa ctggaagtct tttgatctat    5400
tataccatcc tagtcctgac gttgaagcgt tacctgttag gtaacgtagt tgagctgtca    5460
ggactatttt tattaccagt agttgagctg tcacagaatg tgacgttgaa gctggtaata    5520
tccgaattga gccaattcta ggtcaggaaa aagatgcacg ttgaagcgtt acctgttagg    5580
taacgtagtt gagctgtgca tcttttttttt cggccgatta gttgagctgt cacagaatgt    5640
gacgttgaag atcggccggc ggattcagta ttggcaaaga gatgatgatt aacaataaac    5700
gttgaagcgt tacctgttag gtaacgtagt tgagctgttt attgttttttt tccgaagtt    5760 agttgagctg tcacagaatg tgacgttgaa gacttctggt cggtacgcag ccaccatttt    5820
agagcttgac ggctaaagac gttgaagcgt tacctgttag gtaacgtagt tgagctgtct    5880 ttagccttttt tagaactggt agttgagctg tcacagaatg tgacgttgaa gccagttctg    5940
agagctgttt agcattgcat cattagagaa aacgttgaag cgttacctgt taggtaacgt    6000
agttgagctg ttttctctat ttttcctttc ggtagttgag ctgtcacaga atgtgacgtt    6060
gaagccgaaa gggtacggtg tcatgttttg cggatggctt agagcttacg ttgaagcgtt    6120
acctgttagg taacgtagtt gagctgtaag ctctattttt cgcacccttta gttgagctgt    6180 cacagaatgt gacgttgaag aaggtgcggg gttgattcga aggttacttt aggagcacta    6240
acgttttaac gttgaagcgt tacctgttag gtaacgtagt tgagctgtta aaacgttttt    6300
tcctcctaat agttgagctg tcacagaatg tgacgttgaa gttaggaggc ccaaattaac    6360
cgtttttttt ttttgcagcc atttttttac gttgaagcgt tacctgttag gtaacgtagt    6420
tgagctgtaa aaaaatttt tatcacattt agttgagctg tcacagaatg tgacgttgaa    6480
gaatgtgatg ggatactgca ggtacggcca gttttttcttc ttcaccggca cgttgaagcg    6540
ttacctgtta ggtaacgtag ttgagctgtg ccggtgatttt tttttatgttg tagttgagct    6600 gtcacagaat gtgacgttga agcaacataa taaagcgaag ataattgcac gtgatgatgg    6660
catcggaagt acgttgaagc gttacctgtt aggtaacgta gttgagctgt acttccgatt    6720
tttcgccctg gtagttgagc tgtcacagaa tgtgacgttg aagccagggc gccggaagca    6780
agctaacttt tttttttttca cattaagtgt ttttttttg actccaacgt acgttgaagc    6840
gttacctgtt aggtaacgta gttgagctgt acgttggatt ttttgaaaaa atagttgagc    6900
tgtcacagaa tgtgacgttg aagttttttc aatcgttgta ccaacctaat ttttttttta    6960
acatcgccat taagattttc gagcggacgt tgaagcgtta cctgttaggt aacgtagttg    7020
agctgtccgc tcgatttta tgaccaatag ttgagctgtc acagaatgtg acgttgaagt    7080
tggtcatagc tgtttcctgt gtgaaaagcc tgttttaacc atacgttgaa gcgttacctg    7140
```

```
ttaggtaacg tagttgagct gtatggttaa ttttttgctt atatagttga gctgtcacag    7200
aatgtgacgt tgaagtataa gcaaaagggg aagccttttt ttaatatttc aatcatatgc    7260
gggacgttga agcgttacct gttaggtaac gtagttgagc tgtcccgcat attttttatt    7320
ttgttagttg agctgtcaca gaatgtgacg ttgaagacaa aataatatac gagcgtacta    7380 tggtttttt ttttttgcttt tgacgctttt tacgttgaag cgttacctgt taggtaacgt    7440
agttgagctg taaaaagcgc attaagcgcg gcgggtgtgg tggttacgcg cagcgtgacc    7500
gctacacttg ccagcgccct agcgcccgct cctttcgctt tcttcccttc ctttctcgcc    7560
acgttcgccg gctttccccg tcaagctcta atcggggggc tccctttagg gttccgattt    7620
agtgctttac ggcacctcga ccccaaaaaa cttgattagg gtgatggttc acgtagtggg    7680
ccatcgccct gatagacggt ttttcgccct ttgacgttgg agtccacgtt ctttaatagt    7740
ggactcttgt tccaaactgg aacaacactc aaccctatct cggtctattc ttttgattta    7800
taagggattt tgccgatttc ggcctattgg ttaaaaaatg agctgattta acaaaaattt    7860
aacgcgaatt ttaacaaaat attaacgctt acaatttagg tggcacttt cggggaaatg    7920 tgcgcggaac ccctatttgt ttatttttct aaatacattc aaatatgtat ccgctcatga    7980
gacaataacc ctgataaatg cttcaataat attgaaaaag gaagagt                8027

<210> SEQ ID NO 32
<211> LENGTH: 7899
<212> TYPE: DNA
<213> ORGANISM: Artificial Sequence
<220> FEATURE:
<223> OTHER INFORMATION: Phagemid pointer - part 2

<400> SEQUENCE: 32
atgagtattc aacatttccg tgtcgccctt attcccttt ttgcggcatt ttgccttcct      60 gttttgctc acccagaaac gctggtgaaa gtaaagatg ctgaagatca gttgggtgca     120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga ccacacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta actgtcagac caagtttact catatatact ttagattgat    900
ttaaaacttc atttttaatt taaaaggatc taggtgaaga tcctttttga taatctcatg    960
accaaaatcc cttaacgtga gttttcgttc cactgagcgt cagaccccgt agaaaagatc    1020
aaaggatctt cttgagatcc ttttttttctg cgcgtaatct gctgcttgca acaaaaaaaa    1080
ccaccgctac cagcggtggt ttgtttgccg gatcaagagc taccaactct ttttccgaag    1140
gtaactggct tcagcagagc gcagatacca aatactgtcc ttctagtgta gccgtagtta    1200
```

```
ggccaccact tcaagaactc tgtagcaccg cctacatacc tcgctctgct aatcctgtta   1260
ccagtggctg ctgccagtgg cgataagtcg tgtcttaccg ggttggactc aagacgatag   1320
ttaccggata aggcgcagcg gtcgggctga acgggggtt cgtgcacaca gcccagcttg    1380
gagcgaacga cctacaccga actgagatac ctacagcgtg agctatgaga aagcgccacg   1440
cttcccgaag ggagaaaggc ggacaggtat ccggtaagcg gcagggtcgg aacaggagag   1500
cgcacgaggg agcttccagg gggaaacgcc tggtatcttt atagtcctgt cgggtttcgc   1560
cacctctgac ttgagcgtcg attttttgtga tgctcgtcag ggggcggag cctatggaaa   1620 aacgccagca acgcggcctt tttacggttc ctggcctttt gctggccttt tgctcacggt   1680
gatggtagtt gagctgtcac agaatgtgac gttgaagcca tcaccaaaaa ctccgctcac   1740
aattccacac tttttttacg ttgaagcgtt acctgttagg taacgtagtt gagctgtaaa   1800
aaaagttttt ctgttggcta gttgagctgt cacagaatgt gacgttgaag gccaacagat   1860
acgtggtaat gccggggaag aaggacgttg aagcgttacc tgttaggtaa cgtagttgag   1920
ctgtccttct tcttttttact aatcgtagtt gagctgtcac agaatgtgac gttgaagcga   1980
ttagtcttta atttttttttt ttgcgcgaat atgataacgg aactgacgag aaacaccagt   2040
caataacgtt gaagcgttac ctgttaggta acgtagttga gctgttattg acttttttat   2100
aaatagtagt tgagctgtca cagaatgtga cgttgaagct atttatgtca atcccttctg   2160
aaacaagaga atcgatcctg agacgttgaa gcgttacctg ttaggtaacg tagttgagct   2220
gtctcaggat tttttttgatt tattagttga gctgtcacag aatgtgacgt tgaagataaa   2280
tcacagacac cacattcaac taatgatacg ttgaagcgtt acctgttagg taacgtagtt   2340
gagctgtatc attagttttt accaaaaata gttgagctgt cacagaatgt gacgttgaag   2400
tttttggtca ttggaattttt tttttcggt aatcgtaata ttttgtgcaa tgcttacgtt   2460
gaagcgttac ctgttaggta acgtagttga gctgtaagca ttgttttttt tgtagatagt   2520
tgagctgtca cagaatgtga cgttgaagtc tacaaaaaga actgttgtga attaccttat   2580
agaaattttt acgttgaagc gttacctgtt aggtaacgta gttgagctgt aaaaattttt   2640
tttttcaaaa atagttgagc tgtcacagaa tgtgacgttg aagtttttga atggctacca   2700
gtaaattggc agattcacca ttttttttttt gtcacaacgt tgaagcgtta cctgttaggt   2760
aacgtagttg agctgttgtg acaattttttt tgttctatag ttgagctgtc acagaatgtg   2820
acgttgaagt agaacaatta cataacaaac aatcataata gtaccgacaa aaacgttgaa   2880
gcgttacctg ttaggtaacg tagttgagct gttttttgtcg ttttttttttct cattagttga   2940 gctgtcacag aatgtgacgt tgaagatgag aaaggtaaat tgaaatctac aaaagaagag   3000
caacactatc atacgttgaa gcgttacctg ttaggtaacg tagttgagct gtatgatagt   3060 ttttttctcac atatagttga gctgtcacag aatgtgacgt tgaagtatgt gagtgaagtt   3120
acaagccaac gatttaacat aaattgtaaa cgttgaagcg ttacctgtta ggtaacgtag   3180
ttgagctgtt tacaattttt ttaaataatt tagttgagct gtcacagaat gtgacgttga   3240
agaattattt tttttttttaaa ttcgcatttc ggattcacag gcaatagcat taggacgttg   3300
aagcgttacc tgttaggtaa cgtagttgag ctgtcctaat gcttttttatt aaatttagtt   3360 gagctgtcac agaatgtgac gttgaagaat ttaatcagct cattaaatgt ttaataaata   3420
taaaggaata cgttgaagcg ttacctgtta ggtaacgtag ttgagctgta ttccttttt    3480 ttttaaaaaa tagttgagct gtcacagaat gtgacgttga agtttttttaa atcattcctt   3540
```

```
tttttttttgt gggaacaaac tcaggaaaat agtagtgaaa acgttgaag cgttacctgt      3600 taggtaacgt agttgagctg tttttcactt ttttcagggt actagttgag ctgtcacaga      3660
atgtgacgtt gaaggtaccc tgaaagaggt ctaaaccaat tattttttt ttaatcaaga       3720 tacgttgaag cgttacctgt taggtaacgt agttgagctg tatcttgatt ttttctacca      3780
tttagttgag ctgtcacaga atgtgacgtt gaagaatggt agcgccatat cgtaacagaa     3840
tcagcacgta aagacgttg aagcgttacc tgttaggtaa cgtagttgag ctgtcttata      3900 cgttttttaag tctattagtt gagctgtcac agaatgtgac gttgaagata gacttcaacc    3960
agaccaccgc gcctccggta tctaacgagc gtctacgttg aagcgttacc tgttaggtaa    4020
cgtagttgag ctgtagacgc tctttttttca tgttgtagtt gagctgtcac agaatgtgac    4080
gttgaagcaa catgaggcgg tgaccgtaag cgagtaccac caacgttgaa gcgttacctg    4140
ttaggtaacg tagttgagct gttggtggta tttttatctg ctgtagttga gctgtcacag    4200
aatgtgacgt tgaagcagca gattatcaaa aacagatagg cagattatac aagacctaaa    4260
ctatatgtat caatagacgt tgaagcgtta cctgttaggt aacgtagttg agctgtctat    4320
tgatttttta atatttgtag ttgagctgtc acagaatgtg acgttgaagc aaatattttt    4380
ttttttttca aaccctcaat catgctgaac accagaagag gtttaaatac gttgaagcgt    4440
tacctgttag gtaacgtagt tgagctgtat ttaaactttt ttttctctttt agttgagctg    4500 tcacagaatg tgacgttgaa gaaagagaac aatgttggga accatcacgg attaaagttg    4560
cagcattttt acgttgaagc gttacctgtt aggtaacgta gttgagctgt aaaaatgctt    4620
tttaaaaaaa ttagttgagc tgtcacagaa tgtgacgttg aagattttt tttttttaaa     4680 tatgcttttt ttttaacta aagggattttt ttttttgtg ctgcaagacg ttgaagcgtt       4740
acctgttagg taacgtagtt gagctgtctt gcagcttttt aagagcaata gttgagctgt     4800
cacagaatgt gacgttgaag ttgctcttca ttcccatttg ggcggcaccg cgacgacagt    4860
aaaacgcgac gttgaagcgt tacctgttag gtaacgtagt tgagctgtcg cgttttttt    4920 ttctattgat agttgagctg tcacagaatg tgacgttgaa gtcaatagat aataaaggct    4980
tacaatagca gcgaataaac agcttgataa taagtaacgt tgaagcgtta cctgttaggt    5040
aacgtagttg agctgttact tattttttg actcaaatag ttgagctgtc acagaatgtg    5100
acgttgaagt ttgagtcgag cttcaaagcg aaatatcgcc tgaggctact aaagaagacg    5160
ttgaagcgtt acctgttagg taacgtagtt gagctgtctt ctttattttt aaaaagtta     5220 gttgagctgt cacagaatgt gacgttgaag aacttttttt tttaattcga caacttttaa    5280
aacatcgcac gttgaagcgt tacctgttag gtaacgtagt tgagctgtgc gatgtttttt   5340
tgctttgatt agttgagctg tcacagaatg tgacgttgaa gatcaaagcg gtatatttta    5400
tataacacct cttcgctatc ggccttgcct acgttgaagc gttacctgtt aggtaacgta   5460
gttgagctgt aggcaaggtt ttttcaaagt ttagttgagc tgtcacagaa tgtgacgttg    5520
aagaactttg aggtgcaggg atttcttaat aattttttaaa gtcagattta tacgttgaag   5580
cgttacctgt taggtaacgt agttgagctg tataaatctt ttttttttaaa aatagttgag   5640 ctgtcacaga atgtgacgtt gaagttttta aaatcaggtc tttggcatca ttttttttt    5700 attctactga tttttttttt tcgcactcca acgttgaagc gttacctgtt aggtaacgta    5760
gttgagctgt ggagtgctt tttgtttcgg gtagttgagc tgtcacagaa tgtgacgttg    5820
aagcccgaaa catttcggta gatttgcgca actattaccg ctagcaatac tacgttgaag   5880
cgttacctgt taggtaacgt agttgagctg tagtattgct ttttaacgtt cgtagttgag   5940
```

```
ctgtcacaga atgtgacgtt gaagcgaacg ttattaatcg tattataaac aactgaattt    6000
tgtcgtcttt ccagacgacg ttgaagcgtt acctgttagg taacgtagtt gagctgtcgc    6060
ctggattttt aaaaaaaata gttgagctgt cacagaatgt gacgttgaag ttttttttt    6120 tttgagtaac atttaccttt tgaggcgacg ttgaagcgtt acctgttagg taacgtagtt    6180
gagctgtcgc ctcaattttt ccgaataata gttgagctgt cacagaatgt gacgttgaag    6240
ttattcggaa acagttagat taagacgctg ttatataatt taatgtggac gttgaagcgt    6300
tacctgttag gtaacgtagt tgagctgtcc ccattatttt tacacccttt agttgagctg    6360
tcacagaatg tgacgttgaa gaagggtgtt tggatataga taaatttacg agcatgtttt    6420
tttttttaga aaccaatcaa cgggtatacg ttgaagcgtt acctgttagg taacgtagtt    6480
gagctgtata cccgtttttt tggatatgta gttgagctgt cacagaatgt gacgttgaag    6540
catatccaaa agaaattagc aacgcaagga gttaaatcta aattacgttg aagcgttacc    6600
tgttaggtaa cgtagttgag ctgtaattta gattttttaaa atgattagtt gagctgtcac    6660
agaatgtgac gttgaagatc atttttttcc attacgcata acgacaatgt agaaaggaga    6720
cgttgaagcg ttacctgtta ggtaacgtag ttgagctgtc tccttcttt ttaaaaatgt    6780 tagttgagct gtcacagaat gtgacgttga agacattttt ttttttcggg agaaactcat    6840
taccgtaatc ttgacaagaa ctgaccttgt acagacgttg aagcgttacc tgttaggtaa    6900
cgtagttgag ctgtctgtac aatttttatc tcaagtagtt gagctgtcac agaatgtgac    6960
gttgaagctt gagatggttt aaattacctt atttcaaaat taagctaacg ttgaagcgtt    7020
acctgttagg taacgtagtt gagctgttag cttaatttt cgtaaaaata gttgagctgt    7080
cacagaatgt gacgttgaag ttttacgag acaaaattcc tcatatttt ttttttattt    7140 taacgttgaa gcgttacctg ttaggtaacg tagttgagct gttaaaataa tttttctcgt    7200
ttttagttga gctgtcacag aatgtgacgt tgaagaaaac gagtagccgg agagttctag    7260
cgaaaagcct aaagggaca ttctacgttg aagcgttacc tgttaggtaa cgtagttgag    7320
ctgtagaatg tcattaagcg cggcgggtgt ggtggttacg cgcagcgtga ccgctacact    7380
tgccagcgcc ctagcgcccg ctcctttcgc tttcttccct ccttctcg ccacgttcgc    7440 cggctttccc cgtcaagctc taaatcgggg gctcccttta gggttccgat ttagtgcttt    7500
acggcacctc gaccccaaaa aacttgatta gggtgatggt tcacgtagtg gccatcgcc    7560 ctgatagacg ttttcgcc ctttgacgtt ggagtccacg ttctttaata gtggactctt    7620
gttccaaact ggaacaacac tcaaccctat ctcggtctat tcttttgatt tataagggat    7680
tttgccgatt tcggcctatt ggttaaaaaa tgagctgatt taacaaaaat ttaacgcgaa    7740
ttttaacaaa atattaacgc ttacaattta ggtggcactt ttcgggggaaa tgtgcgcgga    7800 acccctattt gttattttt ctaaatacat tcaaatatgt atccgctcat gagacaataa    7860
ccctgataaa tgcttcaata atattgaaaa aggaagagt                          7899
```

<210> SEQ ID NO 33
<211> LENGTH: 8036
<212> TYPE: DNA
<213> ORGANISM: Artificial Sequence
<220> FEATURE:
<223> OTHER INFORMATION: Phagemid pointer - part 3

<400> SEQUENCE: 33

```
atgagtattc aacatttccg tgtcgccctt attcccttt ttgcggcatt ttgccttcct    60
```

-continued

```
gttttttgctc acccagaaac gctggtgaaa gtaaagatg  ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga tataggtgcc    840
tcactgatta agcattggta actgtcagac caagtttact catatatact ttagattgat    900
ttaaaacttc attttttaatt taaaaggatc taggtgaaga tccttttttga taatctcatg    960 accaaaatcc cttaacgtga gttttcgttc cactgagcgt cagacccccgt agaaaagatc   1020 aaaggatctt cttgagatcc tttttttctg cgcgtaatct gctgcttgca acaaaaaaaa   1080
ccaccgctac cagcggtggt ttgtttgccg gatcaagagc taccaactct ttttccgaag   1140
gtaactggct tcagcagagc gcagatacca atactgtcc ttctagtgta gccgtagtta   1200
ggccaccact tcaagaactc tgtagcaccg cctacatacc tcgctctgct aatcctgtta   1260
ccagtggctg ctgccagtgg cgataagtcg tgtcttaccg ggttggactc aagacgatag   1320
ttaccggata aggcgcagcg gtcgggctga acggggggtt cgtgcacaca gcccagcttg   1380
gagcgaacga cctacaccga actgagatac ctacagcgtg agctatgaga aagcgccacg   1440
cttcccgaag ggagaaaggc ggacaggtat ccggtaagcg cagggtcgg  aacaggagag   1500 cgcacgaggg agcttccagg gggaaacgcc tggtatcttt atagtcctgt cgggtttcgc   1560
cacctctgac ttgagcgtcg attttttgtga tgctcgtcag gggggcggag cctatggaaa   1620
aacgccagca acgcggcctt tttacggttc ctggcctttt gctggccttt tgctcacggg   1680
tcatatagtt gagctgtcac agaatgtgac gttgaagtat gaccctgaaa tcggtctggc   1740
cttacctaca tttgacgaga gcgggagcta ttttttacgtt gaagcgttac ctgttaggta   1800
acgtagttga gctgtaaaaa tagttttttga aggttatagt tgagctgtca cagaatgtga   1860
cgttgaagta accttcccctt agaatccttg ccaatcgcat attttaagta ccacgttgaa   1920
gcgttacctg ttaggtaacg tagttgagct gtggtactta tttttggacg atttagttga   1980
gctgtcacag aatgtgacgt tgaagaatcg tccggatata ataacggact gaccagacgg   2040
tcagttacta cgttgaagcg ttacctgtta ggtaacgtag ttgagctgta gtaactgttt   2100
ttaaaaattg tagttgagct gtcacagaat gtgacgttga agcaattttt tttttatcaa   2160
cgtaacaaag ctgctcattc agtaacgttg aagcgttacc tgttaggtaa cgtagttgag   2220
ctgttactga attttttgtt taaagtagtt gagctgtcac agaatgtgac gttgaagctt   2280 taaactttttt tttttagttc gcgattttgg ctatcatttt tacgttgaag cgttacctgt   2340
taggtaacgt agttgagctg taaaaatgat ttttgttggc gttagttgag ctgtcacaga   2400
atgtgacgtt gaagacgcca acctgaaagc gtaagaagat agaacatatg taccccggtt   2460
```

```
tgacgttgaa gcgttacctg ttaggtaacg tagttgagct gtcaaaccgg ttttcctaa    2520
aaatagttga gctgtcacag aatgtgacgt tgaagttttt aggtagaaag attcatcagt   2580
accagacgac gatttttttt tttaaaaaca cgttgaagcg ttacctgtta ggtaacgtag   2640
ttgagctgtg ttttaatt ttctattttg tagttgagct gtcacagaat gtgacgttga    2700
agcaaaatag cgagaggctt ttgcgttaat aataggaata ataacgttga agcgttacct   2760
gttaggtaac gtagttgagc tgttattatt cttttccag tcgatagttg agctgtcaca   2820
gaatgtgacg ttgaagtcga ctggatagcg tccatttttt ttttatactg cgaaatgacg   2880
ttgaagcgtt acctgttagg taacgtagtt gagctgtcat ttcgcttttt gcctcgtata   2940
gttgagctgt cacagaatgt gacgttgaag tacgaggcca gatacaagga cgttgagagg   3000
gttaaagatt caaatattag ctcattgctg gcacgttgaa gcgttacctg ttaggtaacg   3060
tagttgagct gtgccagcaa ttttaaaac ttatagttga gctgtcacag aatgtgacgt   3120
tgaagtaagt tttgccagag ggggtaatag taataccagt ctaacgttga agcgttacct   3180
gttaggtaac gtagttgagc tgttagactg gttttcgag ggtttagttg agctgtcaca   3240
gaatgtgacg ttgaagaacc ctcgttttga gattaacgaa ctattcaacc cagtcaaatt   3300
atttacgttg aagcgttacc tgttaggtaa cgtagttgag ctgtaaataa tttttttttg   3360
ataaatagtt gagctgtcac agaatgtgac gttgaagttt atcaaaatca taggtctttt   3420
ttttttgag agactaccta aaggacgtt gaagcgttac ctgttaggta acgtagttga   3480
gctgtcctta tagtttttta ctaaaatagt tgagctgtca cagaatgtga cgttgaagtt   3540
ttagtattac ctgagaaaat tataacagag ggtgccacgt gagggacgtt gaagcgttac   3600
ctgttaggta acgtagttga gctgtccctc acgttttttg tatgtttagt tgagctgtca   3660
cagaatgtga cgttgaagaa catacagtat aaaaatcgcg aattgcgtaa ataccatct   3720
aaagatggaa attcgccaac gttgaagcgt tacctgttag gtaacgtagt tgagctgttg   3780
gcgaattttt tcaaaattat agttgagctg tcacagaatg tgacgttgaa gtaattttgc   3840
ttctgtgaat aaggcttgcc caacattatt acttttacg ttgaagcgtt acctgttagg   3900
taacgtagtt gagctgtaaa aagtattttt atcgcgttta gttgagctgt cacagaatgt   3960
gacgttgaag aacgcgatag gctggcgcta ttaggaaccg aattcgcctg aatatacagt   4020
aacacgttga agcgttacct gttaggtaac gtagttgagc tgtgttactg tttttttgcg   4080
ttcgtagttg agctgtcaca gaatgtgacg ttgaagcgaa cgcaataagt tacctttggg   4140
aattagagcc ttagcgtttg ccattttac gttgaagcgt tacctgttag gtaacgtagt   4200
tgagctgtaa aaatggtttt tggctttcgt agttgagctg tcacagaatg tgacgttgaa   4260
gcgaaagcct gcaatagtgt tcatttgatt tcaactgtgt aggagacgtt gaagcgttac   4320
ctgttaggta acgtagttga gctgtctcct acattttat atcagttagt tgagctgtca   4380
cagaatgtga cgttgaagac tgatataagt atattttttt tttgcccgga ataggtaggc   4440
tgagttttta cgttgaagcg ttacctgtta ggtaacgtag ttgagctgta aaaactcttt   4500
ttttcttgat tagttgagct gtcacagaat gtgacgttga agatcaagaa aaatgatttt   4560
ttttttccat atgaataata catccaattt ttacgttgaa gcgttacctg ttaggtaacg   4620
tagttgagct gtaaaaattg tttttatta tattagttga gctgtcacag aatgtgacgt   4680
tgaagatata atactagaat gtgataattt taacccaaag acaaaatttt ttttttggga   4740
ccgacttgag ttttacgtt gaagcgttac ctgttaggta acgtagttga gctgtaaaaa   4800
```

```
ctctttttttt aaaatgtagt tgagctgtca cagaatgtga cgttgaagca tttaaagta      4860 cacagcgatt cccatgtata ccgaagccct ttttgaacgt tgaagcgtta cctgttaggt      4920
aacgtagttg agctgttcaa aaagttttta ttaattatag ttgagctgtc acagaatgtg      4980
acgttgaagt aattaataaa gacagaggcg ataaagctta atacttcgac gttgaagcgt      5040
tacctgttag gtaacgtagt tgagctgtcg aagtatttt tagatggcgt agttgagctg       5100
tcacagaatg tgacgttgaa gcgccatctc aacagtttca aataagacaa aaagacacca     5160
cggaataata cgttgaagcg ttacctgtta ggtaacgtag ttgagctgta ttattccttt      5220
ttcaaagttg tagttgagct gtcacagaat gtgacgttga agcaactttg aaagaggttt      5280 ttttttaca gatgaacggt catcaagaac gttgaagcgt tacctgttag gtaacgtagt       5340
tgagctgttc ttgatgtttt ttactttact agttgagctg tcacagaatg tgacgttgaa     5400
ggtaaagtaa ttcgctaatg cagaacgcgc ctttttttt  ttgtttatca acatatactt      5460
caatcatttt tacgttgaag cgttacctgt taggtaacgt agttgagctg taaaaatgat      5520
ttttcttcgt tatagttgag ctgtcacaga atgtgacgtt gaagtaacga aggcacagcc     5580
ctcatagttt ttttttttta gccccacaag acgttgaagc gttacctgtt aggtaacgta     5640
gttgagctgt cttgtgggtt ttttacgtat ttagttgagc tgtcacagaa tgtgacgttg     5700
aagaatacgt acaaacagca agaaacaatg aaccctgaac tcacgttgta acgttgaagc    5760
gttacctgtt aggtaacgta gttgagctgt tacaacgttt tttcgacttg ctagttgagc     5820
tgtcacagaa tgtgacgttg aaggcaagtc gaaatgaggt ttagcggata atagcggggg    5880
aaacgcaacg ttgaagcgtt acctgttagg taacgtagtt gagctgttgc gtttcttttt      5940
agttcgttta gttgagctgt cacagaatgt gacgttgaag aacgaacttt ttcaaattga     6000
gacgtcagat gattgctttg aataccaaac gttgaagcgt tacctgttag gtaacgtagt     6060
tgagctgttt ggtatttttt taacatgttt agttgagctg tcacagaatg tgacgttgaa     6120
gaacatgttc atgtccagac tcattttaat aacggtcacc gtccgacatt cacgttgaag    6180
cgttacctgt taggtaacgt agttgagctg tgaatgtcgt tttacaggg tgtagttgag      6240 ctgtcacaga atgtgacgtt gaagcaccct gtatcggtag gctccattag acggtgttta     6300
acgtcaaaaa tgacgttgaa gcgttacctg ttaggtaacg tagttgagct gtcattttg      6360 tttttcgga tcctagttga gctgtcacag aatgtgacgt tgaagggatc cgagggatt       6420 gaccccacgg agatccctca acgttgaagc gttacctgtt aggtaacgta gttgagctgt     6480
tgagggattt tttctcttaa atagttgagc tgtcacagaa tgtgacgttg aagtttaaga    6540
ggaatattcc taatgaaaag aacgaacatg ggcgccctgt aacgttgaag cgttacctgt     6600
taggtaacgt agttgagctg ttacagggct ttttatctat attagttgag ctgtcacaga     6660
atgtgacgtt gaagatatag attttgcaat cctttgattt agaagtatta gactttacat    6720
tagtaacgtt gaagcgttac ctgttaggta acgtagttga ctgttacta atgttttcc       6780 gtttggtagt tgagctgtca cagaatgtga cgttgaagcc aaacgggtaa aatttttttt     6840
tttacgtaat gccactgccg gaacacgttg aagcgttacc tgttaggtaa cgtagttgag     6900
ctgtgttccg gctttttaac ttcactagtt gagctgtcac agaatgtgac gttgaaggtg    6960
aagttaaagg gaatcattgg aagcaagatt agagaatcaa cagttacgtt gaagcgttac     7020
ctgttaggta acgtagttga gctgtaactg ttgtttttaa ggtacgtagt tgagctgtca    7080
cagaatgtga cgttgaagcg taccttttga aatattctaa atataatgct gaactcaaac    7140
tacgttgaag cgttacctgt taggtaacgt agttgagctg tagtttgagt ttttttcaac     7200
```

```
ggtagttgag ctgtcacaga atgtgacgtt gaagccgttg aacctcccag ctacaatttt      7260
atccgatttt tgagaattaa cacgttgaag cgttacctgt taggtaacgt agttgagctg      7320
tgttaattct ttttacggc tttagttgag ctgtcacaga atgtgacgtt gaagaagccg       7380
taccgcattc aagaataat cggtaagcag atagccttt tacgttgaag cgttacctgt        7440
taggtaacgt agttgagctg taaaaaggca ttaagcgcgg cgggtgtggt ggttacgcgc      7500
agcgtgaccg ctacacttgc cagcgccta gcgcccgctc ctttcgcttt cttcccttcc       7560
tttctcgcca cgttcgccgg ctttccccgt caagctctaa atcggggct ccctttaggg       7620 ttccgattta gtgctttacg gcacctcgac cccaaaaaac ttgattaggg tgatggttca      7680
cgtagtgggc catcgccctg atagacggtt tttcgccctt gacgttgga gtccacgttc       7740 tttaatagtg actcttgtt ccaaactgga acaacactca accctatctc ggtctattct       7800
tttgatttat aagggatttt gccgatttcg gcctattggt taaaaaatga gctgatttaa      7860 caaaattta acgcgaattt taacaaaata ttaacgctta caatttaggt ggcacttttc       7920
ggggaaatgt gcgcggaacc cctatttgtt tatttttcta aatacattca aatatgtatc      7980
cgctcatgag acaataaccc tgataaatgc ttcaataata ttgaaaaagg aagagt         8036
```

<210> SEQ ID NO 34
<211> LENGTH: 7904
<212> TYPE: DNA
<213> ORGANISM: Artificial Sequence
<220> FEATURE:
<223> OTHER INFORMATION: Phagemid pointer - part 4

<400> SEQUENCE: 34

```
atgagtattc aacatttccg tgtcgcccct attcccttt ttgcggcatt ttgccttcct        60 gttttgctc acccagaaac gctggtgaaa gtaaagatg ctgaagatca gttgggtgca       120
cgagtgggtt acatcgaact ggatctcaac agcggtaaga tccttgagag ttttcgcccc      180
gaagaacgtt ttccaatgat gagcactttt aaagttctgc tatgtggcgc ggtattatcc     240
cgtattgacg ccgggcaaga gcaactcggt cgccgcatac actattctca gaatgacttg     300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt     480
gatcgttggg aaccggagct gaatgaagcc ataccaaacg acgagcgtga ccacacgatg     540
cctgtagcaa tggcaacaac gttgcgcaaa ctattaactg gcgaactact tactctagct     600
tcccggcaac aattaataga ctggatggag gcggataaag ttgcaggacc acttctgcgc    660
tcggcccttc cggctggctg gtttattgct gataaatctg gagccggtga gcgtgggtct     720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta actgtcagac caagtttact catatatact ttagattgat     900
ttaaaacttc atttttaatt taaaaggatc taggtgaaga tccttttttga atctcatg     960 accaaaatcc cttaacgtga gttttcgttc cactgagcgt cagaccccgt agaaaagatc    1020
aaaggatctt cttgagatcc ttttttttctg cgcgtaatct gctgcttgca acaaaaaaa    1080 ccaccgctac cagcggtggt ttgtttgccg gatcaagagc taccaactct ttttccgaag    1140
gtaactggct tcagcagagc gcagatacca atactgtcc ttctagtgta gccgtagtta     1200
```

```
ggccaccact tcaagaactc tgtagcaccg cctacatacc tcgctctgct aatcctgtta    1260
ccagtggctg ctgccagtgg cgataagtcg tgtcttaccg ggttggactc aagacgatag    1320
ttaccggata aggcgcagcg gtcgggctga acgggggtt cgtgcacaca gcccagcttg     1380
gagcgaacga cctacaccga actgagatac ctacagcgtg agctatgaga aagcgccacg    1440
cttcccgaag ggagaaaggc ggacaggtat ccggtaagcg gcagggtcgg aacaggagag    1500
cgcacgaggg agcttccagg gggaaacgcc tggtatcttt atagtcctgt cgggtttcgc    1560
cacctctgac ttgagcgtcg atttttgtga tgctcgtcag gggggcggag cctatggaaa    1620
aacgccagca acgcggcctt tttacggttc ctggcctttt gctggccttt tgctcacaaa    1680
taaagtagtt gagctgtcac agaatgtgac gttgaagctt tattttcaaa aaaattatca    1740
gcagctatct ccgtaacact gagtacgttg aagcgttacc tgttaggtaa cgtagttgag    1800
ctgtactcag tgtttttttg aaatttagtt gagctgtcac agaatgtgac gttgaagaat    1860
ttcaacagtt tcttttttttt ttagcggagt gagaaacaac aacacgttga agcgttacct    1920
gttaggtaac gtagttgagc tgtgttgttg tttttggct gctatagttg agctgtcaca     1980
gaatgtgacg ttgaagtagc agcctttaca gttttttttt tagagaataa cataacgttg    2040
aagcgttacc tgttaggtaa cgtagttgag ctgttatgtt attttttgac gttggtagtt    2100
gagctgtcac agaatgtgac gttgaagcca acgtctaaga acgcgaggca actaataact    2160
ccaacgcgaa cgacaacgtt gaagcgttac ctgttaggta acgtagttga gctgttgtcg    2220
ttctttttat ggcgaatagt tgagctgtca cagaatgtga cgttgaagtt cgccatatta    2280
gggtaattga gcgcttaagc ccaataccga taaacgttga agcgttacct gttaggtaac    2340
gtagttgagc tgtttatcgg ttttttacta ttttagttg agctgtcaca gaatgtgacg     2400
ttgaagaaaa tagttgctat ccttatcact catcgaataa tatcgtcaga agcaatataa    2460
ctacgttgaa gcgttacctg ttaggtaacg tagttgagct gtagttatat tttttggatt    2520
gggtagttga gctgtcacag aatgtgacgt tgaagcccaa tccaaataag aaactgaatc    2580
taaaatctcc atcgtagccg cttacgttga agcgttacct gttaggtaac gtagttgagc    2640
tgtaagcggc ttttttgctc tgtgtagttg agctgtcaca gaatgtgacg ttgaagcaca    2700
gagcctaagg aattagcaaa tcttcggtcg gttttaataa gaaaccctac gttgaagcgt    2760
tacctgttag gtaacgtagt tgagctgtag ggtttctttt tcctgttttt agttgagctg    2820
tcacagaatg tgacgttgaa gaaaacagga agaaaagctg tctttataaa caacaagaaa    2880
ataataagaa cacgttgaag cgttacctgt taggtaacgt agttgagctg tgttcttatt    2940
ttttcttttg cgtagttgag ctgtcacaga atgtgacgtt gaagcgcaaa aggagctttg    3000
cacccgactt gcgggaggtt ttaattgcaa acgttgaagc gttacctgtt aggtaacgta    3060
gttgagctgt ttgcaatttt tttattgttc atagttgagc tgtcacagaa tgtgacgttg    3120
aagtgaacaa tagcaatttg ctttcactca tctgcaacgg catacgttga agcgttacct    3180
gttaggtaac gtagttgagc tgtatgccgt tttttttac ttattagttg agctgtcaca     3240
gaatgtgacg ttgaagataa gtaactttt ttttgatct aaagttttag ttacaaaata      3300
aaacgttgaa gcgttacctg ttaggtaacg tagttgagct gttttatttt tttttactca    3360
atttagttga gctgtcacag aatgtgacgt tgaagaattg agtaatatca gaacaactaa    3420
atttgccctg tatggagata tagcaacgtt gaagcgttac ctgttaggta acgtagttga    3480
gctgttgcta tattttttttt caaaaatagt tgagctgtca cagaatgtga cgttgaagtt    3540
tttgaacaca gggatagcaa gcccccacca cccgacgaca accgacacgt tgaagcgtta    3600
```

```
cctgttaggt aacgtagttg agctgtgtcg gttgtttttg cggttaatag ttgagctgtc    3660
acagaatgtg acgttgaagt taaccgccat tgtatcacat cttctattct tacgcgatag    3720
ctacataacg ttgaagcgtt acctgttagg taacgtagtt gagctgttat gtagcttttt    3780
aggcgttgta gttgagctgt cacagaatgt gacgttgaag caacgccgtgt agcagtactc   3840 agccgcgacc gaaaacttta gggcttatac gttgaagcgt tacctgttag gtaacgtagt    3900
tgagctgtat aagccctttt tagtcttatt agttgagctg tcacagaatg tgacgttgaa    3960
gataagactc atagacggat attcatgagc cgccgccagc atcgcctcac gttgaagcgt    4020
tacctgttag gtaacgtagt tgagctgtga ggcgatttttt tgtatcatgt agttgagctg   4080
tcacagaatg tgacgttgaa gcatgatacc gccacgcacc attaccatta gtttcatcgt    4140
aaacagtgta cgttgaagcg ttacctgtta ggtaacgtag ttgagctgta cactgttttt    4200
ttggcggtac tagttgagct gtcacagaat gtgacgttga aggtaccgcc accaatgaaa    4260
ccatcgaagt ttgccctatt acgttgaagc gttacctgtt aggtaacgta gttgagctgt    4320
aatagggctt tttctcgacg gtagttgagc tgtcacagaa tgtgacgttg aagccgtcga    4380
gagggtcagg cgcatgctcc atatcataag tgaggaaggc ggaacagcca cgttgaagcg    4440
ttacctgtta ggtaacgtag ttgagctgtg gctgttcttt ttagtaaaaa tagttgagct    4500
gtcacagaat gtgacgttga agtttttact cctcaatttt tttttttaa gcagtagcga     4560 cagaatcata gcagcattag gatgtacgtt gaagcgttac ctgttaggta acgtagttga    4620
gctgtacatc ctatttttg gaaaaatagt tgagctgtca cagaatgtga cgttgaagtt     4680
tttccaagaa ggaatttttt ttttaccgag gattaaataa gaattttttt ttttaaacac    4740
cgacgttgaa gcgttacctg ttaggtaacg tagttgagct gtcggtgttt tttttattca    4800
cattagttga gctgtcacag aatgtgacgt tgaagatgtg aattaaatac ccaaccagcg    4860
ctccggctta ggttgggaga agaacgttga agcgttacct gttaggtaac gtagttgagc    4920
tgttcttctc cttttttctga ggtatagttg agctgtcaca gaatgtgacg ttgaagtacc   4980
tcagagaata ggaaatacca agctttaatt cagcagcgga acaaacgttg aagcgttacc    5040
tgttaggtaa cgtagttgag ctgtttgttc cgttttttggc cttgatagtt gagctgtcac   5100
agaatgtgac gttgaagtca aggccgcgta gaaacttatt acttgtcaca aaatgctgat    5160
gcaaataaac gttgaagcgt tacctgttag gtaacgtagt tgagctgttt atttgctttt    5220 tagaaaaat agttgagctg tcacagaatg tgacgttgaa gttttttctt ttcataatcc     5280
cttgatattt ttttttttc acaaacaaat aacgttgaag cgttacctgt taggtaacg      5340 agttgagctg ttatttgttt tttaataggg catagttgag ctgtcacaga atgtgacgtt    5400
gaagtgccta ttagcaaaga aacgtcaccc tcagcgtcac caactaaaac gaacgttgaa    5460
gcgttacctg ttaggtaacg tagttgagct gttcgtttta ttttacact cattagttga     5520 gctgtcacag aatgtgacgt tgaagatgag tgtacagagc cactttttt ttcaccctc      5580 agagccgacg ttgaagcgtt acctgttagg taacgtagtt gagctgtcgg ctctgttttt    5640
ctctacttta gttgagctgt cacagaatgt gacgttgaag aagtagagaa ggaccgtaat    5700 gtatcaccctt ccacagacca acctagttgc gcccacgttg aagcgttacc tgttaggtaa   5760
cgtagttgag ctgtgggcgc aattttttga caaggtagtt gagctgtcac agaatgtgac    5820
gttgaagcct tgtcagagcc gccaccctca gaaccgacca gaacccacgt tgaagcgtta    5880
cctgttaggt aacgtagttg agctgtgggt tctgttttta atcgttttag ttgagctgtc    5940
```

```
acagaatgtg acgttgaaga aacgattgga aaatcacggt tgaggaaccg attgagggag    6000
gtatggtacg ttgaagcgtt acctgttagg taacgtagtt gagctgtacc ataccttttt    6060
tgcgctttta gttgagctgt cacagaatgt gacgttgaag aaagcgcagt ccggggtcat    6120
aatgccccac caccaacata aaggtggcaa cgttgaagcg ttacctgtta ggtaacgtag    6180
ttgagctgtt gccacctttt ttcatgtatg tagttgagct gtcacagaat gtgacgttga    6240
agcatacatg gcttttttt ttttttgatg atacagtctg aaacatgaac gttgaagcgt    6300
tacctgttag gtaacgtagt tgagctgttc atgttttttt tgggtggggt agttgagctg    6360
tcacagaatg tgacgttgaa gccccaccct ctggtaataa gttttaatct gaatttcaga    6420
ctgtagcgca cgttgaagcg ttacctgtta ggtaacgtag ttgagctgtg cgctacattt    6480
ttctgacctg tagttgagct gtcacagaat gtgacgttga agcaggtcag accggaactg    6540
acaggacgga accacattaa agcaccagac gttgaagcgt tacctgttag gtaacgtagt    6600
tgagctgtct ggtgcttttt tgttactggt agttgagctg tcacagaatg tgacgttgaa    6660
gccagtaaca ggagccacct cctcattggt catagccccc ttaagcaaaa cgttgaagcg    6720
ttacctgtta ggtaacgtag ttgagctgtt ttgcttattt ttttctttaa tagttgagct    6780
gtcacagaat gtgacgttga agttaaagaa cttttgaaat cgcgaaaccg agccagaaag    6840
acagcaattc acgttgaagc gttacctgtt aggtaacgta gttgagctgt gaattgcttt    6900
ttttgaattt ttagttgagc tgtcacagaa tgtgacgtta agaaaattc agaaggtaaa    6960
aattatttgc ccgtagcatt ttcaaagcca gaatgacgtt gaagcgttac ctgttaggta    7020
acgtagttga gctgtcattc tggtttttta aactgttagt tgagctgtca cagaatgtga    7080
cgttgaagac agtttattgc agtatggtta attttcgcct gaacgccaac tacagaggtt    7140
atcatcagac gttgaagcgt tacctgttag gtaacgtagt tgagctgtct gatgattttt    7200
taattttatt agttgagctg tcacagaatg tgacgttgaa gataaaattt tgctctttcg    7260
gaacttttagc gtaccgttcc agtaagcgta cgttgaagcg ttacctgtta ggtaacgtag    7320
ttgagctgta cgcttacatt aagcgcggcg ggtgtggtgg ttacgcgcag cgtgaccgct    7380
acacttgcca gcgccctagc gcccgctcct ttcgctttct tcccttcctt tctcgccacg    7440
ttcgccggct ttccccgtca agctctaaat cgggggctcc ctttagggtt ccgatttagt    7500
gctttacggc acctcgaccc caaaaaactt gattagggtg atggttcacg tagtgggcca    7560
tcgccctgat agacggtttt tcgccctttg acgttggagt ccacgttctt taatagtgga    7620
ctcttgttcc aaactggaac aacactcaac cctatctcgg tctattcttt tgatttataa    7680
gggattttgc cgatttcggc ctattggtta aaaaatgagc tgatttaaca aaaatttaac    7740
gcgaatttta acaaaatatt aacgcttaca atttaggtgg cacttttcgg ggaaatgtgc    7800
gcggaacccc tatttgttta ttttttctaaa tacattcaaa tatgtatccg ctcatgagac    7860
aataaccctg ataaatgctt caataatatt gaaaaggaa gagt                      7904
```

<210> SEQ ID NO 35
<211> LENGTH: 58
<212> TYPE: DNA
<213> ORGANISM: Artificial sequence
<220> FEATURE:
<223> OTHER INFORMATION: DNAzyme oligonucleotide
<220> FEATURE:
<221> NAME/KEY: misc_feature
<222> LOCATION: (24)..(24)
<223> OTHER INFORMATION: n = G or A
<220> FEATURE:
<221> NAME/KEY: misc_feature

```
<222> LOCATION: (38)..(38)
<223> OTHER INFORMATION: n = C or T

<400> SEQUENCE: 35 tttttttgccc tgatagttga gctntcacag aatgtgangt tgaagtcagg gcataaat         58
```

US 11,913,050 B2

SCALABLE BIOTECHNOLOGICAL PRODUCTION OF DNA SINGLE STRAND MOLECULES OF DEFINED SEQUENCE AND LENGTH

CROSS REFERENCE TO RELATED APPLICATIONS

This application is a National Stage Application of International Application Number PCT/EP2017/068051, filed Jul. 17, 2017; which claims priority to European Patent Application No. 16189976.0, filed Sep. 21, 2016.

The Sequence Listing for this application is labeled "SeqList-16Mar22-ST25.txt", which was created on Mar. 16, 2022 and is 91,483 bytes. The entire content is incorporated herein by reference in its entirety.

The present invention relates to a method for the recombinant production of DNA single stranded molecules, comprising the steps of (1) providing a pseudogene nucleic acid; (2) integrating the pseudogene nucleic acid into a vector, transforming bacterial cells with said vector and producing a precursor ssDNA from said vector under bacterial culture conditions; (3) isolating the precursor ssDNA from the bacterial culture; (4) digesting the precursor ssDNA under reaction conditions where self-cleaving DNA sequences become active; and (5) separating and obtaining the target single stranded DNA oligo- or polynucleotide(s). The method of the present invention is suitable for the mass production of DNA single stranded molecules. The present invention further relates to the use of the target single stranded DNA oligo- or polynucleotide(s), in particular in DNA nanotechnology, or as research tools.

BACKGROUND OF THE INVENTION

DNA oligonucleotides are needed in the life sciences and medicine for a variety of applications. Oligonucleotides are, for example, required as primers for performing the polymerase chain reaction (PCR) or real-time PCR (RT-PCR) or quantitative PCR (Q-PCR), respectively. In addition, oligonucleotides are needed as starting materials for the synthesis of new genes. The increasing demand for DNA oligonucleotides led to an industry which mainly specializes on the fast production of DNA oligonucleotides of any desired sequence in smallest amounts. DNA oligonucleotides are typically produced base by base in a cyclic chemical synthesis process on a solid phase. This process can be carried out on microscopic beads or in an ink-jet method on a chip surface. Since the base addition reactions do not proceed with 100% efficiency, it is not possible to produce DNA single strands in any length. The yield decreases in an exponential manner with the desired length of the target DNA oligonucleotide. Typically, up to 100 bases long molecules can be produced with a justifiable effort. Some firms offer a (cost-intensive) synthesis of DNA oligonucleotides with a length of up to 200 bases. Furthermore, the synthesis of DNA oligonucleotides is typically limited to the milligram scale, which is sufficient for most of the applications hitherto.

At the moment, new technologies are developed which require single stranded DNA oligonucleotides with user-defined sequence in high amounts (> gram scale) and/or with greater lengths (>200 base length). This demand cannot be met by the existing processes for the synthesis of DNA oligonucleotides. In particular in the DNA nanotechnology, single stranded DNA oligonucleotides with user-defined sequences are needed in high amounts as "construction material". DNA nanotechnology promises a particular potential for the generation of new drug delivery vehicles and further nanoparticles with potential medical or even chemical/physical relevance (Jones et al., 2015). However, the starting materials needed (i.e. DNA oligonucleotides) are, at the moment, not available in a scalable manner. Furthermore, catalytically active DNA sequences (DNAzymes) and DNA aptamers attain an increasing interest with respect to applications as diagnostics, in therapy and sensing (Krug et al., 2015; Keefe et al., 2010; Ng et al., 2006; Torabi et al., 2015). For such applications a mass production of DNA oligonucleotides is of great interest.

SUMMARY OF THE INVENTION

According to the present invention this object is solved by a method for the recombinant production of DNA single stranded molecules, comprising the steps of
(1) providing a pseudogene nucleic acid,
  wherein said pseudogene nucleic acid is a nucleic acid that comprises at least one target DNA oligo- or polynucleotide sequence and two self-cleaving DNA sequences flanking each target DNA oligo- or polynucleotide sequence,
(2) integrating the pseudogene nucleic acid into a vector, transforming bacterial cells with said vector and producing a precursor ssDNA from said vector under bacterial culture conditions,
  wherein said precursor ssDNA comprises the pseudogene nucleic acid;
(3) isolating the precursor ssDNA from the bacterial culture;
(4) digesting the precursor ssDNA under reaction conditions where the self-cleaving DNA sequences become active;
and
(5) separating the target single stranded DNA oligo- or polynucleotide(s) and obtaining the target single stranded DNA oligo- or polynucleotide(s).

According to the present invention this object is solved by using the target single stranded DNA oligo- or polynucleotide(s) obtained in the method of the present invention
  in DNA nanotechnology,
  as research tools,
  as probes for diagnostics
  in gene synthesis,
  in gene therapy,
  in molecular sensing/as molecular sensors.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50 to 3,000 nucleotides" should be interpreted to include not only the explicitly recited values of 50 to 3,000, but also include individual values and sub-ranges within the indicated range. Thus, included in this numerical range are individual values such as 50, 51, 52 . . . 2,998, 2,999, 3,000 and sub-ranges such as from 50 to 150, from 100 to 250, from 200 to 500, from 500 to 2,500 etc. This same principle applies to ranges reciting only one numerical value, such as "at least one". Furthermore, such an interpretation should apply regardless of the breadth of the range or the characteristics being described.

Method of Producing ssDNA

The present invention provides a method for the recombinant production of DNA single stranded molecules, in particular single stranded DNA oligonucleotides and polypeptides.

Said method comprises the steps of (1) providing a pseudogene nucleic acid, wherein said pseudogene nucleic acid is a nucleic acid that comprises at least one target DNA oligo- or polynucleotide sequence and two self-cleaving DNA sequences flanking each target DNA oligo- or polynucleotide sequence;

(2) integrating the pseudogene nucleic acid into a vector, transforming bacterial cells with said vector and producing a precursor ssDNA from said vector under bacterial culture conditions,
wherein said precursor ssDNA comprises the pseudogene nucleic acid;

(3) isolating the precursor ssDNA from the bacterial culture;

(4) digesting the precursor ssDNA under reaction conditions where the self-cleaving DNA sequences become active; and (5) separating and obtaining the target single stranded DNA oligo- or polynucleotide(s).

(1) Design and Provision of the Pseudogene Nucleic Acid

The "pseudogene nucleic acid" is a nucleic acid that comprises at least one target DNA oligo- or polynucleotide sequence and two self-cleaving DNA sequences flanking each target DNA oligo- or polynucleotide sequence.

Preferably, the pseudogene nucleic acid comprises one or many target DNA oligo- or polynucleotide sequences, such as two, three, four or more than about 50 target DNA oligo- or polynucleotide sequences.

The target DNA oligo- or polynucleotide sequences can be identical or be different, in their sequence as well as in their length.

Preferably, a target DNA oligo- or polynucleotide sequence has a length in the range from about 20 nucleotides to about several thousand nucleotides, covering and exceeding the range in which chemically synthesized oligonucleotides are available.

Preferably, the self-cleaving DNA sequences flanking each of the target DNA oligo- or polynucleotide sequences in the pseudogene nucleic acid are self-cleaving deoxyribozymes or DNAzymes, such as Zn$^{2+}$-dependent DNAzymes,
e.g. I-R3, and the other variants described in Gu et al., 2013 as well as variants derived from the ones described in Gu et al., 2013.

Deoxyribozymes (also called DNAzymes) are DNA molecules that form structures capable of catalyzing chemical reactions (Breaker, 1997). There are DNAs that catalyze self-processing reactions (Carmi et aL, 1996). Such deoxyribozymes can be harnessed to create DNA constructs that become modified based on their inherent catalytic activities when exposed to specific reaction conditions. For example, there are engineered self-cleaving deoxyribozymes that employ oxidation (Carmi et al., 1996), depurination (Sheppard et al., 2000), or hydrolysis (see e.g. Chandra et aL, 2009) mechanisms that have been created by using various directed evolution strategies.

Recently, two classes of engineered self-cleaving deoxyribozymes were described that hydrolyze DNA with high speed and sequence specificity (Gu et al., 2013). One such deoxyribozyme, named I-R3 (see FIG. 3), carries a small catalytic core composed of 17 nucleotides flanked by either 1 or 2 double stranded substructures. Representatives of this deoxyribozyme class exhibit an observed rate constant ($k_{obs}$) for DNA hydrolysis of ~1 min$^{-1}$ (half-life of ~40 s) when incubated at near neutral pH and in the presence of millimolar concentrations of Zn$^{2+}$. This deoxyribozyme cleaves the phosphoester bond between the 3' oxygen and the phosphorus center of an ApA linkage to yield a 3' cleavage fragment with a 5' phosphate group.

```
P1-TAGTTGAGCTGT-P2-P3-P2'-ACGTTGAAG-P1'
or

P2'-ACGTTGAAG-P1-P3-P1'-TAGTTGAGCTGT-P2
``` wherein TAGTTGAGCTGT is SEQ ID NO: 1 and ACGTTGAAG is SEQ ID NO: 2; and wherein P3 is a spacer of arbitrary sequence and where P1 and P1' are two complementary sequences that form a DNA double helix. The same holds true for P2 and P2'.

```
P1-[SEQ ID NO: 1]-P2-P3-P2'-[SEQ ID NO: 2]-P1'

P2'-[SEQ ID NO: 2]-P1-P3-P1'-[SEQ ID NO: 1]-P2
```

The self-cleaving DNA sequences used in the present invention (i.e. the self-cleaving desoxyribozymes or DNAzymes) become only active (and catalyze self-cleaving) under defined reaction conditions.

For example, Zn$^{2+}$-dependent DNAzymes, e.g. I-R3, require the addition of Zn ions.

The pseudogene nucleic acid can be synthesized by conventional/established gene synthesis methods.

For example, it can be ordered and synthesized by a commercial vendor.

(2) Production of Precursor ssDNA in Bacterial Culture In step (2), the pseudogene nucleic acid is integrated into a vector. Said vector is introduced into bacterial cells via transformation and a precursor ssDNA is produced from said vector under bacterial culture conditions.

In some embodiments, the vector is at least one vector, such as two, three, four or more vectors.

The "precursor single stranded DNA" or "precursor ssDNA" comprises the pseudogene nucleic acid in single stranded form and the vector backbone.

Preferably, the bacteria are selected from *E. coli*, in particular K12-derived *E. coli* safety strains, such as DH5alpha, XL-1blue or JM109.

In a preferred embodiment, the vector in step (2) is a phagemid.

In some embodiments, the phagemid is at least one phagemid, such as two, three, four or more phagemids.

Said (at least one) phagemid comprises a plasmid backbone and can optionally comprise further component(s), such as
- a packaging sequence,
- component(s) ensuring propagation of the phagemid during cell division,
- a selection marker,
  - typically an antibiotic resistance gene.

In said embodiment, furthermore a helper plasmid or a helper phage is used which comprises further component(s), such as
- genes encoding the proteins of a bacteriophage, e.g. M13 bacteriophage
- component(s) ensuring propagation of the helper plasmid during cell division,
- a selection marker,
  - typically an antibiotic resistance gene.

In this embodiment, both the (at least one) phagemid and the helper plasmid or the helper phage are introduced into the bacterial cells, preferably via simultaneous transformation.

In this embodiment, where the vector is a phagemid (and which also uses a helper plasmid), the phagemid is amplified inside the bacterial cells via rolling circle amplification (RCA). The same applies for embodiments utilizing more than one phagemid.

The rolling circle amplification (RCA) results in the single stranded form of the phagemid, phagemid ssDNA". Said phagemid ssDNA is in this embodiment the "precursor ssDNA".

Said phagemid ssDNA is preferably packaged into phage-like particles on the cell surface which are preferably secreted from the cells into the surrounding medium.

The phage-like particles contain the phagemid ssDNA instead of the normal phage genome.

For example, in an embodiment where the helper plasmid contains the genes encoding the proteins of M13 bacteriophage, M13 bacteriophage-like particles are formed which are secreted from the host cells without cell lysis.

(3) Obtaining the Precursor ssDNA from the Bacterial Culture

The precursor ssDNA is isolated from the bacterial culture.

Said isolation or purification can be carried out by using conventional/established methods known in the art,
such as centrifugation, precipitation, solvent-based extraction, chromatographic methods, or combinations thereof.

In one embodiment, where (at least one) phagemid and a helper plasmid are utilized, the isolation or purification comprises
- extracting the phage-like particles from the cell culture, preferably from the culture supernatant,
  - such as via pelleting the cells and removing/extracting the phage-like particles from the supernatant, such as by precipitation (e.g. using PEG)
- extracting the phagemid ssDNA from the phage-like particles,
  - such as via chemical lysis of the protein coat and ethanol precipitation of the ssDNA.

For example, downstream processing of ssDNA can include the following steps: separation of host cells and extracellular produced phage-like particles, PEG-mediated phage precipitation, chemical phage lysis and ssDNA precipitation with ethanol.

See e.g. Kick et al., 2015.

(4) Autocatalytic Digest of the Precursor ssDNA

The isolated precursor ssDNA is then digested, in an autocatalytic-manner, i.e. the self-cleaving DNA sequences will cleave the precursor ssDNA.

Said digest is carried out under reaction conditions where the self-cleaving DNA sequences become active.

In one embodiment, where $Zn^{2+}$-dependent DNAzymes, e.g. I-R3, are utilized, said digestion of step (4) is triggered by the addition of $Zn^{2+}$ ions, i.e. the reaction conditions where the self-cleaving DNA sequences become active require the presence of $Zn^{2+}$ ions.

(5) Obtaining the Target Single Stranded DNA Molecule(s)

Next, the target single stranded DNA oligo- or polynucleotide(s) will be separated, in particular from the self-cleaving DNA sequences which are the by-products of step (4).

Said separation or purification can be carried out by using conventional/established methods known in the art,
such as
- precipitation, e.g. with ethanol and potassium acetate, or with polyethylene glycol, chromatography,
- or combinations thereof.

Finally, the target single stranded DNA oligo- or polynucleotide(s) are obtained.

(6) Further Steps

In one embodiment, the method of the present invention, comprising the further step of
(6) further processing of the target single stranded DNA oligo- or polynucleotide(s).

For example, the target single stranded DNA oligo- or polynucleotide(s) can be self-assembled and/or folded into DNA origami structures, tile-based DNA nanostructures, or crystalline DNA nanomaterials. Alternatively, they can be used as aptamers or DNAzymes to bind, detect, or process other molecules.

Mass production of ssDNA molecules

In one embodiment, the bacterial culture is carried out in a bioreactor, such as a stirred-tank bioreactor.

Such an embodiment allows for the production of target ssDNA molecules in the gram scale.

Thus, a mass production of single stranded DNA molecules is possible.

Uses of the ssDNA Molecules Obtained

The present invention provides the use of the target single stranded DNA oligo- or polynucleotide(s) obtained in the method of the present invention in DNA nanotechnology.

For example, the target single stranded DNA oligonucleotide(s) and polynucleotide(s) can be designed to be able to self-assemble into DNA origami structures, i.e. being a scaffold strand and several staple strands.

DNA origami structures can be:
DNA nanorods,
  such as described in Example 1 herein;
DNA nanopores,
  such as described in European patent application No. 2 695 949;
DNA helix tubes
  such as described in Example 3 herein;
DNA pointer objects,
  such as described in Example 3 herein or in Bai et al., 2012;
therapeutically active DNA nanostructures or drug delivery vehicles, positioning devices, Nanosensors The present invention provides the use of the target single stranded DNA oligo- or polynucleotide(s) obtained in the method of the present invention as research tools.

The present invention provides the use of the target single stranded DNA oligo- or polynucleotide(s) obtained in the method of the present invention as probes for diagnostics.

The present invention provides the use of the target single stranded DNA oligo- or polynucleotide(s) obtained in the method of the present invention in gene therapy.

The present invention provides the use of the target single stranded DNA oligo- or polynucleotide(s) obtained in the method of the present invention in molecular sensing/as a molecular sensor.

Further Description of Preferred Embodiments

We present a biotechnological method for the recombinant production of single stranded DNA oligonucleotides in bacteria. With said method, single stranded DNA molecules with a length of up to several thousand bases can be produced in any scalable amount. Due to this method, a mass production of DNA-based nanostructures becomes practically possible.

The method comprises seven steps, as shown in the flow diagram of FIG. 1.

In step (1), a pseudogene is designed or constructed which comprises the DNA nucleotide sequences to be produced in a special conditioned form. This form, which is described in more detail below, is essential for the method of the invention.

In step (2), the pseudogene is generated via current/ established methods of gene synthesis.

Next, the pseudogene is integrated into vectors or plasmids and produced as "concatenated precursor ssDNA" in a liquid bacterial (*E. coli*) culture in a scalable manner (step (3)).

Then, the concatenated precursor ssDNA is purified and isolated (step (4)).

In step (5), the concatenated precursor ssDNA is digested in an autocatalytic manner, wherein said digest is an important feature of the method of the present invention.

The target single stranded DNA oligonucleotides which result from said digest are isolated using conventional methods (step (6)).

The target single stranded DNA oligonucleotides can then be further processed, such as for the generation of DNA origami structures in greater scale (step (7): downstream applications).

Biotechnological production of concatenated precursor ssDNA

Two DNA plasmids are introduced into *E. coli* cells via simultaneous transformation (FIG. 2). The "helper plasmid" contains the genes for the proteins of the M13 bacteriophage and further information (plasmid backbone) which ensure propagation of the helper plasmid into the daughter cells during *E. coli* cell division. The "phagemid" (=phageplasmid) contains the DNA oligonucleotide sequences to be produced in a special conditioned form ("concatenated precursor ssDNA") and further information which, among other things, ensure propagation of the phagemid during cell division.

At first, each of the two plasmids needs to be generated via cloning. For generating the phagemid with the concatenated precursor ssDNA, a conventional gene synthesis needs to be carried out beforehand.

Inside the cell, the phagemid is amplified (via rolling circle amplification). At the same time, the M13 phage proteins are produced.

The single stranded phagemid contains a special packaging sequence through which it is recognized by the phage proteins and packaged to phage particles. Consequently, the cell secretes phage-like particles which contain—instead of the normal phage genome—the single stranded form of the phagemid and, thus, the DNA oligonucleotide sequences to be produced.

The phage particles can be isolated from the supernatant after the cells were pelleted. The DNA contained in the phage particles can be purified.

The biotechnological process described above is scalable, as is the recombinant production of proteins in bacterial cultures (Kick et al., 2015).

Further processing of the concatenated precursor ssDNA

FIG. 3 shows the structure of the pseudogene in said special conditioned form, namely the "concatenated precursor ssDNA".

The DNA oligonucleotide sequences to be produced are flanked at both termini by catalytically active DNA sequences ("I-R3"), see Gu et al. (2013). These DNAzymes have a self-cleaving effect, i.e., said DNAzymes catalyze a backbone hydrolysis (at the positions shown in FIG. 3's inset as black arrow heads) after addition of bivalent zinc cations and under suitable reaction conditions.

The concatenated precursor ssDNA can, thus, contain many different DNA oligonucleotide sequences.

After purification of the precursor ssDNA the catalysis can be started by adding zinc ("cleavage").

Due to the cleavage, the precursor ssDNA separates or falls into the desired single stranded DNA oligonucleotides and in the catalytic DNAzymes, which are a by-product. The DNAzymes can be separated from the target DNA oligonucleotides, e.g. via chromatography.

Advantages of the method of the present invention

Methods for the biotechnological production of single stranded phagemid DNA with helper plasmids (Marchi et al., 2014) or enzymes (Schmidt et al, 2015) have been described in the art. Furthermore, methods containing digesting long circular ssDNA with the help of restriction endonucleases at user-defined sequences have been described in the art (Ducani et al., 2013).

In the method described by Ducani et al. (2013), protein-based restriction nucleases are utilized and, thus, required as additional reagents. These enzymes need to be either purchased or produced in a separate biotechnological process. Furthermore, in the method described by Ducani et al., all staple oligonucleotides are purified using preparative gel electrophoresis, which is tedious and does not scale. In the method, described herein, no further cost intensive or labor intensive reagents are needed for the digest, since all components required for generating the target DNA oligonucleotide sequences are already contained in the combined system of helper plasmid phagemid with pseudogene.

An essential aspect of the invention is the use of catalytically active DNA sequences produced via directed evolution, i.e., DNAzymes (Gu et al., 2013). Said catalytically active DNA sequences are contained in the concatenated precursor ssDNA and are amplified in the biotechnological process together with the target DNA oligonucleotide sequences. The method presented by Gu et al. produces oligonucleotides of different lengths, but not of arbitrary sequence. Their precursor DNA contains several copies of the same redundant sequence. The method, described herein, enables the production of oligonucleotides with arbitrary sequence, as required for the production of DNA origami. Furthermore, while Gu et al. use the same terminal sequence and thus the same DNAzyme, the method of the present invention uses different DNAzyme sequences for producing different target oligonucleotide sequences.

The following examples and drawings illustrate the present invention without, however, limiting the same thereto.

EXAMPLES

Example 1 Generation of a DNA-Based Nanorod

Figure 1:
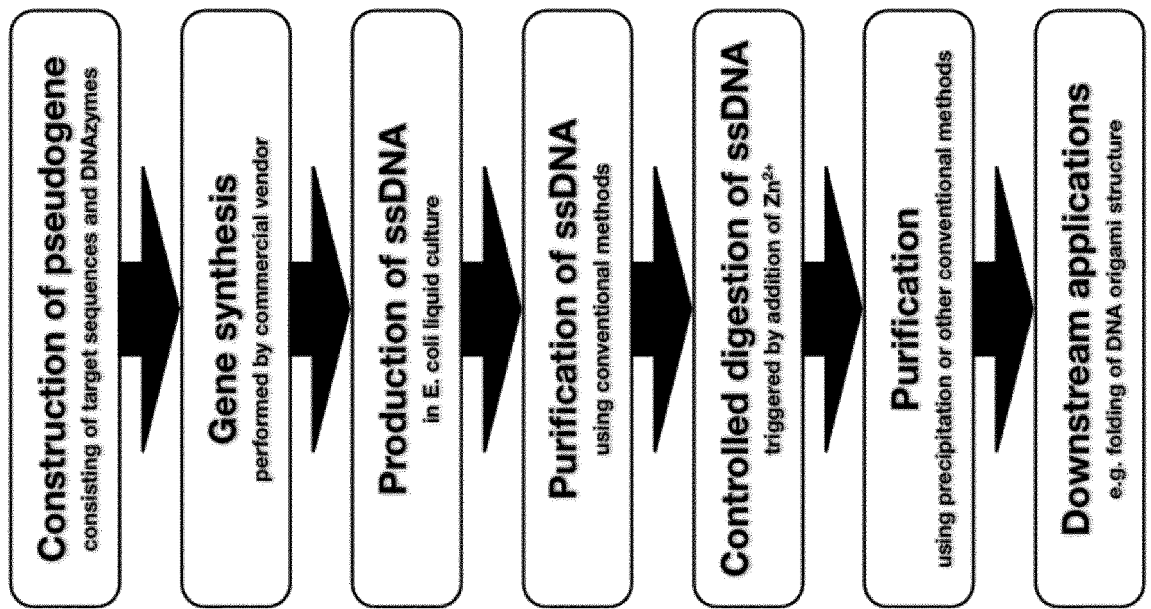
FIG. 1: Flow chart showing the biotechnological production of concatenated precursor single strand DNA.
Figure 2:
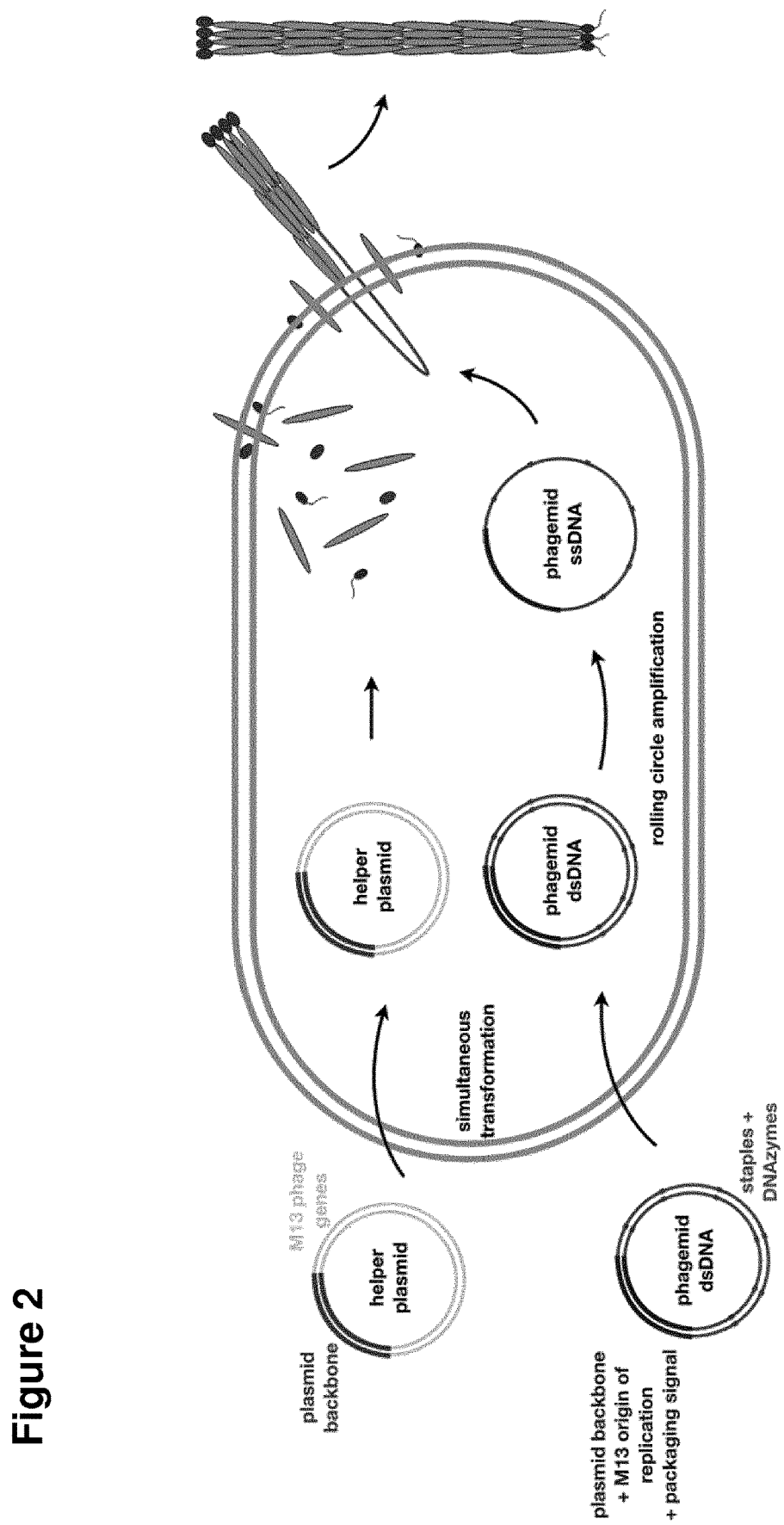
FIG. 2: Schematic illustration of the helper plasmid-assisted production of helper phagemid single strand DNA.
Figure 3:
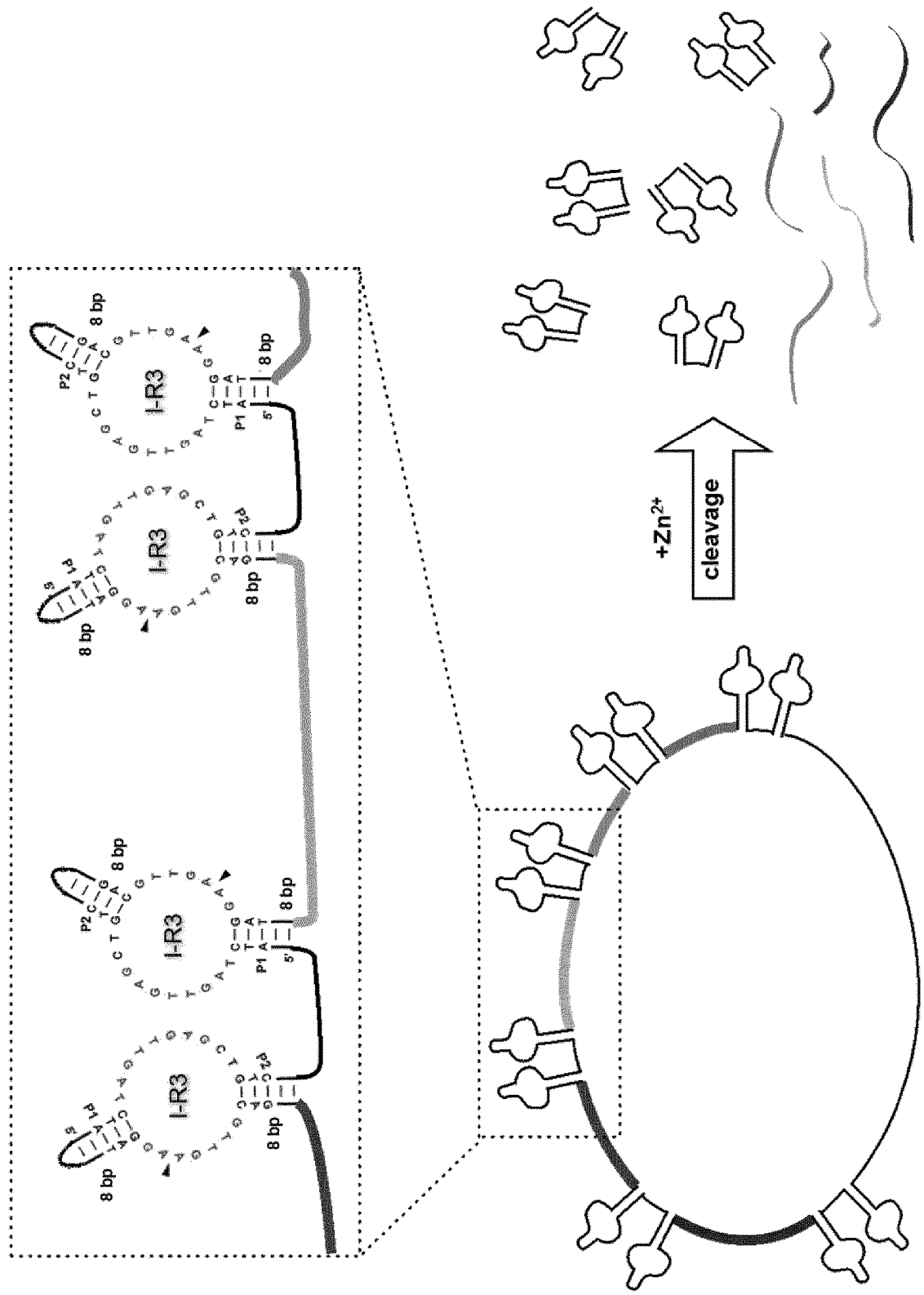
FIG. 3: Schematic illustration of a phagemid containing 5 target sequences (bold lines) and (5+1)×2 flanking catalytic DNAzyme sequences (hairpin structures P1—[SEQ ID NO: 1]—P2—P3—P2'—[SEQ ID NO: 2]—P1'; and P2'—[SEQ ID NO: 2]—P1—P3—P1'—[SEQ ID NO: 1]—P2) for the extraction of the target molecules.
Figure 4:
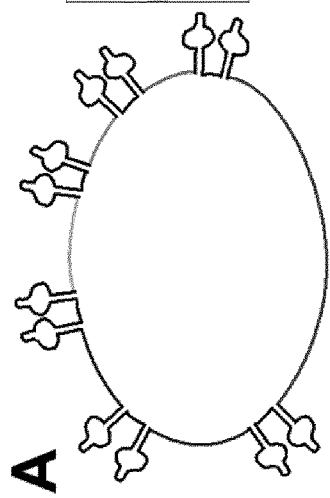
FIG. 4: Production of a DNA origami nanorod using biotechnologically produced single stranded starting materials.
- A, Schematic representation of the phagemid (left) and the internal strand topology of the DNA nanorod.
- B, View of an agarose gel on which the products of a self-assembly of a 10-helix bundle using staple oligonucleotides produced via chemical solid phase synthesis (left) are compared with the use of staple oligonucleotides produced by the method of the invention (right). Both samples show comparable migration properties which implies a comparable assembly quality.
- C, Transmission electron microscopy picture of nanorods whose staple oligonucleotides were produced by the method of the invention.
Figure 4:
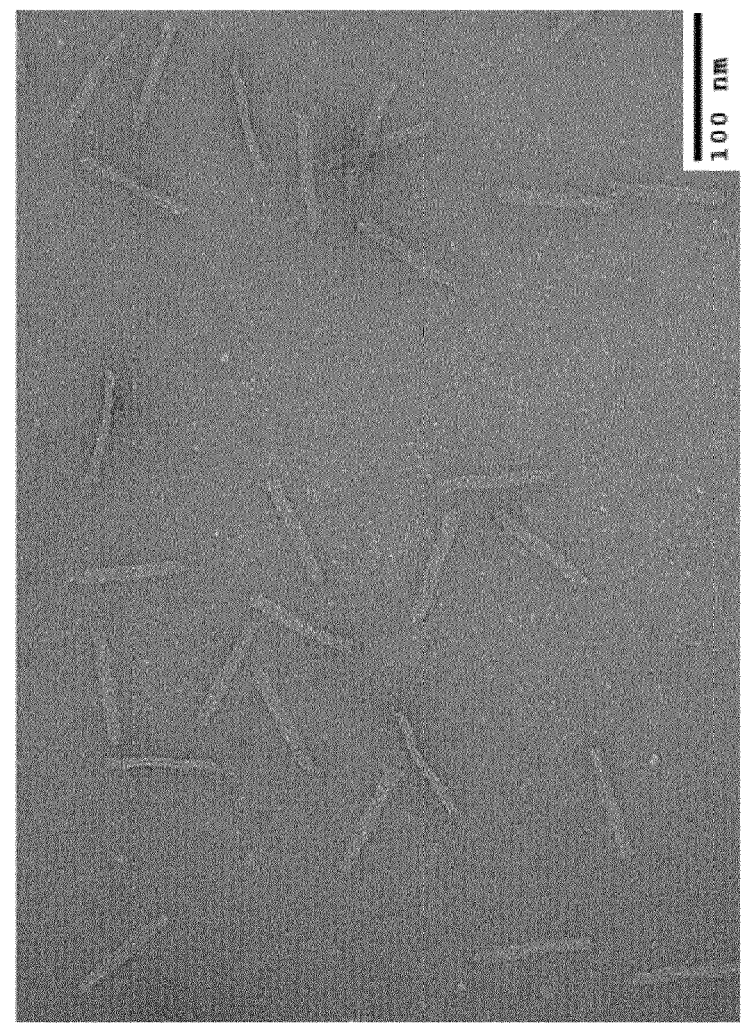

As a prototype, a DNA-based nanorod was generated from DNA materials which were exclusively produced by the method of the present invention. The DNA-based nanorod was designed and developed with the DNA origami design method (see Rothemund, 2006; see also US patent applications 2007/117109 A1 and 2012/251583 A1; U.S. Pat. Nos. 7,842,793 B2 and 8,501,923 B2) and consists of 10 DNA double helices which are aligned in parallel in a honeycomb lattice and are cross-linked via strand connections (see FIG. 4A). For the nanorod a 2500 base long single stranded DNA backbone molecule ("scaffold strand") is needed as well as 21 DNA oligonucleotides ("staple strands") each with a length of about 100 bases. All required construction elements are derived from a phagemid which was especially constructed therefor.

1.1 Materials & Methods

Sequences:

DNAzymes:

P1-[SEQ ID NO: 1]-P2-P3-P2'-[SEQ ID NO: 2]-P1'

P2'-[SEQ ID NO: 2]-P1-P3-P1'-[SEQ ID NO: 1]-P2

Wherein is SEQ ID NO: 1=TAGTTGAGCTGT and is SEQ ID NO: 2=ACGTTGAAG; and wherein P3 is a spacer of arbitrary sequence and where P1 and P1' are two complementary sequences that form a DNA double helix. The same holds true for P2 and P2'.

21 oligonucleotides, each with a length of about 100 bases:
SEQ ID NO: 3:
TACTCTTAGAAGTGTCCCAACTACACTAGAAGGACAGTGGCGAGAGGATTACGCGCCTAGATCAACTTTAATGTTGACTCGTGCACCCAACATG

CTTTTTAGCTC

SEQ ID NO: 4:
GCACATTGAGGGCTGCTATTAAGACACGACTTATCCCTTTCTCAAAAGGCCAGCAAAGCGATCTGGCCCCAATAGGGGAACAAGAGGCAGAACA

TATCAAAGCGA

SEQ ID NO: 5:
CTTACCGAGAATAGACACCCGCCTTACAGCGAGGCGAAGGGCTTTAAATCAATCTAGAGCATCATACCAGGCGTTTCGTTCTTGGCGCCGCAAC

CACCTGTATGC

SEQ ID NO: 6:
TAGACCGCGAAAAATGACGGGGAAAGCCTGGCGAATAACTACGTTGCCTGACTCCCGGGGATATTCTCATAGCTCACTAACTATTGTGCTGTAG

AGCTCCGTCTA

SEQ ID NO: 7:
GGCGACCAAACTCTCAGGGTTATTGTCTGATTTATCGCGTCCGGCGGTGCTACAGACCCCTGGTCCGCCCCCCTGACAAGTATAAAACCAGCAT

TTATCAAGGAT

SEQ ID NO: 8:
TCAGGGCATAAATCGCGTTAATATTTTGCGCGGGGATTAAGTTGCGCCTTATCCGGGCTGTAGTATCCACAGAATCACGCGTATGTTTGTCATT

GTAAAAAGAA

SEQ ID NO: 9:
CTTCGGTGTTTGGTCCATCCAAAAAGGATCTTCACAGAAAAATGTTTGCAAGCAGCAGTATTTCATTCAGAAAGCGGTCTGTGACTGGTGATAA

CCCAATACTCA

SEQ ID NO: 10:
AAGGAGCGGGAAGGCAATGATGAGGCACCTATCTCAAGGCCACGGATACCTGTCCGGCCACTGGTGCGGGAGGGAAGCACTATTAAAGAACCAG

TTTGGTTCCGC

SEQ ID NO: 11:
CTACAGGAAGTTGGCTGCATAATTCTCTTTCACCAAATGCCGCAAAAAAAATTGTTGTGTCACCCAGTTACCTTCGGAAACCACTGATCTTTTC

TACGTTAAGGGAGCTAGA

SEQ ID NO: 12:
AGAGGCGTGGGCGCTCTTCCGATACGGTGTATCTCAGTTCGGCGACCGCTGGGTAACCCTAAACACTACGTGAACCACCGAAATTCGCGTT

SEQ ID NO: 13:
TCATGAGGATCCTTCGCTGGTAGCGGTGGCTGAAGGCTCGTCCCTCCGAATGCCATCCGTAAGTGATCTTAGGGCGACACGGAATCCGCCTATG

GCTTGGTATCT

SEQ ID NO: 14:
AAACTTGCATAGGCAAGCTCCCTCGTGCGTATGTACATTCGCTGTAGCGTCTTGCCCGGCGTCGGAAAACGGATACATATTTGAGACCCACGCT

GCGCATTAGCA

SEQ ID NO: 15:
TTCGTTCATGTGAGCCCTTCGGGAAGCGCCCGGTACGCCAGCGGCGAACCCAACGTCAAAGGGAGATAGGAAAGTGCCACCTAAGTGTAGAAGG

GGGACGTCTTG

SEQ ID NO: 16:
TCGACGCATGAAGTCGAGCGCCCTTTTTGATCCAGTTCGATGGTACTCACCATGTTGTGCAAACTCCGGTGTCCTGCCTTTTAAATTAAAATCA

AGTCAAACCCG

SEQ ID NO: 17:
TAAAAAGAATCAGTACCGCGTATGTATTAAGTGCTCATCATTAATACGGAGGGCGCTGGCAAGCATTCAGGCTCACCAGTTACCAATGCTTGCC

GCGTTGTTCCG

SEQ ID NO: 18:
ACAGGACCTACGGCGATCAAGTGATCCCACCAAGTCATTCTGCTGTTGACAATATTATTGAAGCCAGCCGGCTTAATAAGTGGTGGCCTAATAT

AAAGACAAAAA

-continued

SEQ ID NO: 19:
ACCCTGCTAACAGGAACTGTTGGGCGCTGATAATACCGCGCCACTTTAATAGAAAAATAAACAAGTGCTGGCGATCGGCAGCAGCCACTGGCGC

TTACGGAACCG

SEQ ID NO: 20:
GCGCTCTGTTTTTTAAGGATCTCAAGAAATTATCAGTCTATTGGGAATACAGCATCTTTTACTTACTGTCTCGTTGTCAGAAGTCATCGTGGCC

GGGAATTTTGG

SEQ ID NO: 21:
GAGCGAGGCTCTCCTGCTGGCGTTTTTCGTCTGACGGCTCCACATGAGCGTTCTTCGGGGCGAGAGTTGCGTCACGCTGCGCGTTACAGGGCAG

CAATTATGAGT

SEQ ID NO: 22:
AGTCCAATGGCGCTACGCAGGAAAGAACATCCATAGATACGGTCCCCGAGTTGAGTGTTGTTCGTGGACTGTGGCGAGAAAGGACCTCTTCTAC

CATCTGTCTAT

SEQ ID NO: 23:
TTCAGCCTGTAGGTACTCAAAGGCGGTACTTCCTCGCCAACGTTAAAATCGGCAAATCCCTTGATGGCCGGGAGCCCCGATTCAAGGCG

Phagemid backbone that serves as scaffold:
SEQ ID NO: 24
GTTGTcgtctctgaagATGTGAGCtacaacgtcgtgactgggaaaaccctggcgttacccaacttaatcgccttgcagcacatccccctttcgc cagctggcgtaatagcgaagaggcccgcaccgatcgcccttcccaacagttgcgcagcctgaatggcgaatgggacgcgccctgtagcggcgca ttaagcgcggcgggtgtggtggttacgcgcagcgtgaccgctacacttgccagcgccctagcgcccgctcctttcgctttcttcccttcctttc tcgccacgttcgccggctttccccgtcaagctctaaatcgggggctccctttagggttccgatttagtgctttacggcacctcgaccccaaaaa acttgattagggtgatggttcacgtagtgggccatcgccctgatagacggtttttcgccctttgacgttggagtccacgttctttaatagtgga ctcttgttccaaactggaacaacactcaaccctatctcggtctattcttttgatttataaggggattttgccgatttcggcctattggttaaaaa atgagctgatttaacaaaaatttaacgcgaattttaacaaaatattaacgcttacaatttaggtggcacttttcggggaaatgtgcgcggaacc cctatttgtttatttttctaaatacattcaaatatgtatccgctcatgagacaataaaccctgataaatgcttcaataatattgaaaaaggaaga gtatgagtattcaacatttccgtgtcgcccttattcccttttttgcggcattttgccttcctgtttttgctcacccagaaacgctggtgaaagt aaaagatgctgaagatcagttgggtgcacgagtgggttacatcgaactggatctcaacagcggtaagatccttgagagttttcgccccgaagaa cgttttccaatgatgagcacttttaaagttctgctatgtggcgcggtattatcccgtattgacgccgggcaagagcaactcggtcgccgcatac actattctcagaatgacttggttgagtactcaccagtcacagaaaagcatcttacggatggcatgacagtaagagaattatgcagtgctgccat aaccatgagtgataacactgcggccaacttacttctgacaacgatcggaggaccgaaggagctaaccgcttttttgcacaacatgggggatcat gtaactcgccttgatcgttgggaaccggagctgaatgaagccataccaaacgacgagcgtgacaccacgatgcctgtagcaatggcaacaacgt tgcgcaaactattaactggcgaactacttactctagcttcccggcaacaattaatagactggatggaggcggataaagttgcaggaccacttct gcgctcggcccttccggctggctggtttattgctgataaatctggagccggtgagcgtgggtcAcgcggtatcattgcagcactggggccagat ggtaagccctcccgtatcgtagttatctacacgacggggagtcaggcaactatggatgaacgaaatagacagatcgctgagataggtgcctcac tgattaagcattggtaactgtcagaccaagtttactcatatatactttagattgatttaaaacttcattttttaatttaaaaggatctaggtgaa gatcctttttgataatctcatgaccaaaatcccttaaCgtgagttttcgttccactgagcgtcagacccgtagaaaagatcaaaggatcttct tgagatcctttttttctgcgcgtaatctgctgcttgcaaacaaaaaaaccaccgctaccagcggtggtttgtttgccggatcaagagctaccaa ctcttttccgaaggtaactggcttcagcagagcgcagataccaaatactgtccttctagtgtagccgtagttaggccaccacttcaagaactc tgtagcaccgcctacatacctcgctctgctaatcctgttaccagtggctgctgccagtggcgataagtcgtgtcttaccgggttggactcaaga cgatagttaccggataaggcgcagcggtcgggctgaacggggggttcgtgcacacagcccagcttggagcgaacgacctacaccgaactgagat acctacagcgtgagctatgagaaagcgccacgcttcccgaagggagaaaggcggacaggtatccggtaagcggcagggtcggaacaggagagcg cacgagggagcttccagggggaaacgcctggtatctttatagtcctgtcgggtttcgccacctctgacttgagcgtcgatttttgtgatgctcg tcaggggggcggagcctatggaaaaacgccagcaacgcggcctttttacggttcctggccttttgctggccttttgctcacatgttctttcctg cgttatcccctgattctgtggataaccgtattaccgcctttgagtgagctgataccgctcgccgcagccgaacgaccgagcgcagcgagtcagt gagcgaggaagcggaagagcgcccaatacgcaaaccgcctctccccgcgcgttggccgattcattaaCTTAATTGCagcaagagacgCTTCT Full phagemid ssDNA sequence (=precursor ssDNA):

SEQ ID NO: 25:

ttttccaatgatgagcacttttaaagttctgctatgtggcgcggtattatcccgtattgacgccgggcaagagcaactcggtcgccgcatacac
tattctcagaatgacttggttgagtactcaccagtcacagaaaagcatcttacggatggcatgacagtaagagaattatgcagtgctgccataa
ccatgagtgataacactgcggccaacttacttctgacaacgatcggaggaccgaaggagctaaccgcttttttgcacaacatggggatcatgt
aactcgccttgatcgttgggaaccggagctgaatgaagccataccaaacgacgagcgtgacaccacgatgcctgtagcaatggcaacaacgttg
cgcaaactattaactggcgaactacttactctagcttcccgcaacaattaatagactggatggaggcggataaagttgcaggaccacttctgc
gctcggcccttccggctggctggtttattgctgataaatctggagccggtgagcgtgggtctcgcggtatcattgcagcactggggccagatgg
taagccctcccgtatcgtagttatctacacgacggggagtcaggcaactatggatgaacgaaatagacagatcgctgagataggtgcctcactg
attaagcattggtaactgtcagaccaagtttactcatatatactttagattgatttaaaacttcattttaatttaaaaggatctaggtgaaga
tcctttttgataatctcatgaccaaaatcccttaacgtgagttttcgttccactgagcgtcagacccgtagaaaagatcaaaggatcttcttg
agatcctttttttctgcgcgtaatctgctgcttgcaaacaaaaaaaccaccgctaccagcggtggtttgtttgccggatcaagagctaccaact
ctttttccgaaggtaactggcttcagcagagcgcagataccaaatactgtccttctagtgtagccgtagttaggccaccacttcaagaactctg
tagcaccgcctacatacctcgctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtcggaacaggagagcgca
cgagggagcttccaggggaaacgcctggtatctttatagtcctgtcgggtttcgccacctctgacttgagcgtcgatttttgtgatgctcgtc
aggggggcggagcctatggaaaaacgccagcaacgcggcctttttacggttcctggccttttgctggccttttgctcacatgttctttcctgcg
ttatcccctgattctgtggataaccgtattaccgcctttgagtgagctgataccgctcgccgcagccgaacgaccgagcgcagcgagtcagtga
gggaggaagcggaagagcgcccaatacgcaaaccgcctctccccgcgcgttggccgattcattaaCTTAATTGCacGTTGAAGCGTTACCTGTT
AGGTAACGTAGTTGAGCTgtGCAATTAATTTTTTAAGAGTATAGTTGAGCTGTCACAGAATGTGACGTTGAAGTACTCTTAGAAGTGTCCCAAC
TACACTAGAAGGACAGTGGCGAGAGGATTACGCGCCTAGATCAACTTTAATGTTGACTCGTGCACCCAACATGCTTTTTAGCTCACGTTGAAGC
GTTACCTGTTAGGTAACGTAGTTGAGCTGTGAGCTAAATTTTTTCAATGTGTAGTTGAGCTGTCACAGAATGTGACGTTGAAGCACATTGAGGG
CTGCTATTAAGACACGACTTATCCCTTTCTCAAAAGGCCAGCAAAGCGATCTGGCCCCAATAGGGGAACAAGAGGCAGAACATATCAAAGCGAC
GTTGAAGCGTTACCTGTTAGGTAACGTAGTTGAGCTGTCGCTTTGATTTTTTCGGTAAGTAGTTGAGCTGTCACAGAATGTGACGTTGAAGCTT
ACCGAGAATAGACACCCGCCTTACAGCGAGGCGAAGGGCTTTAAATCAATCTAGAGCATCATACCAGGCGTTTCGTTCTTGGCGCCGCAACCAC
CTGTATGCACGTTGAAGCGTTACCTGTTAGGTAACGTAGTTGAGCTGTGCATACAGTTccTGCGGTCTATAGTTGAGCTGTCACAGAATGTGAC
GTTGAAGTAGACCGCGAAAAATGACGGGGAAAGCCTGGCGAATAACTACGTTGCCTGACTCCCGGGGATATTCTCATAGCTCACTAACTATTGT
GCTGTAGAGCTCCGTCTACGTTGAAGCGTTACCTGTTAGGTAACGTAGTTGAGCTGTAGACGGAGTTTTTTGGTCGCTAGTTGAGCTGTCACA
GAATGTGACGTTGAAGGCGACCAAACTCTCAGGGTTATTGTCTGATTTATCGCGTCCGGCGGTGCTACAGACCCCTGGTCCGCCCCCCTGACAA
GTATAAAACCAGCATTTATCAAGGATACGTTGAAGCGTTACCTGTTAGGTAACGTAGTTGAGCTGTATCCTTGATTTTTTGCCCTGATAGTTGA
GCTGTCACAGAATGTGACGTTGAAGTCAGGGCATAAATCGCGTTAATATTTTGCGCGGGGATTAAGTTGCGCCTTATCCGGGCTGTAGTATCCA
CAGAATCACGCGTATGTTTGTCATTGTAAAAAAGAACGTTGAAGCGTTACCTGTTAGGTAACGTAGTTGAGCTGTTCTTTTTTTTTTCACCGA
AGTAGTTGAGCTGTCACAGAATGTGACGTTGAAGCTTCGGTGTTTGGTCCATCCAAAAAGGATCTTCACAGAAAAATGTTTGCAAGCAGCAGTA
TTTCATTCAGAAAGCGGTCTGTGACTGGTGATAACCCAATACTCACGTTGAAGCGTTACCTGTTAGGTAACGTAGTTGAGCTGTGAGTATTGTT
TTTCGCTCCTTTAGTTGAGCTGTCACAGAATGTGACGTTGAAGAAGGAGCGGGAAGGCAATGATGAGGCACCTATCTCAAGGCCACGGATACCT
GTCCGGCCACTGGTGCGGGAGGGAAGCACTATTAAAGAACCAGTTTGGTTCCGCACGTTGAAGCGTTACCTGTTAGGTAACGTAGTTGAGCTGT
GCGGAACCTTTTTTCCTGTAGTAGTTGAGCTGTCACAGAATGTGACGTTGAAGCTACAGGAAGTTGGCTGCATAATTCTCTTTCACCAAATGCC
GCAAAAAAATTGTTGTGTCACCCAGTTACCTTCGGAAACCACTGATCTTTTCTACGTTAAGGGAGCTAGACGTTGAAGCGTTACCTGTTAGGT
AACGTAGTTGAGCTGTCTAGCTCCTTTTTCCACGCCTTAGTTGAGCTGTCACAGAATGTGACGTTGAAGAGGCGTGGGCGCTCTTCCGATACGG
TGTATCTCAGTTCGGCGACCGCTGGGTAACCCTAAACACTACGTGAACCACCGAAATTCGCGTTACGTTGAAGCGTTACCTGTTAGGTAACGTA
GTTGAGCTGTAACGCGAACCTTTCCTCATGATAGTTGAGCTGTCACAGAATGTGACGTTGAAGTCATGAGGATCCTTCGCTGGTAGCGGTGGCT -continued

```
GAAGGCTCGTCCCTCCGAATGCCATCCGTAAGTGATCTTAGGGCGACACGGAATCCGCCTATGGCTTGGTATCTACGTTGAAGCGTTACCTGTT

AGGTAACGTAGTTGAGCTGTAGATACCATTTTTGCAAGTTTTAGTTGAGCTGTCACAGAATGTGACGTTGAAGAAACTTGCATAGGCAAGCTCC

CTCGTGCGTATGTACATTCGCTGTAGCGTCTTGCCCGGCGTCGGAAAACGGATACATATTTGAGACCCACGCTGCGCATTAGCACGTTGAAGCG

TTACCTGTTAGGTAACGTAGTTGAGCTGTGCTAATGCTTTTTTGAACGAATAGTTGAGCTGTCACAGAATGTGACGTTGAAGTTCGTTCATGTG

AGCCCTTCGGGAAGCGCCCGGTACGCCAGCGGCGAACCCAACGTCAAAGGGAGATAGGAAAGTGCCACCTAAGTGTAGAAGGGGGACGTCTTGA

CGTTGAAGCGTTACCTGTTAGGTAACGTAGTTGAGCTGTCAAGACGTTTTTTTGCGTCGATAGTTGAGCTGTCACAGAATGTGACGTTGAAGTC

GACGCATGAAGTCGAGCGCCCTTTTTGATCCAGTTCGATGGTACTCACCATGTTGTGCAAACTCCGGTGTCCTGCCTTTTAAATTAAAATCAAG

TCAAACCCGACGTTGAAGCGTTACCTGTTAGGTAACGTAGTTGAGCTGTCGGGTTTGTTTTTTCTTTTTATAGTTGAGCTGTCACAGAATGTGA

CGTTGAAGTAAAAGAATCAGTACCGCGTATGTATTAAGTGCTCATCATTAATACGGAGGGCGCTGGCAAGCATTCAGGCTCACCAGTTACCAA

TGCTTGCCGCGTTGTTCCGACGTTGAAGCGTTACCTGTTAGGTAACGTAGTTGAGCTGTCGGAACAATTTTTGGTCCTGTTAGTTGAGCTGTCA

CAGAATGTGACGTTGAAGACAGGACCTACGGCGATCAAGTGATCCCACCAAGTCATTCTGCTGTTGACAATATTATTGAAGCCAGCCGGCTTAA

TAAGTGGTGGCCTAATATAAAGACAAAAACGTTGAAGCGTTACCTGTTAGGTAACGTAGTTGAGCTGTTTTTGTCTCCTTCAGCAGGGTTAGTT

GAGCTGTCACAGAATGTGACGTTGAAGACCCTGCTAACAGGAACTGTTGGGCGCTGATAATACCGCGCCACTTTAATAGAAAAATAAACAAGTG

CTGGCGATCGGCAGCAGCCACTGGCGCTTACGGAACCGACGTTGAAGCGTTACCTGTTAGGTAACGTAGTTGAGCTGTCGGTTCCGTTTTTACA

GAGCGTAGTTGAGCTGTCACAGAATGTGACGTTGAAGCGCTCTGTTTTTAAGGATCTCAAGAAATTATCAGTCTATTGGGAATACAGCATCTT

TTACTTACTGTCTCGTTGTCAGAAGTCATCGTGGCCGGGAATTTTGGACGTTGAAGCGTTACCTGTTAGGTAACGTAGTTGAGCTGTCCAAAAT

TTTTTTGCCTCGCTTAGTTGAGCTGTCACAGAATGTGACGTTGAAGAGCGAGGCTCTCCTGCTGGCGTTTTCGTCTGACGGCTCCACATGAGC

GTTCTTCGGGGCGAGAGTTGCGTCACGCTGCGCGTTACAGGGCAGCAATTATGAGTACGTTGAAGCGTTACCTGTTAGGTAACGTAGTTGAGCT

GTACTCATAACCTTTCCATTGGATAGTTGAGCTGTCACAGAATGTGACGTTGAAGTCCAATGGCGCTACGCAGGAAAGAACATCCATAGATACG

GTCCCCGAGTTGAGTGTTGTTCGTGGACTGTGGCGAGAAAGGACCTCTTCTACCATCTGTCTATACGTTGAAGCGTTACCTGTTAGGTAACGTA

GTTGAGCTGTATAGACAGTTTTTAGGCTGAATAGTTGAGCTGTCACAGAATGTGACGTTGAAGTTCAGCCTGTAGGTACTCAAAGGCGGTACTT

CCTCGCCAACGTTAAAATCGGCAAAATCCCTTGATGGCCGGGAGCCCCCGATTCAAGGCGACGTTGAAGCGTTACCTGTTAGGTAACGTAGTTG

AGCTGTCGCCTTGATTTTTGCTCACATTAGTTGAGCTGTCACAGAATGTGACGTTGAAGATGTGAGCTACAACGTCGTGACTGGGAAAACCCTG

GCGTTACCCAACTTAATCGCCTTGCAGCACATCCCCCTTTCGCCAGCTGGCGTAATAgcgaagaggcccgcaccgatcgcccttcccaacagtt gcgcagcctgaatggcgaatgggacgcgccctgtagcggcgcattaagcgcggcgggtgtggtggttacgcgcagcgtgaccgctacacttgcc agcgccctagcgcccgctcctttcgctttcttcccttcctttctcgccacgttcgccggctttccccgtcaagctctaaatcggggctcctt tagggttccgatttagtgctttacggcacctcgaccccaaaaaacttgattagggtgatggttcacgtagtgggccatcgccctgatagacggt ttttcgccctttgacgttggagtccacgttctttaatagtggactcttgttccaaactggaacaacactcaaccctatctcggtctattctttt gatttataagggattttgccgatttcggcctattggttaaaaaatgagctgatttaacaaaaatttaacgcgaattttaacaaaatattaacgc ttacaatttaggtggcacttttcggggaaatgtgcgcggaacccctatttgtttatttttctaaatacattcaaatatgtatccgctcatgaga caataaccctgataaatgcttcaataatattgaaaaaggaagagtatgagtattcaacatttccgtgtcgcccttattccctttttgcggcat tttgccttcctgtttttgctcacccagaaacgctggtgaaagtaaaagatgctgaagatcagttgggtgcacgagtgggttacatcgaactgga tctcaacagcggtaagatccttgagagttttcgccccgaagaacg
```

2. E. coli Culture Conditions

In this example, a phagemid single stranded DNA was produced in an *E. coli* liquid culture and purified therefrom. To this end, chemically competent DH5alpha cells were co-transformed with the phagemid and the helper plasmid. The thus obtained strain was grown in 2xYT-medium containing 50 mg/l Kanamycin and 100 mg/l Carbenicillin. After incubation at 37° C. overnight, the cultures were centrifuged at 4000 rcf for 30 min. Solid PEG 8000 and NaCl were 30 added to the supernatant to a final concentration of 3% (m/v) each. Phage-like particles were then precipitated by centrifugation at 4000 rcf for 30 min. ssDNA was extracted from these particles as described in Kick et al., 2015.

3. Digest and Assembly of the Target Structure

Figure 5:
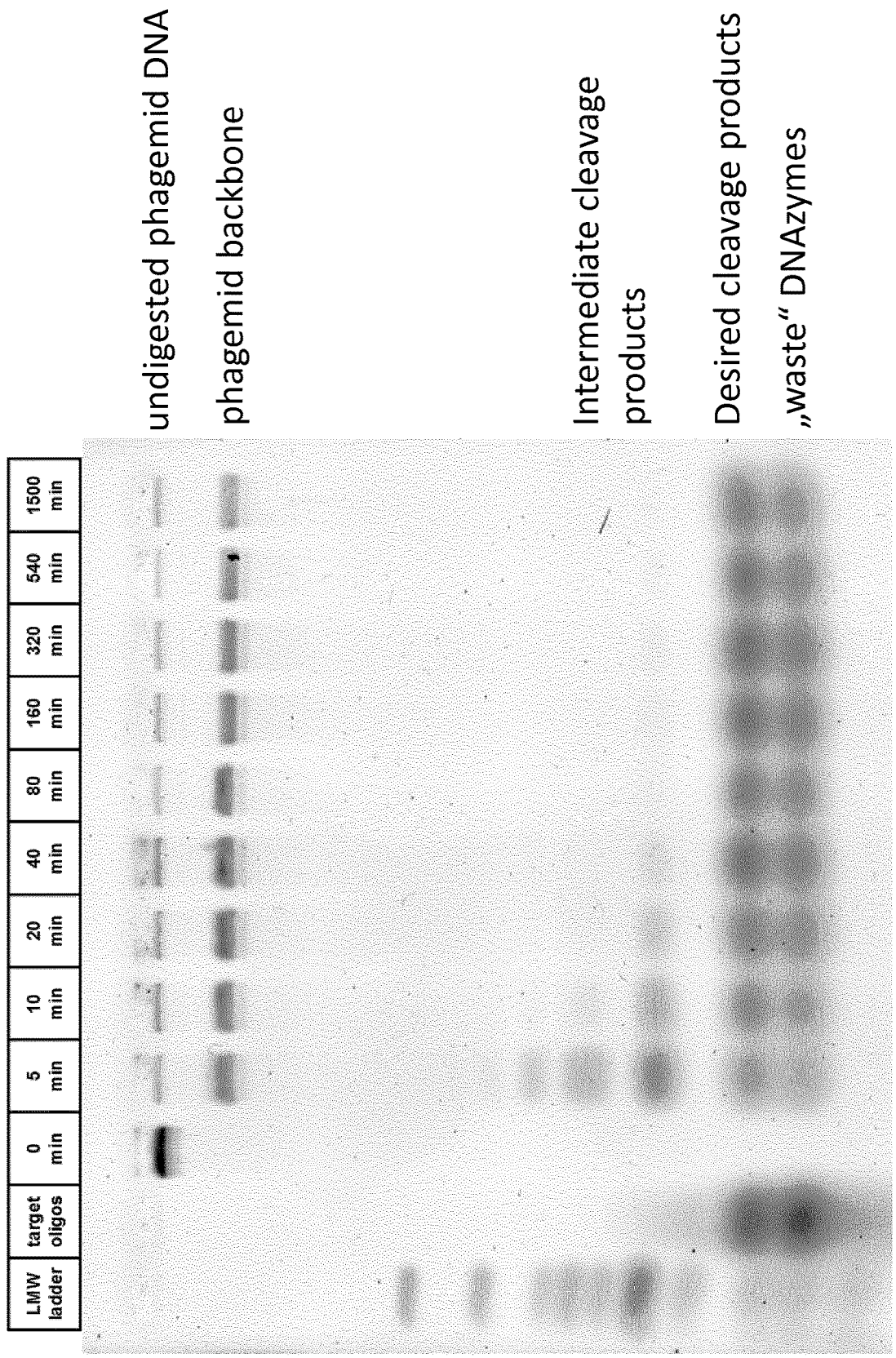
FIG. 5: Illustration of the autocatalytic digest of the concatenated precursor ssDNA into the desired target DNA oligonucleotides by the contained DNAzyme sequences.
Shown is a view of the agarose gel on which the products of the digest reaction of the concatenated precursor ssDNA were electrophoretically separated as function of the incubation time.

The phagemid single stranded DNA was then incubated in reaction buffer (50 mM Hepes pH7, 100 mM NaCl, 2 mM $ZnCl_2$) for three hours at 37° C. After the incubation, the DNA is completely digested into the desired segments, see FIG. 5. Afterwards, the DNA is precipitated with ethanol and potassium acetate and solved in origami folding buffer (10 mM Tris, 5 mM NaCl, 1 mM EDTA, 20 mM $MgCl_2$). The DNA solution is heated for 15 min to 65° C. and then slowly cooled down from 60° C. to 40° C. (three hours per one ° C.). Gel electrophoretic analysis (see FIG. 4B) and transmission electron microscopy (see FIG. 4C) confirm the successful assembly of the target structure.

Example 2 Optimization of DNAzyme Sequences

In order to construct our phagemids, we do not simply place a constant DNAzyme sequence between the target oligonucleotides in the same way a restriction enzyme binding site would be inserted. The sequence of the DNAzyme depends on the terminal sequences of the oligonucleotides that are to be produced. While Gu et al. (Biotechniques 2013) simply use the same terminal sequence and thus the same DNAzyme, our method uses different DNAzyme sequences for producing different target oligonucleotide sequences.

Figure 6:
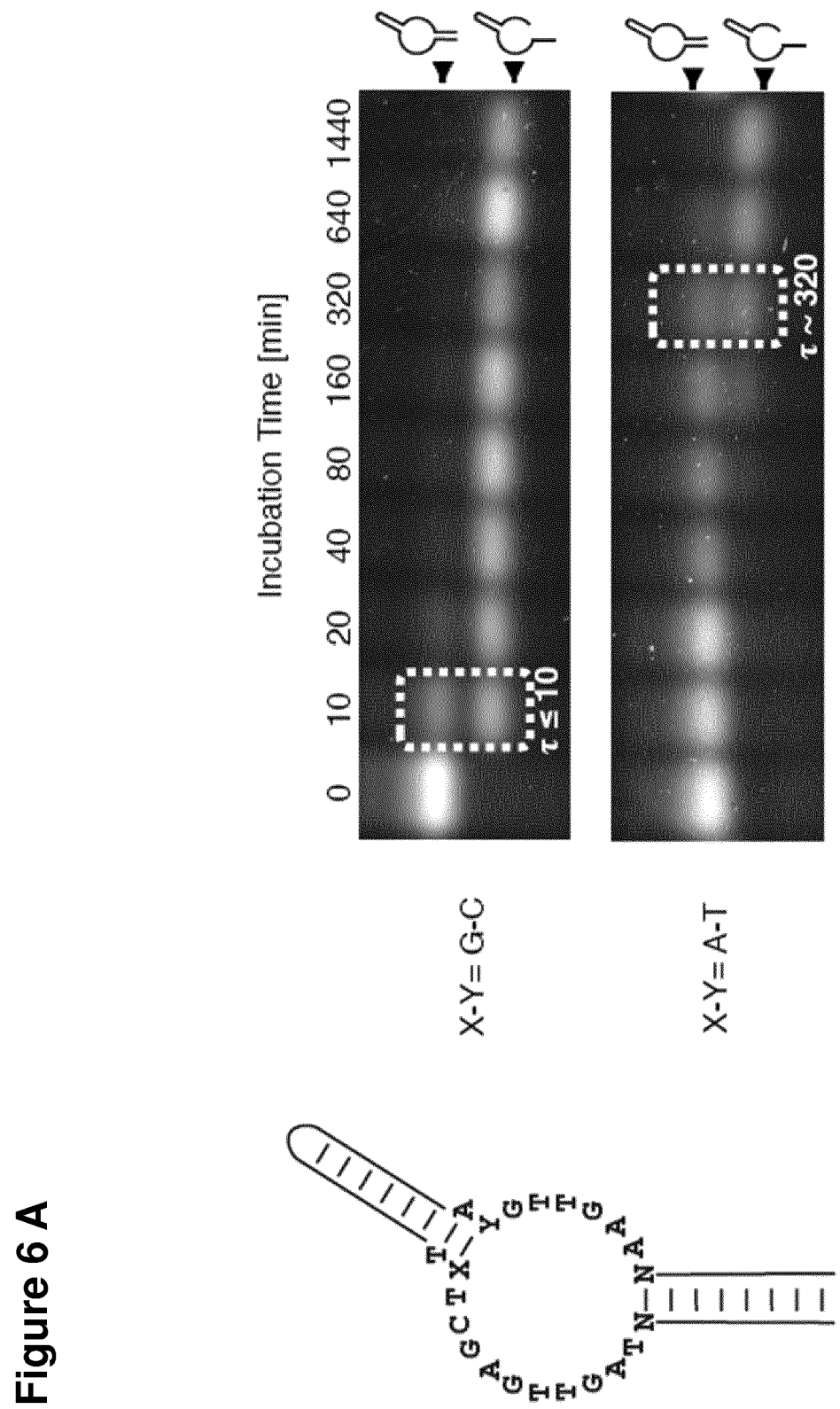
FIG. 6: Optimization of DNAzyme sequences.
- A, left: Schematic representation of a DNAzyme (Type I-R3) (SEQ ID NO: 35). Essential basepairs (as identified in our experiments) are shown as letters, exchangeable basepairs are indicated as lines. The triangle indicates the cleavage position. Right: Gel-electrophoretic analysis of the reaction kinetics of two variants of the DNAzyme differing in one basepair. The slower migrating band corresponds to the uncleaved oligonucleotide, the faster migrating band to the reaction product. τ is defined as the first time point at which the intensity of the product band exceeds the intensity of the uncleaved DNAzyme. The upper gel shows the cleavage of the original sequence as described in Gu et al., 2013, whereas the lower gel shows the cleavage of a variant in which a G-C-basepair is replaced by an A-T basepair. This exchange leads to a significantly lower catalytic activity of the DNAzyme, although this basepair was classified as exchangeable in the original publication by Gu et al.
- B, left: Schematic representation of two phagemids (top: SEQ ID NO: 28; and bottom: SEQ ID NO: 29) containing the staples for the nanorod separated by DNAzymes. Right: Gelelectrophoretic analysis of the digestion kinetics of the two phagemids. The lower variant was designed based on the classification of essential bases from the original publication by Gu et al., whereas the upper variant was designed based on our own findings concerning essential bases. While the upper, optimized variant shows fast and complete cleavage (after 40 minutes basically all DNA is in the bands corresponding to the desired products), the lower variant shows incomplete digestion even after 24 hours of incubation.
Figure 6:
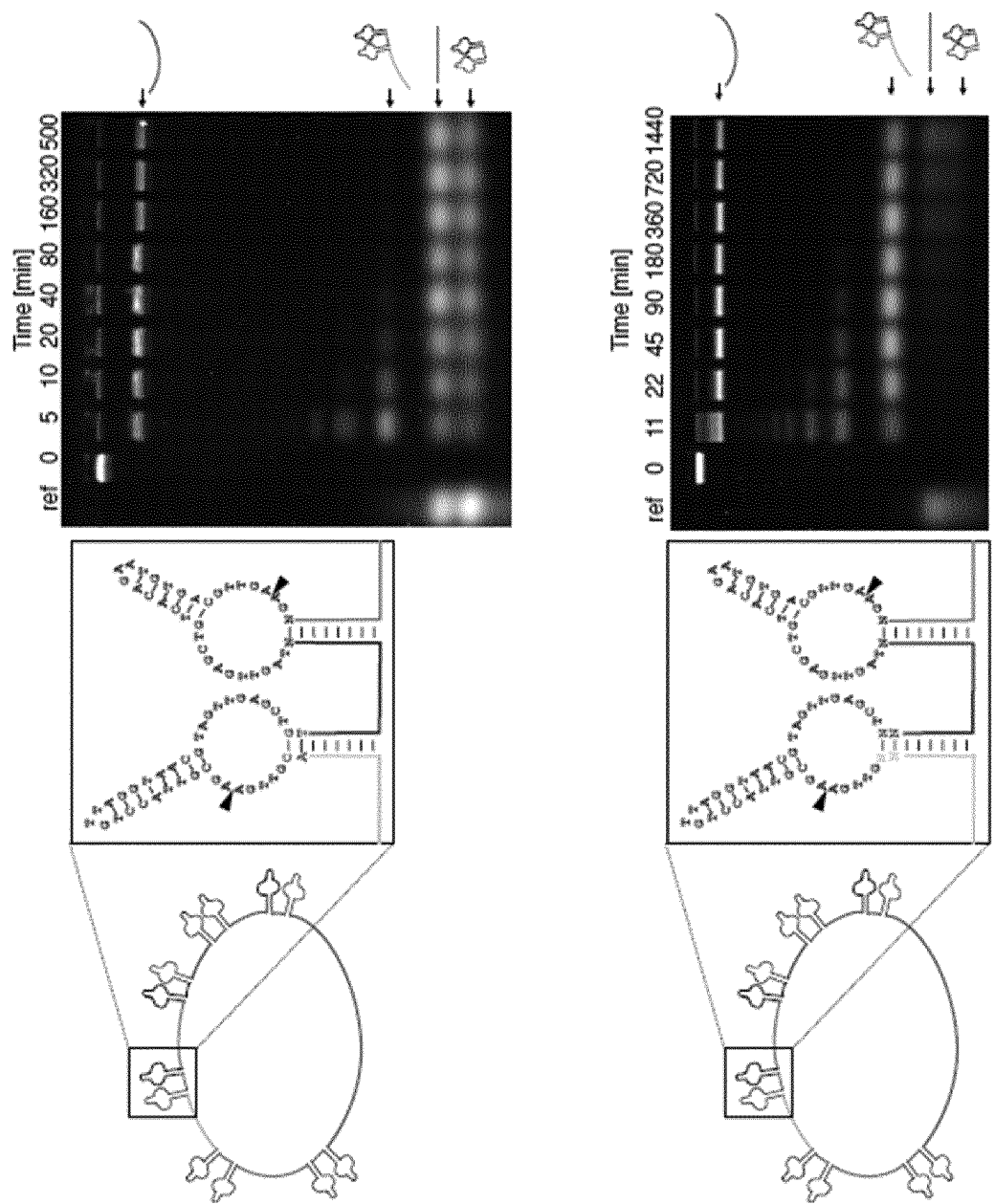

In order to identify the essential bases in the DNAzyme sequence we screened about 40 different variants of individual DNAzymes as oligonucleotides (see FIG. 6A for two examples) and 5 versions of the Full-length phagemid (see FIG. 6B for two examples). We find that some bases that are not classified as essential in the original publication of the DNAzyme (Gu et al., JACS 2013) are indeed essential. This allowed us to construct phagemids that cleaved completely into the desired products in acceptable times (see FIG. 6B).

```
DNAzyme oligonucleotides (as shown in FIG. 6A):
Left:
                                        SEQ ID NO: 35
TTTTTTGCCCTGATAGTTGAGCTXTCACAGAATGTGAYGTTGAAGTCAG
GGCATAAAT Right:
G-C (top):
                                        SEQ ID NO: 26
TTTTTTGCCCTGATAGTTGAGCTGTCACAGAATGTGACGTTGAAGTCAG
GGCATAAAT A-T (bottom):
                                        SEQ ID NO: 27
TTTTTTGCCCTGATAGTTGAGCTaTCACAGAATGTGAtGTTGAAGTCAG
GGCATAAAT
```

```
Phagemids (as shown in FIG. 6B):
Optimized version (top):
                                        SEQ ID NO: 28
ttttccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgccataa ccatgagtgataacactgcggccaacttacttctgacaacgatcggaggaccgaaggagctaaccgcttttttgcacaacatgggggatcatgt aactcgccttgatcgttgggaaccggagctgaatgaagccataccaaacgacgagcgtgacaccacgatgcctgtagcaatggcaacaacgttg cgcaaactattaactggcgaactacttactctagcttcccggcaacaattaatagactggatggaggcggataaagttgcaggaccacttctgc gctcggcccttccggctggctggtttattgctgataaatctggagccggtgagcgtgggtctcgcggtatcattgcagcactggggccagatgg taagccctcccgtatcgtagttatctacacgacggggagtcaggcaactatggatgaacgaaatagacagatcgctgagataggtgcctcactg attaagcattggtaactgtcagaccaagtttactcatatatactttagattgatttaaaacttcatttttaatttaaaaggatctaggtgaaga tcctttttgataatctcatgaccaaaatcccttaacgtgagttttcgttccactgagcgtcagacccgtagaaaagatcaaaggatcttcttg agatccttttttctgcgcgtaatctgctgcttgcaaacaaaaaaaccaccgctaccagcggtggtttgtttgccggatcaagagctaccaact cttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagcttggagcgaacgacctacaccgaactgagatac ctacagcgtgagctatgagaaagcgccacgcttcccgaagggagaaaggcggacaggtatccggtaagcggcagggtcggaacaggagagcgca cgagggagcttccaggggggaaacgcctggtatctttatagtcctgtcgggtttcgccacctctgacttgagcgtcgattttgtgatgctcgtc aggggggcggagcctatggaaaaacgccagcaacgcggccttttttacggttcctggccttttgctggccttttgctcacatgttctttcctgcg ttatcccctgattctgtggataaccgtattaccgcctttgagtgagctgataccgctcgccgcagccgaacgaccgagcgcagcgagtcagtga gcgaggaagcggaagagcgcccaatacgcaaaccgcctctccccgcgcgttggccgattcattaaCTTAATTGCacGTTGAAGCGTTACCTGTT AGGTAACGTAGTTGAGCTgtGCAATTAATTTTTTAAGAGTATAGTTGAGCTGTCACAGAATGTGACGTTGAAGTACTCTTAGAAGTGTCCCAAC TACACTAGAAGGACAGTGGCGAGAGGATTACGCGCCTAGATCAACTTTAATGTTGACTCGTGCACCCAACATGCTTTTTAGCTCACGTTGAAGC GTTACCTGTTAGGTAACGTAGTTGAGCTGTGAGCTAAATTTTTTCAATGTGTAGTTGAGCTGTCACAGAATGTGACGTTGAAGCACATTGAGGG CTGCTATTAAGACACGACTTATCCCTTTCTCAAAAGGCCAGCAAAGCGATCTGGCCCCAATAGGGGAACAAGAGGCAGAACATATCAAAGCGAC GTTGAAGCGTTACCTGTTAGGTAACGTAGTTGAGCTGTCGCTTTGATTTTTTCGGTAAGTAGTTGAGCTGTCACAGAATGTGACGTTGAAGCTT ACCGAGAATAGACACCCGCCTTACAGCGAGGCGAAGGGCTTTAAATCAATCTAGAGCATCATACCAGGCGTTTCGTTCTTGGCGCCGCAACCAC CTGTATGCACGTTGAAGCGTTACCTGTTAGGTAACGTAGTTGAGCTGTGCATACAGTTccTGCGGTCTATAGTTGAGCTGTCACAGAATGTGAC GTTGAAGTAGACCGCGAAAAATGACGGGGAAAGCCTGGCGAATAACTACGTTGCCTGACTCCCGGGGATATTCTCATAGCTCACTAACTATTGT
```

-continued

```
GCTGTAGAGCTCCGTCTACGTTGAAGCGTTACCTGTTAGGTAACGTAGTTGAGCTGTAGACGGAGTTTTTTTGGTCGCTAGTTGAGCTGTCACA
GAATGTGACGTTGAAGGCGACCAAACTCTCAGGGTTATTGTCTGATTTATCGCGTCCGGCGGTGCTACAGACCCCTGGTCCGCCCCCCTGACAA
GTATAAAACCAGCATTTATCAAGGATACGTTGAAGCGTTACCTGTTAGGTAACGTAGTTGAGCTGTATCCTTGATTTTTTGCCCTGATAGTTGA
GCTGTCACAGAATGTGACGTTGAAGTCAGGGCATAAATCGCGTTAATATTTTGCGCGGGGATTAAGTTGCGCCTTATCCGGGCTGTAGTATCCA
CAGAATCACGCGTATGTTTGTCATTGTAAAAAAGAACGTTGAAGCGTTACCTGTTAGGTAACGTAGTTGAGCTGTTCTTTTTTTTTTCACCGA
AGTAGTTGAGCTGTCACAGAATGTGACGTTGAAGCTTCGGTGTTTGGTCCATCCAAAAAGGATCTTCACAGAAAAATGTTTGCAAGCAGCAGTA
TTTCATTCAGAAAGCGGTCTGTGACTGGTGATAACCCAATACTCACGTTGAAGCGTTACCTGTTAGGTAACGTAGTTGAGCTGTGAGTATTGTT
TTTCGCTCCTTTAGTTGAGCTGTCACAGAATGTGACGTTGAAGAAGGAGCGGGAAGGCAATGATGAGGCACCTATCTCAAGGCCACGGATACCT
GTCCGGCCACTGGTGCGGGAGGGAAGCACTATTAAAGAACCAGTTTGGTTCCGCACGTTGAAGCGTTACCTGTTAGGTAACGTAGTTGAGCTGT
GCGGAACCTTTTTTCCTGTAGTAGTTGAGCTGTCACAGAATGTGACGTTGAAGCTACAGGAAGTTGGCTGCATAATTCTCTTTCACCCAAATGCC
GCAAAAAAATTGTTGTGTCACCCAGTTACCTTCGGAAACCACTGATCTTTTCTACGTTAAGGGAGCTAGACGTTGAAGCGTTACCTGTTAGGT
AACGTAGTTGAGCTGTCTAGCTCCTTTTTCCACGCCTTAGTTGAGCTGTCACAGAATGTGACGTTGAAGAGGCGTGGGCGCTCTTCCGATACGG
TGTATCTCAGTTCGGCGACCGCTGGGTAACCCTAAACACTACGTGAACCACCGAAATTCGCGTTACGTTGAAGCGTTACCTGTTAGGTAACGTA
GTTGAGCTGTAACGCGAAccTTTCCTCATGATAGTTGAGCTGTCACAGAATGTGACGTTGAAGTCATGAGGATCCTTCGCTGGTAGCGGTGGCT
GAAGGCTCGTCCCTCCGAATGCCATCCGTAAGTGATCTTAGGGCGACACGGAATCCGCCTATGGCTTGGTATCTACGTTGAAGCGTTACCTGTT
AGGTAACGTAGTTGAGCTGTAGATACCATTTTTGCAAGTTTTAGTTGAGCTGTCACAGAATGTGACGTTGAAGAAACTTGCATAGGCAAGCTCC
CTCGTGCGTATGTACATTCGCTGTAGCGTCTTGCCCGGCGTCGGAAAACGGATACATATTTGAGACCCACGCTGCGCATTAGCACGTTGAAGCG
TTACCTGTTAGGTAACGTAGTTGAGCTGTGCTAATGCTTTTTTGAACGAATAGTTGAGCTGTCACAGAATGTGACGTTGAAGTTCGTTCATGTG
AGCCCTTCGGGAAGCGCCCGGTACGCCAGCGGCGAACCCAACGTCAAAGGGAGATAGGAAAGTGCCACCTAAGTGTAGAAGGGGGACGTCTTGA
CGTTGAAGCGTTACCTGTTAGGTAACGTAGTTGAGCTGTCAAGACGTTTTTTTGCGTCGATAGTTGAGCTGTCACAGAATGTGACGTTGAAGTC
GACGCATGAAGTCGAGCGCCCTTTTTGATCCAGTTCGATGGTACTCACCATGTTGTGCAAACTCCGGTGTCCTGCCTTTTAAATTAAAATCAAG
TCAAACCCGACGTTGAAGCGTTACCTGTTAGGTAACGTAGTTGAGCTGTCGGGTTTGTTTTTCTTTTTATAGTTGAGCTGTCACAGAATGTGA
CGTTGAAGTAAAAAGAATCAGTACCGCGTATGTATTAAGTGCTCATCATTAATACGGAGGGCGCTGGCAAGCATTCAGGCTCACCAGTTACCAA
TGCTTGCCGCGTTGTTCCGACGTTGAAGCGTTACCTGTTAGGTAACGTAGTTGAGCTGTCGGAACAATTTTTGGTCCTGTTAGTTGAGCTGTCA
CAGAATGTGACGTTGAAGACAGGACCTACGGCGATCAAGTGATCCCACCAAGTCATTCTGCTGTTGACAATATTATTGAAGCCAGCCGGCTTAA
TAAGTGGTGGCCTAATATAAAGACAAAAACGTTGAAGCGTTACCTGTTAGGTAACGTAGTTGAGCTGTTTTTGTCTccTTcAGCAGGGTTAGTT
GAGCTGTCACAGAATGTGACGTTGAAGACCCTGCTAACAGGAACTGTTGGGCGCTGATAATACCGCGCCACTTTAATAGAAAAATAAACAAGTG
CTGGCGATCGGCAGCAGCCACTGGCGCTTACGGAACCGACGTTGAAGCGTTACCTGTTAGGTAACGTAGTTGAGCTGTCGGTTCCGTTTTTACA
GAGCGTAGTTGAGCTGTCACAGAATGTGACGTTGAAGCGCTCTGTTTTTAAGGATCTCAAGAAATTATCAGTCTATTGGGAATACAGCATCTT
TTACTTACTGTCTCGTTGTCAGAAGTCATCGTGGCCGGGAATTTTGGACGTTGAAGCGTTACCTGTTAGGTAACGTAGTTGAGCTGTCCAAAAT
TTTTTTGCCTCGCTTAGTTGAGCTGTCACAGAATGTGACGTTGAAGAGCGAGGCTCTCCTGCTGGCGTTTTCGTCTGACGGCTCCACATGAGC
GTTCTTCGGGGCGAGAGTTGCGTCACGCTGCGCGTTACAGGGCAGCAATTATGAGTACGTTGAAGCGTTACCTGTTAGGTAACGTAGTTGAGCT
GTACTCATAAccTTTCCATTGGATAGTTGAGCTGTCACAGAATGTGACGTTGAAGTCCAATGGCGCTACGCAGGAAAGAACATCCATAGATACG
GTCCCCGAGTTGAGTGTTGTTCGTGGACTGTGGCGAGAAAGGACCTCTTCTACCATCTGTCTATACGTTGAAGCGTTACCTGTTAGGTAACGTA
GTTGAGCTGTATAGACAGTTTTTAGGCTGAATAGTTGAGCTGTCACAGAATGTGACGTTGAAGTTCAGCCTGTAGGTACTCAAAGGCGGTACTT
CCTCGCCAACGTTAAAATCGGCAAAATCCCTTGATGGCCGGGAGCCCCCGATTCAAGGCGACGTTGAAGCGTTACCTGTTAGGTAACGTAGTTG
AGCTGTCGCCTTGATTTTTGCTCACATTAGTTGAGCTGTCACAGAATGTGACGTTGAAGATGTGAGCTACAACGTCGTGACTGGGAAAACCCTG
GCGTTACCCAACTTAATCGCCTTGCAGCACATCCCCCTTTCGCCAGCTGGCGTAATAgcgaagaggcccgcaccgatcgcccttcccaacagtt
gcgcagcctgaatggcgaatgggacgcgccctgtagcggcgcattaagcgcggcgggtgtggtggttacgcgcagcgtgaccgctacacttgcc
agcgccctagcgcccgctcctttcgctttcttcccttcctttctcgccacgttcgccggctttccccgtcaagctctaaatcgggggctccctt
```

-continued

```
tagggttccgatttagtgctttacggcacctcgaccccaaaaaacttgattagggtgatggttcacgtagtgggccatcgccctgatagacggt
ttttcgcccttgacgttggagtccacgttcttaatagtggactcttgttccaaactggaacaacactcaaccctatctcggtctattctttt
gatttataagggattttgccgatttcggcctattggttaaaaaatgagctgatttaacaaaaatttaacgcgaattttaacaaaatattaacgc
ttacaatttaggtggcactttcggggaaatgtgcgcggaacccctatttgtttattttctaaatacattcaaatatgtatccgctcatgaga
caataaccctgataaatgcttcaataatattgaaaaaggaagagtatgagtattcaacatttccgtgtcgcccttattccctttttgcggcat
tttgccttcctgttttgctcacccagaaacgctggtgaaagtaaaagatgctgaagatcagttgggtgcacgagtgggttacatcgaactgga
tctcaacagcggtaagatccttgagagttttcgccccgaagaacg
```

Not optimized version (bottom):

SEQ ID NO: 29

```
ttagattgatttaaaacttcattttaatttaaaaggatctaggtgaagatcctttttgataatctcatgaccaaaatcccttaacgtgagttt
tcgttccactgagcgtcagaccccgtagaaaagatcaaaggatcttcttgagatcctttttttctgcgcgtaatctgctgcttgcaaacaaaaa
aaccaccgctaccagcggtggtttgtttgccggatcaagagctaccaactctttttccgaaggtaactggcttcagcagagcgcagataccaaa
tactgtccttctagtgtagccgtagttaggccaccacttcaagaactctgtagcaccgcctacatacctcgctctgctaatcctgttaccagtg
gctgctgccagtggcgataagtcgtgtcttaccgggttggactcaagacgatagttaccggataaggcgcagcggtcgggctgaacggggggtt
cgtgcacacagcccagcttggagcgaacgacctacaccgaactgagatacctacagcgtgagctatgagaaagcgccacgcttcccgaagggag
aaaggcggacaggtatccggtaagcggcagggtcggaacaggagagcgcacgagggagcttccaggggaaacgcctggtatctttatagtcct
gtcgggtttcgccacctctgacttgagcgtcgatttttgtgatgctcgtcaggggggcggagcctatggaaaaacgccagcaacgcggcctttt
tacggttcctggccttttgctggccttttgctcacatgttctttcctgcgttatcccctgattctgtggataaccgtattaccgcctttgagtg
agctgataccgctcgccgcagccgaacgaccgagcgcagcgagtcagtgagcgaggaagcggaagagcgcccaatacgcaaaccgcctctcccc
gcgcgttggccgattcattaaCTTAATTGCgttgAAGCGTTACCTGTTAGGTAACGTAGTTGAGCTGCAATTAATTTTTTAAGAGTATAGTTGA
GCTGTCACAGAATGTGACGTTGAAGTACTCTTAGAAGTGTCCCAACTACACTAGAAGGACAGTGGCGAGAGGATTACGCGCCTAGATCAACTTT
AATGTTGACTCGTGCACCCAACATGCTTTTTAGCTCGTTGAAGCGTTACCTGTTAGGTAACGTAGTTGAGCTGAGCTAAATTTTTTCAATGTGT
AGTTGAGCTGTCACAGAATGTGACGTTGAAGCACATTGAGGGCTGCTATTAAGACACGACTTATCCCTTTCTCAAAAGGCCAGCAAAGCGATCT
GGCCCCAATAGGGGAACAAGAGGCAGAACATATCAAAGCGAGTTGAAGCGTTACCTGTTAGGTAACGTAGTTGAGCTTCGCTTTGTTTTTTCGG
TAAGTAGTTGAGCTGTCACAGAATGTGACGTTGAAGCTTACCGAGAATAGACACCCGCCTTACAGCGAGGCGAAGGGCTTTAAATCAATCTAGA
GCATCATACCAGGCGTTTCGTTCTTGGCGCCGCAACCACCTGTATGCGTTGAAGCGTTACCTGTTAGGTAACGTAGTTGAGCTGCATACAGTTT
TTGCGGTCTATAGTTGAGCTGTCACAGAATGTGACGTTGAAGTAGACCGCGAAAAATGACGGGGAAAGCCTGGCGAATAACTACGTTGCCTGAC
TCCCGGGGATATTCTCATAGCTCACTAACTATTGTGCTGTAGAGCTCCGTCAGTTGAAGCGTTACCTGTTAGGTAACGTAGTTGAGCTTAGAC
GGATTTTaTTGGTCGCTAGTTGAGCTGTCACAGAATGTGACGTTGAAGGCGACCAAACTCTCAGGGTTATTGTCTGATTTATCGCGTCCGGCGG
TGCTACAGACCCCTGGTCCGCCCCCCTGACAAGTATAAAACCAGCATTTATCAAGGATGTTGAAGCGTTACCTGTTAGGTAACGTAGTTGAGCT
ATCCTTGATTTTTTGCCCTGATAGTTGAGCTGTCACAGAATGTGACGTTGAAGTCAGGGCATAAATCGCGTTAATATTTTGCGCGGGGATTAAG
TTGCGCCTTATCCGGGCTGTAGTATCCACAGAATCACGCGTATGTTTGTCATTGTAAAAAAGAAGTTGAAGCGTTACCTGTTAGGTAACGTAGT
TGAGCTTTCTTTTTTTTTTCACCGAAGTAGTTGAGCTGTCACAGAATGTGACGTTGAAGCTTCGGTGTTTGGTCCATCCAAAAAGGATCTTCAC
AGAAAAATGTTTGCAAGCAGCAGTATTTCATTCAGAAAGCGGTCTGTGACTGGTGATAACCCAATACTCAGTTGAAGCGTTACCTGTTAGGTAA
CGTAGTTGAGCTTGAGTATTTTTTTCGCTCCTTTAGTTGAGCTGTCACAGAATGTGACGTTGAAGAAGGAGCGGGAAGGCAATGATGAGGCACC
TATCTCAAGGCCACGGATACCTGTCCGGCCACTGGTGCGGGAGGGAAGCACTATTAAAGAACCAGTTTGGTTCCGCGTTGAAGCGTTACCTGTT
AGGTAACGTAGTTGAGCTGCGGAACCTTTTaTCCTGTAGTAGTTGAGCTGTCACAGAATGTGACGTTGAAGCTACAGGAAGTTGGCTGCATAAT
TCTCTTTCACCAAATGCCGCAAAAAAAATTGTTGTGTCACCCAGTTACCTTCGGAAACCACTGATCTTTTCTACGTTAAGGGAGCTAGAGTTGA
AGCGTTACCTGTTAGGTAACGTAGTTGAGCTTCTAGCTCTTTTTCCACGCCTTAGTTGAGCTGTCACAGAATGTGACGTTGAAGAGGCGTGGGC
GCTCTTCCGATACGGTGTATCTCAGTTCGGCGACCGCTGGGTAACCCTAAACACTACGTGAACCACCGAAATTCGCGTTGTTGAAGCGTTACCT
GTTAGGTAACGTAGTTGAGCTAACGCGAAaTTaCCTCATGATAGTTGAGCTGTCACAGAATGTGACGTTGAAGTCATGAGGATCCTTCGCTGG
TAGCGGTGGCTGAAGGCTCGTCCCTCCGAATGCCATCCGTAAGTGATCTTAGGGCGACACGGAATCCGCCTATGGCTTGGTATCTGTTGAAGCG
```

-continued

Figure 7:
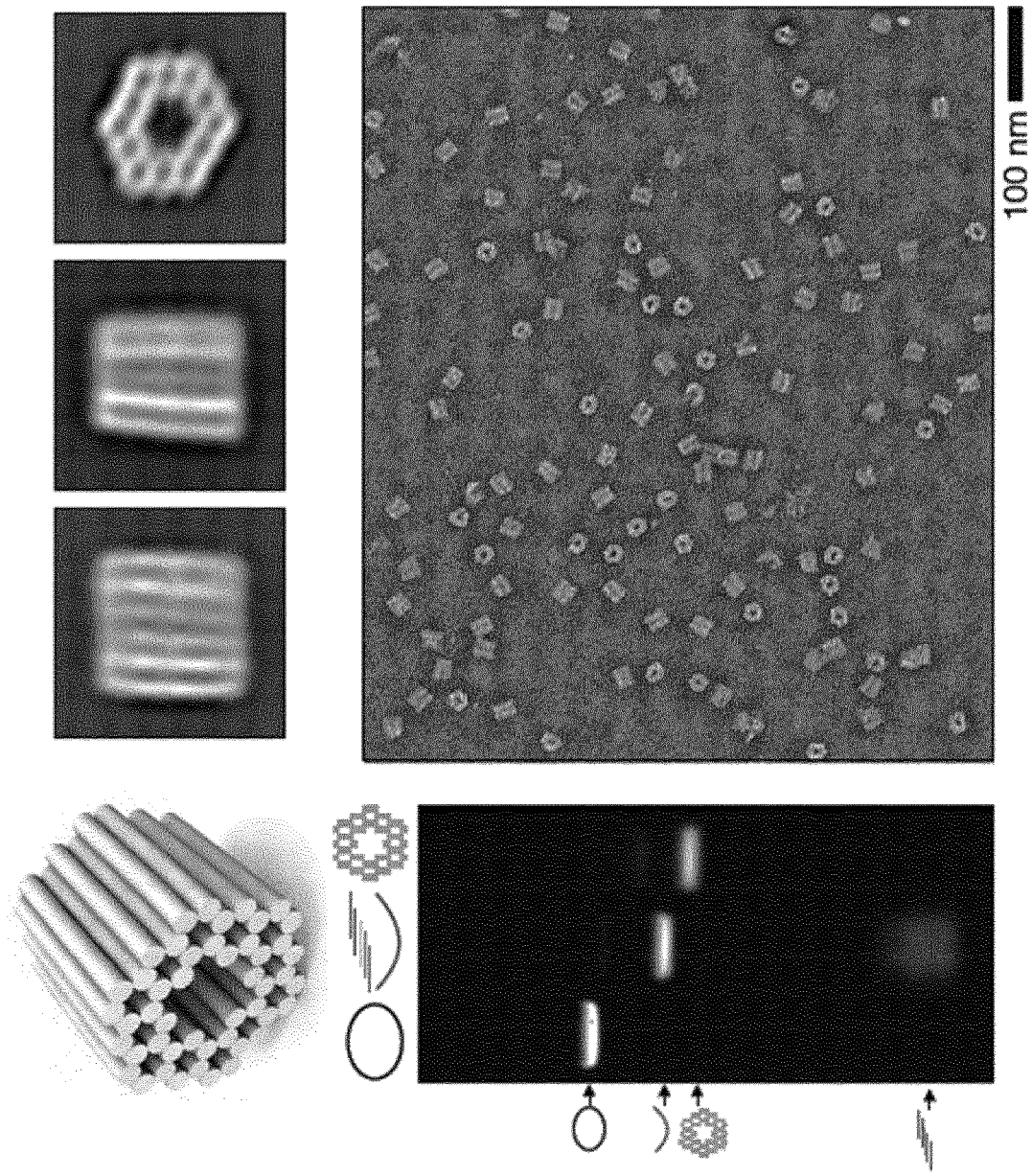
FIG. 7: Nanostructures assembled from DNA oligonucleotides produced using the DNAzyme-based method of the invention.
- A, Top left: Schematic representation of a 48-helix-tube assembled from a 3200 bases long scaffold and 31 staple oligonucleotides that are all contained in one phagemid. Bottom left: Image of an agarose gel in which the undigested phagemid (left), the digested phagemid (center) and the folded 48-helix tube (right) have been electrophoresed. Right: Negative stain transmission electron micrograph (bottom) and class averages (top) of the 48-helix-tube.
- B, Top left: schematic representation of a pointer object assembled from a 7249 bases long M13-scaffold and 161 staple oligonucleotides. Bottom left: Image of an agarose gel in which the scaffold (left) and structures assembled using chemically synthesized (center) or biotechnologically produced (right) staples have been electrophoresed. Right: Negative stain transmission electron micrograph and class average (inset) of the pointer object.
Figure 7:
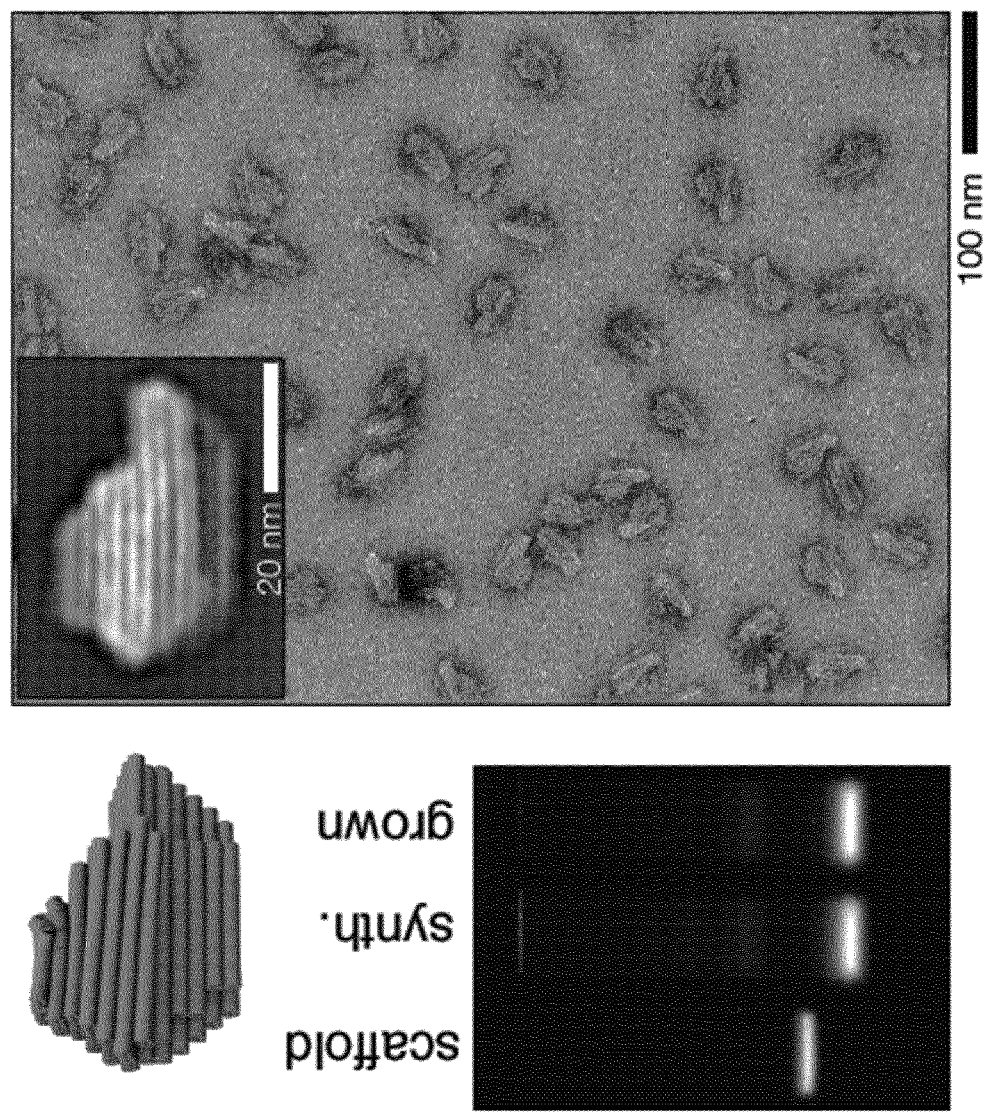

TTACCTGTTAGGTAACGTAGTTGAGCTAGATACCATTTTaGCAAGTTTTAGTTGAGCTGTCACAGAATGTGACGTTGAAGAAACTTGCATAGGC
AAGCTCCCTCGTGCGTATGTACATTCGCTGTAGCGTCTTGCCCGGCGTCGGAAAACGGATACATATTTGAGACCCACGCTGCGCATTAGCAGTT
GAAGCGTTACCTGTTAGGTAACGTAGTTGAGCTTGCTAATGTTTTTTGAACGAATAGTTGAGCTGTCACAGAATGTGACGTTGAAGTTCGTTCA
TGTGAGCCCTTCGGGAAGCGCCCGGTACGCCAGCGGCGAACCCAACGTCAAAGGGAGATAGGAAAGTGCCACCTAAGTGTAGAAGGGGGACGTC
TTGGTTGAAGCGTTACCTGTTAGGTAACGTAGTTGAGCTCAAGACGTTTTTTTGCGTCGATAGTTGAGCTGTCACAGAATGTGACGTTGAAGTC
GACGCATGAAGTCGAGCGCCCTTTTTGATCCAGTTCGATGGTACTCACCATGTTGTGCAAACTCCGGTGTCCTGCCTTTTAAATTAAAATCAAG
TCAAACCCGGTTGAAGCGTTACCTGTTAGGTAACGTAGTTGAGCTCGGGTTTGTTTTaTCTTTTTATAGTTGAGCTGTCACAGAATGTGACGTT
GAAGTAAAAAGAATCAGTACCGCGTATGTATTAAGTGCTCATCATTAATACGGAGGGCGCTGGCAAGCATTCAGGCTCACCAGTTACCAATGCT
TGCCGCGTTGTTCCGGTTGAAGCGTTACCTGTTAGGTAACGTAGTTGAGCTCGGAACAATTTTTGGTCCTGTTAGTTGAGCTGTCACAGAATGT
GACGTTGAAGACAGGACCTACGGCGATCAAGTGATCCCACCAAGTCATTCTGCTGTTGACAATATTATTGAAGCCAGCCGGCTTAATAAGTGGT
GGCCTAATATAAAGACAAAAAGTTGAAGCGTTACCTGTTAGGTAACGTAGTTGAGCTTTTTTGTCaaTTaAGCAGGGTTAGTTGAGCTGTCACA
GAATGTGACGTTGAAGACCCTGCTAACAGGAACTGTTGGGCGCTGATAATACCGCGCCACTTTAATAGAAAAATAAACAAGTGCTGGCGATCGG
CAGCAGCCACTGGCGCTTACGGAACCGGTTGAAGCGTTACCTGTTAGGTAACGTAGTTGAGCTCGGTTCCGaTTTTACAGAGCGTAGTTGAGCT
GTCACAGAATGTGACGTTGAAGCGCTCTGTTTTTAAGGATCTCAAGAAATTATCAGTCTATTGGGAATACAGCATCTTTTACTTACTGTCTCG
TTGTCAGAAGTCATCGTGGCCGGGAATTTTGGGTTGAAGCGTTACCTGTTAGGTAACGTAGTTGAGCTCCAAAATTTTTTGCCTCGCTTAGTT
GAGCTGTCACAGAATGTGACGTTGAAGAGCGAGGCTCTCCTGCTGGCGTTTTCGTCTGACGGCTCCACATGAGCGTTCTTCGGGGCGAGAGTT
GCGTCACGCTGCGCGTTACAGGGCAGCAATTATGAGTGTTGAAGCGTTACCTGTTAGGTAACGTAGTTGAGCTACTCATAaTTTCCATTGGAT
AGTTGAGCTGTCACAGAATGTGACGTTGAAGTCCAATGGCGCTACGCAGGAAAGAACATCCATAGATACGGTCCCCGAGTTGAGTGTTGTTCGT
GGACTGTGGCGAGAAAGGACCTCTTCTACCATCTGTCTATGTTGAAGCGTTACCTGTTAGGTAACGTAGTTGAGCTATAGACAGTTTTTAGGCT
GAATAGTTGAGCTGTCACAGAATGTGACCTTGAAGTTCAGCCTGTAGGTACTCAAAGGCGGTACTTCCTCGCCAACGTTAAAATCGGCAAAATC
CCTTGATGGCCGGGAGCCCCCGATTCAAGGCGGTTGAAGCGTTACCTGTTAGGTAACGTAGTTGAGCTCGCCTTGATTTTTGCTCACATTAGTT
GAGCTGTCACAGAATGTGACGTTGAAGATGTGAGCtacaacgtcgtgactgggaaaaccctggcgttacccaacttaatcgccttgcagcacat
ccccctttcgccagctggcgtaatagcgaagaggcccgcaccgatcgcccttcccaacagttgcgcagcctgaatggcgaatgggacgcgccct
gtagcggcgcattaagcgcggcgggtgtggtggttacgcgcagcgtgaccgctacacttgccagcgccctagcgcccgctcctttcgctttctt
cccttcctttctcgccacgttcgccggctttccccgtcaagctctaaatcggggggctcccttagggttccgatttagtgctttacggcacctc
gaccccaaaaaacttgattagggtgatggttcacgtagtgggccatcgccctgatagacggttttcgccctttgacgttggagtccacgttct
ttaatagtggactcttgttccaaactggaacaacactcaaccctatctcggtctattcttttgatttataagggattttgccgatttcggccta
ttggttaaaaaatgagctgatttaacaaaaatttaacgcgaattttaacaaaatattaacgcttacaatttaggtggcacttttcggggaaatg
tgcgcggaacccctatttgttatttttctaaatacattcaaatatgtatccgctcatgagacaataaccctgataaatgcttcaataatattg
aaaaaggaagagtatgagtattcaacatttccgtgtcgcccttattccctttttgcggcattttgccttcctgtttttgctcacccagaaacg
ctggtgaaagtaaaagatgctgaagatcagttgggtgcacgagtgggttacatcgaactggatctcaacagcggtaagatccttgagagttttc
gccccgaagaacgttttccaatgatgagcacttttaaagttctgctatgtggcgcggtattatcccgtattgacgccgggcaagagcaactcgg
tcgccgcatacactattctcagaatgacttggttgagtactcaccagtcacagaaaagcatcttacggatggcatgacagtaagagaattatgc
agtgctgccataaccatgagtgataacactgcggccaacttacttctgacaacgatcggaggaccgaaggagctaaccgcttttttgcacaaca
tgggggatcatgtaactcgccttgatcgttgggaaccggagctgaatgaagccataccaaacgacgagcgtgacaccacgatgcctgtagcaat
ggcaacaacgttgcgcaaactattaactggcgaactacttactctagcttcccggcaacaattaatagactggatggaggcggataaagttgca
ggaccacttctgcgctcggcccttccggctggctggtttattgctgataaatctggagccggtgagcgtgggtcAcgcggtatcattgcagcac
tggggccagatggtaagccctcccgtatcgtagttatctacacgacggggagtcaggcaactatggatgaacgaaatagacagatcgctgagat
aggtgcctcactgattaagcattggtaactgtcagaccaagtttactcatatatact Example 3 Further Nanostructures Assembled from DNA Oligonucleotides Produced Using the DNAzyme-Based Method of the Invention In addition to the nanorod, we designed a 48-helix tube that assembles from a 3200 bases long scaffold and 31 staple oligonucleotides (see FIG. 7A). As for the nanorod, all staples for this 48-helix-tube are encoded on one phagemid, and the backbone of the phagemid serves as scaffold. Like the nanorod, this object assembles efficiently into the desired shape without using an excess of staples over scaffold, due to the intrinsically perfect 1:1 stoichiometry.

In order to demonstrate the applicability of our method to the assembly of existing, full-size DNA origami objects, we produced phagemids encoding for all 161 staple oligonucleotides that are needed for the assembly of a pointer object (see FIG. 7B) that was previously used in cryo electron microscopy studies (Bai et al., 2012). In contrast to the nanorod and the 48-helix-bundle, the staples for the pointer are distributed over four individual phagemids, and a separate scaffold (M13mp18, 7249 bases long, same sequence as was used in the original study by Bai et al.) is used. To compensate uncertainties in relative concentrations we used a slight excess of staples over scaffold (1.25 to 1). In comparison, the assembly using the chemically synthesized staples required a larger excess of 2.5 to 1.

```
                          Phagemid sequences
48 helix tube (FIG. 7A):
                                                          SEQ ID NO: 30
gacgtaacggtgctgtctaacatcgagactgcaattacccgccagacctttgcacttccacactaatttggtcgatctttgcttaaccgggaa ctatgtagtctatatgagaatattgagcataaggtgtcagccagcctttatccttgaggcagatcaggtctattcgctcagagtaagatgctaa cacccagtagatgacgacgtttaattagggccgagagaccaatgtcacgcattaagcgcggcgggtgtggtggttacgcgcagcgtgaccgcta cacttgccagcgccctagcgcccgctcctttcgctttcttccttccttctcgccacgttcgccggctttccccgtcaagctctaaatcggg gctcccttagggttccgatttagtgctttacggcacctcgacccaaaaaacttgattagggtgatggttcacgtagtgggccatcgccctga tagacggttttcgccctttgacgttggagtccacgttctttaatagtggactcttgttccaaactggaacaacactcaaccctatctcggtct attcttttgatttataagggattttgccgatttcggcctattggttaaaaaatgagctgatttaacaaaaatttaacgcgaattttaacaaaat attaacgcttacaatttaggtggcacttttcggggaaatgtgcgcggaaccTTGATCGGGCACGTAAGAGgttccaactttcaccataatgaaa taagatcactaccgggcgtattttttgagttatcgagattttcaggagctaaggaagctaaaatggagaaaaaaatcactggatataccaccgt tgatatatcccaatggcatcgtaaagaacattttgaggcatttcagtcagttgctcaatgtacctataaccagaccgttcagctggatattacg gccttttaaagaccgtaaagaaaaataagcacaagttttatccggcctttattcacattcttgcccgcctgatgaatgctcatccggaatttc gtatggcaatgaaagacggtgagctggtgatatgggatagtgttcaccttgttacaccgttttccatgagcaaactgaaacgttttcatcgct ctggagtgaataccacgacgatttccggcagtttctacacatatattcgcaagatgtggcgtgttacggtgaaaacctggcctatttccctaaa gggtttattgagaatatgttttcgtctcagccaatccctgggtgagtttcaccagttttgatttaaacgtggccaatatggacaacttcttcg cccccgttttcaccatgggcaaatattatacgcaaggcgacaaggtgctgatgccgctggcgattcaggttcatcatgccgtttgtgatggctt ccatgtcggcagaatgcttaatgaattacaacagtactgcgatgagtggcagggcggggcgtaatttgatatcgagctcgcttggactcctgtt gatagatccagtaatgacctcagaactccatctggatttgttcagaacgctcggttgccgccgggcgttttttattggtgagaatccaagcctc gagctgtcagaccaagtttactcatatatactttagattgatttaaaacttcattttttaatttaaaaggatctaggtgaagatccttttttgata atctcatgaccaaaatcccttaacgtgagttttcgttccactgagcgtcagacccctagaaaagatcaaaggatcttcttgagatccttttt tctgcgcgtaatctgctgcttgcaaacaaaaaaaccaccgctaccagcggtggtttgtttgccggatcaagagctaccaactcttttccgaag gtaactggcttcagcagagcgcagataccaaatactgtTcttctagtgtagccgtagttaggccaccacttcaagaactctgtagcaccgccta catcctcgctctgctaatcctgttaccagtggctgctgccagtggcgataagtcgtgtcttaccgggttggactcaagacgatagttaccgga taaggcgcagcggtcgggctgaacggggggttcgtgcacacagcccagcttggagcgaacgacctacaccgaactgagatacctacagcgtgag ctatgagaaagcgccacgcttcccgaagggagaaaggcggacaggtatccggtaagcggcagggtcggaacaggagagcgcacgagggagcttc caggggggaaacgcctggtatctttatagtcctgtcgggtttcgccacctctgacttgagcgtcgatttttgtgatgctcgtcaggggggcggag cctatggaaaaacgccagcaacgcggcctttttacggttcctggccttttgctggccttttgctcaccttagcaagagccgcacgacgaccaga ggccagttatccagagttaggatacctcaatgtgcatccgctcggttctaaggacattatttcagtccttttaagatctcccgtatagaagcctc acgttaggggggcgccgtgccttcacgccctcccatttaggaataccttgtctccgccgtctttattcagtagccctatgcattacgatgtggcg cttccccccgcgtgggcgcagaaatttactgaggcggattcgaaacgactgtgagggcaggataggtgagcaggcactggcacgtaatcaaccaa cggactcaccgtgtgcaggcctaaaaacagccctcgaagggcacttggatatgaatgaacccacttgttttgactcgtggaggcgtggtttta
```

| Phagemid sequences |
|---|
| ttactgtgctcagttaacgccgcatgaatttagctctgatcaccgtaagggtaactgcactagacatgttgtgggcatttaagtcctgcagtat |
| cttttgttaggtggaacggcctaggggtaccttccgtgagaaactcccagatgatgcatgttcgagtacttgtgaaatggatggtcgcatccc |
| ctcctctcacacattacactgtctcgcgcgggttgcgtcttgaccggtacaagttgtgtaaccttacacctctagaaacattttagcagtcgct |
| ccaattgataccacgacctcagcgcgcgttgggagaccgttgccaaaCCTAGACGTTGAAGCGTTACCTGTTAGGTAACGTAGTTGAGCTGTCT |
| AGGTTTTTTTTGCATCTGGTAGTTGAGCTGTCACAGAATGTGACGTTGAAGCCAGATGCACCAATGTATATAAATAGATCCTTTTAAATTAAAT |
| AAATCAATCGTAATACTGAACTAGGTTCTCCCAAGGTGTAACCGTAAACCGCCCCACGTTGAAGCGTTACCTGTTAGGTAACGTAGTTGAGCTG |
| TGGGGCGGTTTTTTAATCCAAGTAGTTGAGCTGTCACAGAATGTGACGTTGAAGCTTGGATTCTGAGTTCTGCACGGCTCAATTCGCGTTAAAT |
| TTTTGGCGAGGGCGTGAAGGAGGTCATTACTGGTAAGCTCGAGGACGTTGAAGCGTTACCTGTTAGGTAACGTAGTTGAGCTGTCCTCGAGCTT |
| TTTCCCGTAGATAGTTGAGCTGTCACAGAATGTGACGTTGAAGTCTACGGGGTCTATAATATTTGAAGTTGTGGCCCAAGTTTTTTGGGGTCAA |
| GGGAGTTTTCGGAAAAAGAGAAACTCTGGCCACACGTTGAAGCGTTACCTGTTAGGTAACGTAGTTGAGCTGTGTGGCCAGTTTTTAAAAAAAA |
| TAGTTGAGCTGTCACAGAATGTGACGTTGAAGTTTTTTTTTTTTTTTTAGGATCTATTACGCTTTTTTTTTTTTTTTTTGCCTGCAT |
| CGAGGGTTTTTTTTTTTTTTTTTACGTTGAAGCGTTACCTGTTAGGTAACGTAGTTGAGCTGTAAAAAAAATTTTTTACCGCTATAGTTGA |
| GCTGTCACAGAATGTGACGTTGAAGTAGCGGTAAACAAAACAAGTGCGCCTCCTGCAGTTGCCCACACAAAAAGCACGAACTTCTCATAGCTCA |
| CTCTCCCTCATCCATCAGTGTACGGTCAATTCTAGACGCGCGCACGTTGAAGCGTTACCTGTTAGGTAACGTAGTTGAGCTGTGCGCGTTTT |
| TTGAGGGTTTTAGTTGAGCTGTCACAGAATGTGACGTTGAAGAAACCCTCCCCCGAGCGAACGTGGCGCGCTCCAGATGCGAATATATGTGAAG |
| CCAGTTACCAGGGAAATACACATCTGCGATGAACGTTGAAGCGTTACCTGTTAGGTAACGTAGTTGAGCTGTTCATCGCATTTTTATACTGTTT |
| AGTTGAGCTGTCACAGAATGTGACGTTGAAGAACAGTATACGGCTAGAGTTCTATGTAGCAACCCGAACTATCGCCCGACCGCTGCGCTGTGTG |
| ATACTGCGTACCCCTAGGCCGATGCGACTCGGGAAAAGCTCCACGTTGAAGCGTTACCTGTTAGGTAACGTAGTTGAGCTGTGGAGCTTTTTT |
| TCGCGTGTTTAGTTGAGCTGTCACAGAATGTGACGTTGAAGAACACGCGGCCAGGTCTCAATTGAGACGGGGCGAAGCCCATGCCTTGTCGCCT |
| TGCCCTGAATTATCAGGGGACTCCACGTTGAAGCGTTACCTGTTAGGTAACGTAGTTGAGCTGTGGAGTCCCTTTTTAGTTTCTATAGTTGAGC |
| TGTCACAGAATGTGACGTTGAAGTAGAAACTGCCGTGGCCTAACTTTGGTAATCCGGCGGTTTTTTGTTAAAACTGGTGTTGGTAAAATCGGA |
| CGTTGAAGCGTTACCTGTTAGGTAACGTAGTTGAGCTGTCCGATTTTTTTTTTTCCATGTAGTTGAGCTGTCACAGAATGTGACGTTGAAGCA |
| TGGAAAAACGTTAAAGCCGTTTAGAGCTAATCACTACGTGAACCGTCCGCCAGCACTGTTGTAATTCACCCCGCCATAGGGTAATCCCTTCTCG |
| ATGAAGTGCAGCAAAGGTGATCTCCTTAGCACGTTGAAGCGTTACCTGTTAGGTAACGTAGTTGAGCTGTGCTAAGGATTTTTACACCGTTTAG |
| TTGAGCTGTCACAGAATGTGACGTTGAAGAACGGTGTAACAGCCACTGGTGTATTCAGCGTTAAAACCCTAGAGGTGCATTACGTGCCAGGATC |
| CATATACCCAGGGATTGGCACGTTGAAGCGTTACCTGTTAGGTAACGTAGTTGAGCTGTGCCAATCCTTTTAAAAAAAATAGTTGAGCTGTCA |
| CAGAATGTGACGTTGAAGTTTTTTTTTTTTTTTTCACCGTCATCCCATTTTTTTTTTTTTTTTTGGGCGCTAAGAAAGTTTTTTT |
| TTTTTTTTTTTACGTTGAAGCGTTACCTGTTAGGTAACGTAGTTGAGCTGTAAAAAAATTTTTCTCATCCGTAGTTGAGCTGTCACAGAATG |
| TGACGTTGAAGCGGATGAGCATTTTATCCGGTGTAAGACCTTAAATACCCTTACGGTGATCAGTAATGGGAAATCGTCGTGAACAGGAATCGCC |
| AACGTTGAAGCGTTACCTGTTAGGTAACGTAGTTGAGCTGTTGGCGATTTTTTCTGGAGCGTAGTTGAGCTGTCACAGAATGTGACGTTGAAG |
| CGCTCCAGTATCTCAGTTCGGTACCGGAAACATGCGATAAAGGCTGGCGGTCAGAGGTGGCACAATCTCGATAACCGTTTTCCCGCTCAACGC |
| GAGATTCACAAACGGAAGAGGTAACCACCACAACGTTGAAGCGTTACCTGTTAGGTAACGTAGTTGAGCTGTGTGGTGGTTTTTAACAGGTAT |
| AGTTGAGCTGTCACAGAATGTGACGTTGAAGTACCTGTTGTTCCGACCCTGCCAGAAACCCGACAGGACTATAGCTCTCCCCGCCTTGCTGTAG |
| AGCTGGGCCCATCAGGCGGGCAAGAATGGGTCGTTCCCGCCGTCTGGGAGTTTCTCGTACTCGACGTTGAAGCGTTACCTGTTAGGTAACGTAG |
| TTGAGCTGTCGAGTACGTTTTTTGCACGAGTAGTTGAGCTGTCACAGAATGTGACGTTGAAGCTCGTGCAAGATACAAATCGAATAGGCTAAGG |
| CCGAAAAGGCGGATAACTGGCCTCTAGAACCTGAGGTCGAAATCTTCAACGTTAAAGACAACGTGAAACAAATACGTTGAAGCGTTACCTGTTA |
| GGTAACGTAGTTGAGCTGTATTTGTTTTTTTCTTCAGGATAGTTGAGCTGTCACAGAATGTGACGTTGAAGTCCTGAAGGTGGTACCTCAAGA |
| TACTGGGTGTTAGGGTACATTGAGCCTTGAAAGGCCGTAATATCCAGCGGTTATACATCTTAATAGACCTATAGACCCGGTTAAAAGGTCCCAC |

| Phagemid sequences |
|---|
| CTAAGCTCATACGTTGAAGCGTTACCTGTTAGGTAACGTAGTTGAGCTGTATGAGCTTTTTTCCTCCGCTTAGTTGAGCTGTCACAGAATGTG |
| ACGTTGAAGAGCGGAGGACTGAAATAATGGCCCCCTGGCGGAGACGGGAAGCGCCACATCTAAAAAAAAACGCCCGGCCGTTCTGGGCTTCTTC |
| TTAAATGCACATTAACTCTCAGCAAAACGTTGAAGCGTTACCTGTTAGGTAACGTAGTTGAGCTGTTTTGCTGATTTTTAACCTGTTAGTTGA |
| GCTGTCACAGAATGTGACGTTGAAGACAAGGTTTACGTCGTGGTATCAATTATATATTTTGTTAACTTGGTCGTCGTGCATCAAGGTTAGCGTT |
| ATAGTGTGGTTAGACACGTTGAAGCGTTACCTGTTAGGTAACGTAGTTGAGCTGTGTCTAACCTTTTTCTGACGTTTAGTTGAGCTGTCACAGA |
| ATGTGACGTTGAAGAACGTCAGACCGAGCTGCCACGCTCGATATCAAATATCTATCGAAATCGTTAAATCAATTGTACCGCGCAACCTCTTACG |
| TGCCCCCGGTAATCGACCGCTCAATACGTTGAAGCGTTACCTGTTAGGTAACGTAGTTGAGCTGTATTGAGCGTTTTTATTAATAGTAGTTGAG |
| CTGTCACAGAATGTGACGTTGAAGCTATTAATGTTCCAACTTGGTCTGACCGTTAAGCATGATGAAGTGACGCTCAGTGGAACGAAACATCACA |
| TATCCTGGAGTCCAACGTTGAAGCGTTACCTGTTAGGTAACGTAGTTGAGCTGTTGGACTCCTTTTTTGATTCGATAGTTGAGCTGTCACAGAA |
| TGTGACGTTGAAGTCGAATCAATTTCTGCGCCCACGCGGAACCCTCACGAGTCCGTCTGCAAGCAGCAGCAAGAAGTTAAGGGATTTTGGATCA |
| AAAACGTTGAAGCGTTACCTGTTAGGTAACGTAGTTGAGCTGTTTTTGATCTTTTTGCTTTACGTAGTTGAGCTGTCACAGAATGTGACGTTGA |
| AGCGTAAAGCATCCAAGTGCCCTCACGGGTAGTCGTTAGGATCTTCACCGCACTCACGATCCTTTGATCTTTGTTTAAATTGGTTGACGTTGAA |
| GCGTTACCTGTTAGGTAACGTAGTTGAGCTGTCAACCAATTTTTTGTGCTCAGTAGTTGAGCTGTCACAGAATGTGACGTTGAAGCTGAGCACA |
| GAGCTGTCACGCTGCGCGAACGACTTTTAGCAGAGCGAGGTTGAAGTAAAACCAGGTTCATTCATACTGCTCTTGTCTGCGCTCTGCTGACGTT |
| GAAGCGTTACCTGTTAGGTAACGTAGTTGAGCTGTCAGCAGAGTTTTTATGAATTTTAGTTGAGCTGTCACAGAATGTGACGTTGAAGAAATTC |
| ATGAGAAAGGAAGGGAGGGCGCTGCGTGATACGGTCTTTAATATGAATAAGCCATACGAAATTCCTGGCAGTGTAGCGACGTTGAAGCGTTACC |
| TGTTAGGTAACGTAGTTGAGCTGTCGCTACACTTTTTATTAAGCGTAGTTGAGCTGTCACAGAATGTGACGTTGAAGCGCTTAATGGCAAGCAA |
| GGGTGAACACTTTTCATTAGGCCGGATAAAACTTTTCTTCATTGGTTAATTAAACGTCGTCATCTCAACGTTGAAGCGTTACCTGTTAGGTAAC |
| GTAGTTGAGCTGTTGAGATGATTTTTATGAGAATTAGTTGAGCTGTCACAGAATGTGACGTTGAAGATTCTCATGATCTGTATCCAGCCATTGG |
| GATATATCGAACTGACTGAAATGCCTCATACGATGTGATTTTTAGCTTTATTTCAAGTTGGACATTTCCACGTTGAAGCGTTACCTGTTAGGT |
| AACGTAGTTGAGCTGTGGAAATGTTTTTTGGTTGCGTTAGTTGAGCTGTCACAGAATGTGACGTTGAAGACGCAACCCTGACACCTTATAAGGA |
| GCGACTGCTGGTCAAAAAATACGCGGGCTCTTGCTAAGGTGAGCCGTTGCTAAAATGTACGTTGAAGCGTTACCTGTTAGGTAACGTAGTTGAG |
| CTGTACATTTTATTTTAAAAAAAATAGTTGAGCTGTCACAGAATGTGACGTTGAAGTTTTTTTTTTTTTTTTCTTGTACATGTGTGTTT |
| TTTTTTTTTTTTTTTTATCACAACAGGCGTTTTTTTTTTTTTTTTTTTACGTTGAAGCGTTACCTGTTAGGTAACGTAGTTGAGCTGTAAA |
| AAAAATTTTAAAAAAAATAGTTGAGCTGTCACAGAATGTGACGTTGAAGTTTTTTTTTTTTTTTTTATTGCAGTATAAATTTTTTTTTT |
| TTTTTTTTTATAGGCCAACAGGATTTTTTTTTTTTTTTTACGTTGAAGCGTTACCTGTTAGGTAACGTAGTTGAGCTGTAAAAAAAATT |
| TTTAATCGGTGTAGTTGAGCTGTCACAGAATGTGACGTTGAAGCACCGATTCCTAAATGGAATGAGTGTAGAACGTGCTGCCTGCTCACCAACG |
| GCATTCTGCCGACATGGTGAGTAAGTTTGGAACGTTGAAGCGTTACCTGTTAGGTAACGTAGTTGAGCTGTTCCAAACTTTTTTGTCGAAATTA |
| GTTGAGCTGTCACAGAATGTGACGTTGAAGATTTC |

Pointer part 1 (FIG. 7B):

SEQ ID NO: 31 atgagtattcaacatttccgtgtcgcccttattccttttttgcggcattttgccttcctgttttttgctcacccagaaacgctggtgaaagtaa aagatgctgaagatcagttgggtgcacgagtgggttacatcgaactggatctcaacagcggtaagatccttgagagttttcgccccgaagaacg ttttccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgccataa ccatgagtgataacactgcggccaacttacttctgacaacgatcggaggaccgaaggagctaaccgcttttttgcacaacatgggggatcatgt aactcgccttgatcgttgggaaccggagctgaatgaagccataccaaacgacgagcgtgacaccacgatgcctgtagcaatggcaacaacgttg cgcaaactattaactggcgaactacttactctagcttcccggcaacaattaatagactggatggaggcggataaagttgcaggaccacttctgc gctcggcccttccggctggctggtttattgctgataaatctggagccggtgagcgtgggtctcgcggtatcattgcagcactggggccagatgg taagccctcccgtatcgtagttatctacacgacggggagtcaggcaactatggatgaacgaaatagacagatcgctgagataggtgcctcactg

| Phagemid sequences |
|---|
| attaagcattggtaactgtcagaccaagtttactcatatatactttagattgatttaaaacttcattttaatttaaaaggatctaggtgaaga |
| tccttttgataatctcatgaccaaaatcccttaacgtgagttttcgttccactgagcgtcagaccccgtagaaaagatcaaaggatcttcttg |
| agatcctttttttctgcgcgtaatctgctgcttgcaaacaaaaaaaccaccgctaccagcggtggtttgtttgccggatcaagagctaccaact |
| ctttttccgaaggtaactggcttcagcagagcgcagataccaaatactgtccttctagtgtagccgtagttaggccaccacttcaagaactctg |
| tagcaccgcctacatacctcgctctgctaatcctgttaccagtggctgctgccagtggcgataagtcgtgtcttaccgggttggactcaagacg |
| atagttaccggataaggcgcagcggtcgggctgaacggggggttcgtgcacacagcccagcttggagcgaacgacctacaccgaactgagatac |
| ctacagcgtgagctatgagaaagcgccacgcttcccgaagggagaaaggcggacaggtatccggtaagcggcagggtcggaacaggagagcgca |
| cgagggagcttccaggggaaacgcctggtatctttatagtcctgtcgggtttcgccacctctgacttgagcgtcgatttttgtgatgctcgtc |
| aggggggcggagcctatggaaaaacgccagcaacgcggcctttttacggttcctggccttttgctggccttttgctcacTGCCCTTTGTAGTTG |
| AGCTGTCACAGAATGTGACGTTGAAGCAAAGGGCGGGTGCCTCGCTCACTGCTTAATGTTGCATGCGGTCACGTTGACGTTGAAGCGTTACCTG |
| TTAGGTAACGTAGTTGAGCTGTCAACGTGATTTTTACAACAATTAGTTGAGCTGTCACAGAATGTGACGTTGAAGATTGTTGTTCCGGCCAACC |
| AGGGTGGTGCCAAGCGACAGGAAGCCGGAACGTTGAAGCGTTACCTGTTAGGTAACGTAGTTGAGCTGTTCCGGCTTTTTTTAAAAAAAATAGT |
| TGAGCTGTCACAGAATGTGACGTTGAAGTTTTTTTTTGGGTGAGACGGGCGAGTTTTTTTTTAAAGGGTCGTGCCGAGGATCCCCGGGTTTT |
| TACGTTGAAGCGTTACCTGTTAGGTAACGTAGTTGAGCTGTAAAAACCCTTTTTCGATTTCGTAGTTGAGCTGTCACAGAATGTGACGTTGAAG |
| CGAAATCGCCTGGCCCTTGCCCCAGAGTAAAATAACATCACTTACGTTGAAGCGTTACCTGTTAGGTAACGTAGTTGAGCTGTAAGTGATGTTT |
| TTCTGATTTTTAGTTGAGCTGTCACAGAATGTGACGTTGAAGAAAATCAGCCCCCGGCAGGCGAAAATCCTGACGCTGGTTGAGAGAGGGACGT |
| TGAAGCGTTACCTGTTAGGTAACGTAGTTGAGCTGTCCCTCTCTTTTTTTTACGGCCTAGTTGAGCTGTCACAGAATGTGACGTTGAAGGGCCG |
| TAAAGCACTAAATTTTTTTTTTCGGAACCGGAAAGCCGGCGATTTTTACGTTGAAGCGTTACCTGTTAGGTAACGTAGTTGAGCTGTAAAAAT |
| CGTTTTTGCTAAAAATAGTTGAGCTGTCACAGAATGTGACGTTGAAGTTTTTAGCGGTCCTTTTTTTTTTTTGATGGTGGTTCAATAGCCCTT |
| GGGCACGTTGAAGCGTTACCTGTTAGGTAACGTAGTTGAGCTGTGCCCAAGGTTTTTCGTAAAAATAGTTGAGCTGTCACAGAATGTGACGTTG |
| AAGTTTTTACGTGGCAACAGCTGAGAAGTTTTCCTTTTTTTTTTCAGTCACGACGTTGTACGTTGAAGCGTTACCTGTTAGGTAACGTAGTTGA |
| GCTGTACAACGTCTTTTTCCCGCGCGTAGTTGAGCTGTCACAGAATGTGACGTTGAAGCGCGCGGGGACGTGCTTCGCCGCTACAGCTTTCAAT |
| AGGAATTGCGGACGTTGAAGCGTTACCTGTTAGGTAACGTAGTTGAGCTGTCCGCAATTTTTTTAAAACCGCTAGTTGAGCTGTCACAGAATGT |
| GACGTTGAAGGCGGTTTTTTTTTTTTGCGTAGAGTTTTTTTTTATAGGGTTGAGTAAAGAACTTACGTTGAAGCGTTACCTGTTAGGTAACG |
| TAGTTGAGCTGTAAGTTCTTTTTTTCTTAGGTTTAGTTGAGCTGTCACAGAATGTGACGTTGAAGAACCTAAGGGTTTTTTTTTAAGAAAGCG |
| AAAGGTCACGCTAGCTCTTTTTTTTTGAATTCGTAATACGTTGAAGCGTTACCTGTTAGGTAACGTAGTTGAGCTGTATTACGAATTTTTATT |
| CAACGTAGTTGAGCTGTCACAGAATGTGACGTTGAAGCGTTGAATGAGTGTAAAGTGTAATTGTTAAGGAAGATGATAATCATGACGTTGAAGC |
| GTTACCTGTTAGGTAACGTAGTTGAGCTGTCATGATTATTTTTGGCGGGTTTAGTTGAGCTGTCACAGAATGTGACGTTGAAGAACCCGCCGCG |
| CCCGCTTTAATGAATCAGTTTGGCCTTATAAATCAAAACGTTGAAGCGTTACCTGTTAGGTAACGTAGTTGAGCTGTTTTGATTTTTTTGAGT |
| TAAATAGTTGAGCTGTCACAGAATGTGACGTTGAAGTTTAACTCGCGTCTTTTTTTTTTGAAATGGATCACCATCAACTGTTTTTTTTTATA |
| GCAAACATACGTTGAAGCGTTACCTGTTAGGTAACGTAGTTGAGCTGTATGTTTGCTTTTTACGTTTTGTAGTTGAGCTGTCACAGAATGTGAC |
| GTTGAAGCAAAACGTTAAAACTAGCTTGAGAGATCTGGAGCTCATTGAATCCCCCTCGAATCGACGTTGAAGCGTTACCTGTTAGGTAACGTAG |
| TTGAGCTGTCGATTCGATTTTTCTTAGAGTTAGTTGAGCTGTCACAGAATGTGACGTTGAAGACTCTAAGCTGCATTCCAGTCGCGTGAACCGT |
| CTATCAGGGCGATGTTTTTTTTTGCCCACTAGGAACGTTGAAGCGTTACCTGTTAGGTAACGTAGTTGAGCTGTTCCTAGTGTTTTTGTAAAA |
| AATAGTTGAGCTGTCACAGAATGTGACGTTGAAGTTTTTTACCGGCGCGTAAACAACCCGAAATTTTTAAAAATTCTGAGTACGTTGAAGCGT |
| TACCTGTTAGGTAACGTAGTTGAGCTGTACTCAGAATTTTTCTACACTGTAGTTGAGCTGTCACAGAATGTGACGTTGAAGCAGTGTAGCGGAG |
| CGGGCGCTAGGGCGAAAAACCAACAAGAGTCCACTACGTTGAAGCGTTACCTGTTAGGTAACGTAGTTGAGCTGTAGTGGACTTTTTTGATAAA |
| ATTAGTTGAGCTGTCACAGAATGTGACGTTGAAGATTTTATCCTCGTTCGTGCATCTGGTGTAGCACCAGCACTCAGAGCAAACGTTGAAGCGT |

| Phagemid sequences |
|---|
| TACCTGTTAGGTAACGTAGTTGAGCTGTTTGCTCTGTTTTTGTTAAAAATAGTTGAGCTGTCACAGAATGTGACGTTGAAGTTTTTAACCAGAG |
| GAATTTTTTTTTAAACGCTCCATCACCTCATTAGACGTTGAAGCGTTACCTGTTAGGTAACGTAGTTGAGCTGTCTAATGAGTTTTTCTTCTA |
| CTTAGTTGAGCTGTCACAGAATGTGACGTTGAAGAGTAGAAGGTTGGGTAACGCCTTTTTTTTTAGGGTGTTTTTATCCAACGTTGAAGCGTT |
| ACCTGTTAGGTAACGTAGTTGAGCTGTTGGATAAATTTTTATCAAAGATAGTTGAGCTGTCACAGAATGTGACGTTGAAGTCTTTGATTAGTAA |
| GAGTCTGTGGGCGATCCCAGGCAACAATAACCCAACGTTGAAGCGTTACCTGTTAGGTAACGTAGTTGAGCTGTTGGGTTATTTTTTGCTGCCA |
| GTAGTTGAGCTGTCACAGAATGTGACGTTGAAGCTGGCAGCTTTCGCGCGAGCAACACCGCTCCTGATTTAGAACCTGAACGTTGAAGCGTTAC |
| CTGTTAGGTAACGTAGTTGAGCTGTTCAGGTTCTTTTTTTCGTAATTAGTTGAGCTGTCACAGAATGTGACGTTGAAGATTACGAATCAGTGCA |
| GAATCCTGATTGCCTTCACCAGGTCGAGGTATCACCCAAATCAAGTTTTTTACGTTGAAGCGTTACCTGTTAGGTAACGTAGTTGAGCTGTAAA |
| AAACTTTTTTGCAAAAATAGTTGAGCTGTCACAGAATGTGACGTTGAAGTTTTTGCAACGCTAGTTTGACATATCTTTTTTTTTTGGTCAGT |
| TGGCACCGACGTTGAAGCGTTACCTGTTAGGTAACGTAGTTGAGCTGTCGGTGCCATTTTTATTAATCGTAGTTGAGCTGTCACAGAATGTGAC |
| GTTGAAGCGATTAATAGCTCAACTGGAAGTCTTTTGATCTATTATACCATCCTAGTCCTGACGTTGAAGCGTTACCTGTTAGGTAACGTAGTTG |
| AGCTGTCAGGACTATTTTTATTACCAGTAGTTGAGCTGTCACAGAATGTGACGTTGAAGCTGGTAATATCCGAATTGAGCCAATTCTAGGTCAG |
| GAAAAGATGCACGTTGAAGCGTTACCTGTTAGGTAACGTAGTTGAGCTGTGCATCTTTTTTTTCGGCCGATTAGTTGAGCTGTCACAGAATGT |
| GACGTTGAAGATCGGCCGGCGGATTCAGTATTGGCAAAGAGATGATGATTAACAATAAACGTTGAAGCGTTACCTGTTAGGTAACGTAGTTGAG |
| CTGTTTATTGTTTTTTTCCAGAAGTTAGTTGAGCTGTCACAGAATGTGACGTTGAAGACTTCTGGTCGGTACGCAGGCCACCATTTAGAGCTTG |
| ACGGCTAAAGACGTTGAAGCGTTACCTGTTAGGTAACGTAGTTGAGCTGTCTTTAGCCTTTTTAGAACTGGTAGTTGAGCTGTCACAGAATGTG |
| ACGTTGAAGCCAGTTCTGAGAGCTGTTTAGCATTGCATCATTAGAGAAAACGTTGAAGCGTTACCTGTTAGGTAACGTAGTTGAGCTGTTTTCT |
| CTATTTTTCCTTTCGGTAGTTGAGCTGTCACAGAATGTGACGTTGAAGCCGAAAGGGTACGGTGTCATGTTTGCGGATGGCTTAGAGCTTACG |
| TTGAAGCGTTACCTGTTAGGTAACGTAGTTGAGCTGTAAGCTCTATTTTTCGCACCTTTAGTTGAGCTGTCACAGAATGTGACGTTGAAGAAGG |
| TGCGGGGTTGATTCGAAGGTTACTTTAGGAGCACTAACGTTTTAACGTTGAAGCGTTACCTGTTAGGTAACGTAGTTGAGCTGTTAAAACGTTT |
| TTTCCTCCTAATAGTTGAGCTGTCACAGAATGTGACGTTGAAGTTAGGAGGCCCAAATTAACCGTTTTTTTTTTTGCAGCCATTTTTTTACGT |
| TGAAGCGTTACCTGTTAGGTAACGTAGTTGAGCTGTAAAAAAATTTTTTATCACATTTAGTTGAGCTGTCACAGAATGTGACGTTGAAGAATGT |
| GATGGGATACTGCAGGTACGGCCAGTTTTTCTTCTTCACCGGCACGTTGAAGCGTTACCTGTTAGGTAACGTAGTTGAGCTGTGCCGGTGATTT |
| TTTTATGTTGTAGTTGAGCTGTCACAGAATGTGACGTTGAAGCAACATAATAAAGCGAAGATAATTGCACGTGATGATGGCATCGGAAGTACGT |
| TGAAGCGTTACCTGTTAGGTAACGTAGTTGAGCTGTACTTCCGATTTTTCGCCCTGGTAGTTGAGCTGTCACAGAATGTGACGTTGAAGCCAGG |
| GCGCCGGAAGCAAGCTAACTTTTTTTTTTTCACATTAAGTGTTTTTTTTTGACTCCAACGTACGTTGAAGCGTTACCTGTTAGGTAACGTAGT |
| TGAGCTGTACGTTGGATTTTTTGAAAAAATAGTTGAGCTGTCACAGAATGTGACGTTGAAGTTTTTTCAATCGTTGTACCAACCTAATTTTTTT |
| TTTAACATCGCCATTAAGATTTTCGAGCGGACGTTGAAGCGTTACCTGTTAGGTAACGTAGTTGAGCTGTCCGCTCGATTTTTATGACCAATAG |
| TTGAGCTGTCACAGAATGTGACGTTGAAGTTGGTCATAGCTGTTTCCTGTGTGAAAAGCCTGTTTTAACCATACGTTGAAGCGTTACCTGTTAG |
| GTAACGTAGTTGAGCTGTATGGTTAATTTTTGCTTATATAGTTGAGCTGTCACAGAATGTGACGTTGAAGTATAAGCAAAAGGGGAAGCCTTT |
| TTTTAATATTTCAATCATATGCGGGACGTTGAAGCGTTACCTGTTAGGTAACGTAGTTGAGCTGTCCCGCATATTTTTATTTGTTAGTTGAG |
| CTGTCACAGAATGTGACGTTGAAGACAAAATAATATACGAGCGTACTATGGTTTTTTTTTTGCTTTTGACGCTTTTTACGTTGAAGCGTTAC |
| CTGTTAGGTAACGTAGTTGAGCTGTAAAAAGCGcattaagcgcggcgggtgtggtggttacgcgcagcgtgaccgctacacttgccagcgccct |
| agcgcccgctcctttcgctttcttcccttcctttctcgccacgttcgccggctttccccgtcaagctctaaatcgggggctcccttagggttc |
| cgatttagtgctttacggcacctcgaccccaaaaaacttgattagggtgatggttcacgtagtgggccatcgccctgatagacggttttcgcc |
| ctttgacgttggagtccacgttctttaatagtggactcttgttccaaactggaacaacactcaaccctatctcggtctattcttttgatttata |
| agggattttgccgatttcggcctattggttaaaaaatgagctgatttaacaaaaatttaacgcgaattttaacaaaatattaacgcttacaatt |
| taggtggcacttttcggggaaatgtgcgcggaaccccctatttgtttattttttctaaatacattcaaatatgtatccgctcatgagacaataacc |
| ctgataaatgcttcaataatattgaaaaaggaagagt |

-continued

| Phagemid sequences |
|---|

Pointer part 2 (FIG. 7B):

SEQ ID NO: 32 atgagtattcaacatttccgtgtcgcccttattccttttttgcggcattttgccttcctgttttgctcacccagaaacgctggtgaaagtaa aagatgctgaagatcagttgggtgcacgagtgggttacatcgaactggatctcaacagcggtaagatccttgagagttttcgccccgaagaacg ttttccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgccataa ccatgagtgataacactgcggccaacttacttctgacaacgatcggaggaccgaaggagctaaccgcttttttgcacaacatgggggatcatgt aactcgccttgatcgttgggaaccggagctgaatgaagccataccaaacgacgagcgtgacaccacgatgcctgtagcaatggcaacaacgttg cgcaaactattaactggcgaactacttactctagcttcccggcaacaattaatagactggatggaggcggataaagttgcaggaccacttctgc gctcggcccttccggctggctggtttattgctgataaatctggagccggtgagcgtgggtctcgcggtatcattgcagcactggggccagatgg taagccctcccgtatcgtagttatctacacgacggggagtcaggcaactatggatgaacgaaatagacagatcgctgagataggtgcctcactg attaagcattggtaactgtcagaccaagtttactcatatatactttagattgatttaaaacttcattttaatttaaaaggatctaggtgaaga tcctttttgataatctcatgaccaaaatcccttaacgtgagttttcgttccactgagcgtcagaccccgtagaaaagatcaaaggatcttcttg agatcctttttttctgcgcgtaatctgctgcttgcaaacaaaaaaaccaccgctaccagcggtggtttgtttgccggatcaagagctaccaact cttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagcttggagcgaacgacctacaccgaactgagatac ctacagcgtgagctatgagaaagcgccacgcttcccgaagggagaaaggcggacaggtatccggtaagcggcagggtcggaacaggagagcgca cgagggagcttccaggggaaacgcctggtatctttatagtcctgtcgggtttcgccacctctgacttgagcgtcgatttttgtgatgctcgtc aggggggcggagcctatggaaaaacgccagcaacgcggcctttttacggttcctggccttttgctggccttttgctcacGGTGATGGTAGTTGA GCTGTCACAGAATGTGACGTTGAAGCCATCACCAAAAACTCCGCTCACAATTCCACACTTTTTTTACGTTGAAGCGTTACCTGTTAGGTAACGT AGTTGAGCTGTAAAAAAAGTTTTTCTGTTGGCTAGTTGAGCTGTCACAGAATGTGACGTTGAAGGCCAACAGATACGTGGTAATGCCGGGGAAG AAGGACGTTGAAGCGTTACCTGTTAGGTAACGTAGTTGAGCTGTCCTTCTTCTTTTTACTAATCGTAGTTGAGCTGTCACAGAATGTGACGTTG AAGCGATTAGTCTTTAATTTTTTTTTTGCGCGAATATGATAACGGAACTGACGAGAAACACCAGTCAATAACGTTGAAGCGTTACCTGTTAGG TAACGTAGTTGAGCTGTTATTGACTTTTTTATAAATAGTAGTTGAGCTGTCACAGAATGTGACGTTGAAGCTATTTATGTCAATCCCTTCTGAA ACAAGAGAATCGATCCTGAGACGTTGAAGCGTTACCTGTTAGGTAACGTAGTTGAGCTGTCTCAGGATTTTTTTGATTTATTAGTTGAGCTGTC ACAGAATGTGACGTTGAAGATAAATCACAGACACCACATTCAACTAATGATACGTTGAAGCGTTACCTGTTAGGTAACGTAGTTGAGCTGTATC ATTAGTTTTTACCAAAAATAGTTGAGCTGTCACAGAATGTGACGTTGAAGTTTTGGTCATTGGAATTTTTTTTTCGGTAATCGTAATATTTT GTGCAATGCTTACGTTGAAGCGTTACCTGTTAGGTAACGTAGTTGAGCTGTAAGCATTGTTTTTTTGTAGATAGTTGAGCTGTCACAGAATGT GACGTTGAAGTCTACAAAAAGAACTGTTGTGAATTACCTTATAGAAATTTTTACGTTGAAGCGTTACCTGTTAGGTAACGTAGTTGAGCTGTAA AAATTTTTTTTTCAAAAATAGTTGAGCTGTCACAGAATGTGACGTTGAAGTTTTTGAATGGCTACCAGTAAATTGGCAGATTCACCATTTTTT TTTTGTCACAACGTTGAAGCGTTACCTGTTAGGTAACGTAGTTGAGCTGTTGTGACAATTTTTTGTTCTATAGTTGAGCTGTCACAGAATGTG ACGTTGAAGTAGAACAATTACATAACAAACAATCATAATAGTACCGACAAAAACGTTGAAGCGTTACCTGTTAGGTAACGTAGTTGAGCTGTTT TTGTCGTTTTTTTCTCATTAGTTGAGCTGTCACAGAATGTGACGTTGAAGATGAGAAAGGTAAATTGAAATCTACAAAAGAAGAGCAACACTA TCATACGTTGAAGCGTTACCTGTTAGGTAACGTAGTTGAGCTGTATGATAGTTTTTTCTCACATATAGTTGAGCTGTCACAGAATGTGACGTTG AAGTATGTGAGTGAAGTTACAAGCCAACGATTTAACATAAATTGTAAACGTTGAAGCGTTACCTGTTAGGTAACGTAGTTGAGCTGTTTACAAT TTTTTTAAATAATTTAGTTGAGCTGTCACAGAATGTGACGTTGAAGAATTATTTTTTTTTAAATTCGCATTTCGGATTCACAGGCAATAGCAT TAGGACGTTGAAGCGTTACCTGTTAGGTAACGTAGTTGAGCTGTCCTAATGCTTTTTATTAAATTTAGTTGAGCTGTCACAGAATGTGACGTTG AAGAATTTAATCAGCTCATTAAATGTTTAATAAATATAAAGGAATACGTTGAAGCGTTACCTGTTAGGTAACGTAGTTGAGCTGTATTCCTTTT

| Phagemid sequences |
|---|
| TTTTTTAAAAAATAGTTGAGCTGTCACAGAATGTGACGTTGAAGTTTTTTAAATCATTCCTTTTTTTTTGTGGGAACAAACTCAGGAAAATAG |
| TAGTGAAAAACGTTGAAGCGTTACCTGTTAGGTAACGTAGTTGAGCTGTTTTTCACTTTTTTCAGGGTACTAGTTGAGCTGTCACAGAATGTGA |
| CGTTGAAGGTACCCTGAAAGAGGTCTAAACCAATTATTTTTTTTTAATCAAGATACGTTGAAGCGTTACCTGTTAGGTAACGTAGTTGAGCTG |
| TATCTTGATTTTTTCTACCATTTAGTTGAGCTGTCACAGAATGTGACGTTGAAGAATGGTAGCGCCATATCGTAACAGAATGAGCACGTATAAG |
| ACGTTGAAGCGTTACCTGTTAGGTAACGTAGTTGAGCTGTCTTATACGTTTTAAGTCTATTAGTTGAGCTGTCACAGAATGTGACGTTGAAGA |
| TAGACTTCAACCAGACCACCGCGCCTCCGGTATCTAACGAGCGTCTACGTTGAAGCGTTACCTGTTAGGTAACGTAGTTGAGCTGTAGACGCTC |
| TTTTTTCATGTTGTAGTTGAGCTGTCACAGAATGTGACGTTGAAGCAACATGAGGCGGTGACCGTAAGCGAGTACCACCAACGTTGAAGCGTTA |
| CCTGTTAGGTAACGTAGTTGAGCTGTTGGTGGTATTTTTATCTGCTGTAGTTGAGCTGTCACAGAATGTGACGTTGAAGCAGCAGATTATCAAA |
| AACAGATAGGCAGATTATACAAGACCTAAACTATATGTATCAATAGACGTTGAAGCGTTACCTGTTAGGTAACGTAGTTGAGCTGTCTATTGAT |
| TTTTTAATATTTGTAGTTGAGCTGTCACAGAATGTGACGTTGAAGCAAATATTTTTTTTTTTCAAACCCTCAATCATGCTGAACACCAGAAG |
| AGGTTTAAATACGTTGAAGCGTTACCTGTTAGGTAACGTAGTTGAGCTGTATTTAAACTTTTTTTCTCTTTTAGTTGAGCTGTCACAGAATGTG |
| ACGTTGAAGAAAGAGAACAATGTTGGGAACCATCACGGATTAAAGTTGCAGCATTTTTACGTTGAAGCGTTACCTGTTAGGTAACGTAGTTGAG |
| CTGTAAAATGCTTTTAAAAAAATTAGTTGAGCTGTCACAGAATGTGACGTTGAAGATTTTTTTTTTTTAAATATGCTTTTTTTTTAACTA |
| AAGGGATTTTTTTTTTGTGCTGCAAGACGTTGAAGCGTTACCTGTTAGGTAACGTAGTTGAGCTGTCTTGCAGCTTTTTAAGAGCAATAGTTG |
| AGCTGTCACAGAATGTGACGTTGAAGTTGCTCTTCATTCCCATTTGGGCGGCACCGCGACGACAGTAAAACGCGACGTTGAAGCGTTACCTGTT |
| AGGTAACGTAGTTGAGCTGTCGCGTTTTTTTTTCTATTGATAGTTGAGCTGTCACAGAATGTGACGTTGAAGTCAATAGATAATAAAGGCTTA |
| CAATAGCAGCGAATAAACAGCTTGATAATAAGTAACGTTGAAGCGTTACCTGTTAGGTAACGTAGTTGAGCTGTTACTTATTTTTTTGACTCAA |
| ATAGTTGAGCTGTCACAGAATGTGACGTTGAAGTTTGAGTCGAGCTTCAAAGCGAAATATCGCCTGAGGCTACTAAAGAAGACGTTGAAGCGTT |
| ACCTGTTAGGTAACGTAGTTGAGCTGTCTTCTTTATTTTTAAAAAGTTTAGTTGAGCTGTCACAGAATGTGACGTTGAAGAACTTTTTTTTTA |
| ATTCGACAACTTTTAAAACATCGCACGTTGAAGCGTTACCTGTTAGGTAACGTAGTTGAGCTGTGCGATGTTTTTTGCTTTGATTAGTTGAGC |
| TGTCACAGAATGTGACGTTGAAGATCAAAGCGGTATATTTTATATAACACCTCTTCGCTATCGGCCTTGCCTACGTTGAAGCGTTACCTGTTAG |
| GTAACGTAGTTGAGCTGTAGGCAAGGTTTTTTCAAAGTTTAGTTGAGCTGTCACAGAATGTGACGTTGAAGAACTTTGAGGTGCAGGGATTTCT |
| TAATAATTTTTAAAGTCAGATTTATACGTTGAAGCGTTACCTGTTAGGTAACGTAGTTGAGCTGTATAAATCTTTTTTTTAAAAATAGTTGAG |
| CTGTCACAGAATGTGACGTTGAAGTTTTTAAAATCAGGTCTTTGGCATCATTTTTTTTTATTCTACTGATTTTTTTTTTCGCACTCCAACGT |
| TGAAGCGTTACCTGTTAGGTAACGTAGTTGAGCTGTTGGAGTGCTTTTTGTTTCGGGTAGTTGAGCTGTCACAGAATGTGACGTTGAAGCCCGA |
| AACATTTCGGTAGATTTGCGCAACTATTACCGCTAGCAATACTACGTTGAAGCGTTACCTGTTAGGTAACGTAGTTGAGCTGTAGTATTGCTTT |
| TTAACGTTCGTAGTTGAGCTGTCACAGAATGTGACGTTGAAGCGAACGTTATTAATCGTATTATAAACAACTGAATTTTGTCGTCTTTCCAGAC |
| GACGTTGAAGCGTTACCTGTTAGGTAACGTAGTTGAGCTGTCGTCTGGATTTTTAAAAAAAATAGTTGAGCTGTCACAGAATGTGACGTTGAAG |
| TTTTTTTTTTTTGAGTAACATTTACCTTTTGAGGCGACGTTGAAGCGTTACCTGTTAGGTAACGTAGTTGAGCTGTCGCCTCAATTTTTCCGA |
| ATAATAGTTGAGCTGTCACAGAATGTGACGTTGAAGTTATTCGGAAACAGTTAGATTAAGACGCTGTTTATATAATTTAATGGGGACGTTGAAGC |
| GTTACCTGTTAGGTAACGTAGTTGAGCTGTCCCCATTATTTTTACACCCTTTAGTTGAGCTGTCACAGAATGTGACGTTGAAGAAGGGTGTTTG |
| GATATAGATAAATTTACGAGCATGTTTTTTTTTTAGAAACCAATCAACGGGTATACGTTGAAGCGTTACCTGTTAGGTAACGTAGTTGAGCTG |
| TATACCCGTTTTTTTGGATATGTAGTTGAGCTGTCACAGAATGTGACGTTGAAGCATATCCAAAAGAAATTAGCAACGCAAGGAGTTAAATCTA |
| AATTACGTTGAAGCGTTACCTGTTAGGTAACGTAGTTGAGCTGTAATTTAGATTTTAAAATGATTAGTTGAGCTGTCACAGAATGTGACGTTG |
| AAGATCATTTTTTTCCATTACGCATAACGACAATGTAGAAAGGAGACGTTGAAGCGTTACCTGTTAGGTAACGTAGTTGAGCTGTCTCCTTTCT |
| TTTTAAAAATGTTAGTTGAGCTGTCACAGAATGTGACGTTGAAGACATTTTTTTTTTCGGGAGAAACTCATTACCGTAATCTTGACAAGAACT |
| GACCTTGTACAGACGTTGAAGCGTTACCTGTTAGGTAACGTAGTTGAGCTGTCTGTACAATTTTTATCTCAAGTAGTTGAGCTGTCACAGAATG |
| TGACGTTGAAGCTTGAGATGGTTTAAATTACCTTATTTCAAAATTAAGCTAACGTTGAAGCGTTACCTGTTAGGTAACGTAGTTGAGCTGTTAG |
| CTTAATTTTTCGTAAAAATAGTTGAGCTGTCACAGAATGTGACGTTGAAGTTTTTACGAGACAAAATTCCTCATATTTTTTTTTTTATTTTAAC |

| Phagemid sequences |
| --- |

GTTGAAGCGTTACCTGTTAGGTAACGTAGTTGAGCTGTTAAAATAATTTTTCTCGTTTTTAGTTGAGCTGTCACAGAATGTGACGTTGAAGAAA

ACGAGTAGCCGGAGAGTTCTAGCGAAAAGCCTAAAAGGGACATTCTACGTTGAAGCGTTACCTGTTAGGTAACGTAGTTGAGCTGTAGAATGTC attaagcgcggcgggtgtggtggttacgcgcagcgtgaccgctacacttgccagcgccctagcgcccgctcctttcgctttcttcccttccttt ctcgccacgttcgccggctttccccgtcaagctctaaatcggggctccctttagggttccgatttagtgctttacggcacctcgaccccaaaa aacttgattagggtgatggttcacgtagtgggccatcgccctgatagacggttttcgcccttttgacgttggagtccacgttctttaatagtgg actcttgttccaaactggaacaacactcaaccctatctcggtctattcttttgatttataagggattttgccgatttcggcctattggttaaaa aatgagctgatttaacaaaaatttaacgcgaattttaacaaaatattaacgcttacaatttaggtggcacttttcggggaaatgtgcgcggaac ccctatttgtttattttctaaatacattcaaatatgtatccgctcatgagacaataaccctgataaatgcttcaataatattgaaaaggaag agt Pointer part 3 (FIG. 7B): SEQ ID NO: 33 atgagtattcaacatttccgtgtcgcccttattccctttttttgcggcattttgccttcctgttttttgctcacccagaaacgctggtgaaagtaa aagatgctgaagatcagttgggtgcacgagtgggttacatcgaactggatctcaacagcggtaagatccttgagagttttcgccccgaagaacg ttttccaatgatgagcacttttaaagttctgctatgtggcgcggtattatcccgtattgacgccgggcaagagcaactcggtcgccgcatacac tattctcagaatgacttggttgagtactcaccagtcacagaaaagcatcttacggatggcatgacagtaagagaattatgcagtgctgccataa ccatgagtgataacactgcggccaacttacttctgacaacgatcggaggaccgaaggagctaaccgcttttttgcacaacatgggggatcatgt aactcgccttgatcgttgggaaccggagctgaatgaagccataccaaacgacgagcgtgacaccacgatgcctgtagcaatggcaacaacgttg cgcaaactattaactggcgaactacttactctagcttcccggcaacaattaatagactggatggaggcggataaagttgcaggaccacttctgc gctcggcccttccggctggctggtttattgctgataaatctggagccggtgagcgtgggtctcgcggtatcattgcagcactggggccagatgg taagccctcccgtatcgtagttatctacacgacggggagtcaggcaactatggatgaacgaaatagacagatcgctgagataggtgcctcactg attaagcattggtaactgtcagaccaagtttactcatatatactttagattgatttaaaacttcattttaatttaaaaggatctaggtgaaga tcctttttgataatctcatgaccaaaatcccttaacgtgagttttcgttccactgagcgtcagacccgtagaaaagatcaaaggatcttcttg agatcctttttttctgcgcgtaatctgctgcttgcaaacaaaaaaaccaccgctaccagcggtggtttgtttgccggatcaagagctaccaact ctttttccgaaggtaactggcttcagcagagcgcagataccaaatactgtccttctagtgtagccgtagttaggccaccacttcaagaactctg tagcaccgcctacatacctcgctctgctaatcctgttaccagtggctgctgccagtggcgataagtcgtgtcttaccgggttggactcaagacg atagttaccggataaggcgcagcggtcgggctgaacggggggttcgtgcacacagcccagcttggagcgaacgacctacaccgaactgagatac ctacagcgtgagctatgagaaagcgccacgcttcccgaagggagaaaggcggacaggtatccggtaagcggcagggtcggaacaggagagcgca cgagggagcttccaggggaaacgcctggtatctttatagtcctgtcgggtttcgccacctctgacttgagcgtcgatttttgtgatgctcgtc aggggggcggagcctatggaaaaacgccagcaacgcggcctttttacggttcctggccttttgctggccttttgctcacGGGTCATATAGTTGA GCTGTCACAGAATGTGACGTTGAAGTATGACCCTGAAATCGGTCTGGCCTTACCTACATTTGACGAGAGCGGGAGCTATTTTTACGTTGAAGCG TTACCTGTTAGGTAACGTAGTTGAGCTGTAAAAATAGTTTTTGAAGGTTATAGTTGAGCTGTCACAGAATGTGACGTTGAAGTAACCTTCCCTT AGAATCCTTGCCAATCGCATATTTTAAGTACCACGTTGAAGCGTTACCTGTTAGGTAACGTAGTTGAGCTGTGGTACTTATTTTGGACGATTT AGTTGAGCTGTCACAGAATGTGACGTTGAAGAATCGTCCGGATATAATAACGGACTGACCAGACGGTCAGTTACTACGTTGAAGCGTTACCTGT TAGGTAACGTAGTTGAGCTGTAGTAACTGTTTTAAAAATTGTAGTTGAGCTGTCACAGAATGTGACGTTGAAGCAATTTTTTTTTATCAACG TAACAAAGCTGCTCATTCAGTAACGTTGAAGCGTTACCTGTTAGGTAACGTAGTTGAGCTGTTACTGAATTTTTGTTTAAAGTAGTTGAGCTG TCACAGAATGTGACGTTGAAGCTTTAAACTTTTTTTTTAGTTCGCGATTTTGGCTATCATTTTTACGTTGAAGCGTTACCTGTTAGGTAACGT AGTTGAGCTGTAAAAATGATTTTTGTTGGCGTTAGTTGAGCTGTCACAGAATGTGACGTTGAAGACGCCAACCTGAAAGCGTAAGAAGATAGAA CATATGTACCCCGGTTTGACGTTGAAGCGTTACCTGTTAGGTAACGTAGTTGAGCTGTCAAACCGGTTTTTCCTAAAAATAGTTGAGCTGTCAC AGAATGTGACGTTGAAGTTTTTAGGTAGAAAGATTCATCAGTACCAGACGACGATTTTTTTTTTAAAAACACGTTGAAGCGTTACCTGTTAGG

| Phagemid sequences |
|---|
| TAACGTAGTTGAGCTGTGTTTTTAATTTTTCTATTTTGTAGTTGAGCTGTCACAGAATGTGACGTTGAAGCAAAATAGCGAGAGGCTTTTGCGT |
| TAATAATAGGAATAATAACGTTGAAGCGTTACCTGTTAGGTAACGTAGTTGAGCTGTTATTATTCTTTTTCCAGTCGATAGTTGAGCTGTCACA |
| GAATGTGACGTTGAAGTCGACTGGATAGCGTCCATTTTTTTTTATACTGCGAAATGACGTTGAAGCGTTACCTGTTAGGTAACGTAGTTGAGC |
| TGTCATTTCGCTTTTTGCCTCGTATAGTTGAGCTGTCACAGAATGTGACGTTGAAGTACGAGGCCAGATACAAGGACGTTGAGAGGGTTAAAGA |
| TTCAAATATTAGCTCATTGCTGGCACGTTGAAGCGTTACCTGTTAGGTAACGTAGTTGAGCTGTGCCAGCAATTTTTAAAACTTATAGTTGAGC |
| TGTCACAGAATGTGACGTTGAAGTAAGTTTTGCCAGAGGGGTAATAGTAATACCAGTCTAACGTTGAAGCGTTACCTGTTAGGTAACGTAGTT |
| GAGCTGTTAGACTGGTTTTTCGAGGGTTTAGTTGAGCTGTCACAGAATGTGACGTTGAAGAACCCTCGTTTTGAGATTAACGAACTATTCAACC |
| CAGTCAAATTATTTACGTTGAAGCGTTACCTGTTAGGTAACGTAGTTGAGCTGTAAATAATTTTTTTTGATAAATAGTTGAGCTGTCACAGAA |
| TGTGACGTTGAAGTTTATCAAAATCATAGGTCTTTTTTTTTTGAGAGACTACCTATAAGGACGTTGAAGCGTTACCTGTTAGGTAACGTAGTT |
| GAGCTGTCCTTATAGTTTTTTACTAAAATAGTTGAGCTGTCACAGAATGTGACGTTGAAGTTTTAGTATTACCTGAGAAAATTATAACAGAGGG |
| TGCCACGTGAGGGACGTTGAAGCGTTACCTGTTAGGTAACGTAGTTGAGCTGTCCCTCACGTTTTTGTATGTTTAGTTGAGCTGTCACAGAAT |
| GTGACGTTGAAGAACATACAGTATAAAATCGCGAATTGCGTAAAATACCATCTAAAGATGGAAATTCGCCAACGTTGAAGCGTTACCTGTTAG |
| GTAACGTAGTTGAGCTGTTGGCGAATTTTTTCAAAATTATAGTTGAGCTGTCACAGAATGTGACGTTGAAGTAATTTTGCTTCTGTGAATAAGG |
| CTTGCCCAACATTATTACTTTTTACGTTGAAGCGTTACCTGTTAGGTAACGTAGTTGAGCTGTAAAAAGTATTTTTATCGCGTTTAGTTGAGCT |
| GTCACAGAATGTGACGTTGAAGAACGCGATAGGCTGGCGCTATTAGGAACCGAATTCGCCTGAATATACAGTAACACGTTGAAGCGTTACCTGT |
| TAGGTAACGTAGTTGAGCTGTGTTACTGTTTTTTGCGTTCGTAGTTGAGCTGTCACAGAATGTGACGTTGAAGCGAACGCAATAAGTTACCTT |
| TGGGAATTAGAGCCTTAGCGTTTGCCATTTTTACGTTGAAGCGTTACCTGTTAGGTAACGTAGTTGAGCTGTAAAAATGGTTTTTGGCTTTCGT |
| AGTTGAGCTGTCACAGAATGTGACGTTGAAGCGAAAGCCTGCAATAGTGTTCATTTGATTTCAACTGTGTAGGAGACGTTGAAGCGTTACCTGT |
| TAGGTAACGTAGTTGAGCTGTCTCCTACATTTTTATATCAGTTAGTTGAGCTGTCACAGAATGTGACGTTGAAGACTGATATAAGTATATTTTT |
| TTTTTGCCCGGAATAGGTAGGCTGAGTTTTTACGTTGAAGCGTTACCTGTTAGGTAACGTAGTTGAGCTGTAAAAACTCTTTTTTTCTTGATTA |
| GTTGAGCTGTCACAGAATGTGACGTTGAAGATCAAGAAAAATGATTTTTTTTTCCATATGAATAATACATCCAATTTTTACGTTGAAGCGTTA |
| CCTGTTAGGTAACGTAGTTGAGCTGTAAAAATTGTTTTTATTATATTAGTTGAGCTGTCACAGAATGTGACGTTGAAGATATAATACTAGAAT |
| GTGATAATTTTAACCCAAAGACAAAATTTTTTTTGGGACCGACTTGAGTTTTACGTTGAAGCGTTACCTGTTAGGTAACGTAGTTGAGCTG |
| TAAAAACTCTTTTTTTAAAATGTAGTTGAGCTGTCACAGAATGTGACGTTGAAGCATTTTAAAGTACACAGCGATTCCCATGTATACCGAAGCC |
| CTTTTTGAACGTTGAAGCGTTACCTGTTAGGTAACGTAGTTGAGCTGTTCAAAAAGTTTTTATTAATTATAGTTGAGCTGTCACAGAATGTGAC |
| GTTGAAGTAATTAATAAAGACAGAGGCGATAAAGCTTAATACTTCGACGTTGAAGCGTTACCTGTTAGGTAACGTAGTTGAGCTGTCGAAGTAT |
| TTTTTAGATGGCGTAGTTGAGCTGTCACAGAATGTGACGTTGAAGCGCCATCTCAACAGTTTCAAATAAGACAAAAGACACCACGGAATAATA |
| CGTTGAAGCGTTACCTGTTAGGTAACGTAGTTGAGCTGTATTATTCCTTTTTCAAAGTTGTAGTTGAGCTGTCACAGAATGTGACGTTGAAGCA |
| ACTTTGAAAGAGGTTTTTTTTTTACAGATGAACGGTCATCAAGAACGTTGAAGCGTTACCTGTTAGGTAACGTAGTTGAGCTGTTCTTGATGTT |
| TTTTACTTTACTAGTTGAGCTGTCACAGAATGTGACGTTGAAGGTAAAGTAATTCGCTAATGCAGAACGCGCCTTTTTTTTTTGTTTATCAAC |
| ATATACTTCAATCATTTTTACGTTGAAGCGTTACCTGTTAGGTAACGTAGTTGAGCTGTAAAAATGATTTTCTTCGTTATAGTTGAGCTGTCA |
| CAGAATGTGACGTTGAAGTAACGAAGGCACAGCCCTCATAGTTTTTTTTTTAGCCCCACAAGACGTTGAAGCGTTACCTGTTAGGTAACGTA |
| GTTGAGCTGTCTTGTGGGTTTTTTACGTATTTAGTTGAGCTGTCACAGAATGTGACGTTGAAGAATACGTACAAACAGCAAGAAACAATGAACC |
| CTGAACTCACGTTGTAACGTTGAAGCGTTACCTGTTAGGTAACGTAGTTGAGCTGTTACAACGTTTTTCGACTTGCTAGTTGAGCTGTCACAG |
| AATGTGACGTTGAAGGCAAGTCGAAATGAGGTTTAGCGGATAATAGCGGGGAAACGAACGTTGAAGCGTTACCTGTTAGGTAACGTAGTTGA |
| GCTGTTGCGTTTCTTTTAGTTCGTTTAGTTGAGCTGTCACAGAATGTGACGTTGAAGAACGAACTTTTTCAAATTGAGACGTCAGATGATTGC |
| TTTGAATACCAAACGTTGAAGCGTTACCTGTTAGGTAACGTAGTTGAGCTGTTTGGTATTTTTTAACATGTTTAGTTGAGCTGTCACAGAATG |
| TGACGTTGAAGAACATGTTCATGTCCAGACTCATTTTAATAACGGTCACCGTCCGACATTCACGTTGAAGCGTTACCTGTTAGGTAACGTAGTT |
| GAGCTGTGAATGTCGTTTTTACAGGGTGTAGTTGAGCTGTCACAGAATGTGACGTTGAAGCACCCTGTATCGGTAGGCTCCATTAGACGGTGTT |

-continued

| Phagemid sequences |
|---|

TAACGTCAAAAATGACGTTGAAGCGTTACCTGTTAGGTAACGTAGTTGAGCTGTCATTTTTGTTTTTCGGATCCTAGTTGAGCTGTCACAGAA
TGTGACGTTGAAGGGATCCGAGGGTATTGACCCCACGGAGATCCCTCAACGTTGAAGCGTTACCTGTTAGGTAACGTAGTTGAGCTGTTGAGGG
ATTTTTTCTCTTAAATAGTTGAGCTGTCACAGAATGTGACGTTGAAGTTAAGAGGAATATTCCTAATGAAAAGAACGAACATGGGCGCCCTGT
AACGTTGAAGCGTTACCTGTTAGGTAACGTAGTTGAGCTGTTACAGGGCTTTTTATCTATATTAGTTGAGCTGTCACAGAATGTGACGTTGAAG
ATATAGATTTTGCAATCCTTTGATTTAGAAGTATTAGACTTTACATTAGTAACGTTGAAGCGTTACCTGTTAGGTAACGTAGTTGAGCTGTTAC
TAATGTTTTTCCGTTTGGTAGTTGAGCTGTCACAGAATGTGACGTTGAAGCCAAACGGGTAAAATTTTTTTTTTACGTAATGCCACTGCCGGA
ACACGTTGAAGCGTTACCTGTTAGGTAACGTAGTTGAGCTGTGTTCCGGCTTTTTAACTTCACTAGTTGAGCTGTCACAGAATGTGACGTTGAA
GGTGAAGTTAAAGGGAATCATTGGAAGCAAGATTAGAGAATCAACAGTTACGTTGAAGCGTTACCTGTTAGGTAACGTAGTTGAGCTGTAACTG
TTGTTTTTAAGGTACGTAGTTGAGCTGTCACAGAATGTGACGTTGAAGCGTACCTTTTGAAATATTCTAAATATAATGCTGAACTCAAACTACG
TTGAAGCGTTACCTGTTAGGTAACGTAGTTGAGCTGTAGTTTGAGTTTTTTTCAACGGTAGTTGAGCTGTCACAGAATGTGACGTTGAAGCCGT
TGAACCTCCCAGCTACAATTTTATCCGATTTTTGAGAATTAACACGTTGAAGCGTTACCTGTTAGGTAACGTAGTTGAGCTGTGTTAATTCTTT
TTTACGGCTTTAGTTGAGCTGTCACAGAATGTGACGTTGAAGAAGCCGTACCGCATTCCAAGAATAATCGGTAAGCAGATAGCCTTTTTACGTT
GAAGCGTTACCTGTTAGGTAACGTAGTTGAGCTGTAAAAAGGCattaagcgcggcgggtgtggtggttacgcgcagcgtgaccgctacacttgc
cagcgccctagcgcccgctcctttcgctttcttccttcctttctcgccacgttcgccggctttccccgtcaagctctaaatcgggggctccct
ttaggggttccgatttagtgctttacggcacctcgaccccaaaaaacttgattagggtgatggttcacgtagtgggccatcgccctgatagacgg
ttttcgcccttttgacgttggagtccacgttctttaatagtggactcttgttccaaactggaacaacactcaaccctatctcggtctattcttt
tgatttataagggattttgccgatttcggcctattggttaaaaaatgagctgatttaacaaaaatttaacgcgaattttaacaaaatattaacg
cttacaatttaggtggcacttttcggggaaatgtgcgcggaaccccctatttgtttattttttctaaatacattcaaatatgtatccgctcatgag
acaataaccctgataaatgcttcaataatattgaaaaaggaagagt Pointer part 4 (FIG. 7B):

SEQ ID NO: 34 atgagtattcaacatttccgtgtcgcccttattccctttttttgcggcattttgccttcctgttttttgctcacccagaaacgctggtgaaagtaa
aagatgctgaagatcagttgggtgcacgagtgggttacatcgaactggatctcaacagcggtaagatccttgagagttttcgccccgaagaacg
ttttccaatgatgagcacttttaaagttctgctatgtggcgcggtattatcccgtattgacgccgggcaagagcaactcggtcgccgcatacac
tattctcagaatgacttggttgagtactcaccagtcacagaaaagcatcttacggatggcatgacagtaagagaattatgcagtgctgccataa
ccatgagtgataacactgcggccaacttacttctgacaacgatcggaggaccgaaggagctaaccgcttttttgcacaacatgggggatcatgt
aactcgccttgatcgttgggaaccggagctgaatgaagccataccaaacgacgagcgtgacaccacgatgcctgtagcaatggcaacaacgttg
cgcaaactattaactggcgaactacttactctagcttcccggcaacaattaatagactggatggaggcggataaagttgcaggaccacttctgc
gctcggcccttccggctggctggtttattgctgataaatctggagccggtgagcgtgggtctcgcggtatcattgcagcactggggccagatgg
taagccctcccgtatcgtagttatctacacgacggggagtcaggcaactatggatgaacgaaatagacagatcgctgagataggtgcctcactg
attaagcattggtaactgtcagaccaagtttactcatatatactttagattgatttaaaacttcattttttaatttaaaaggatctaggtgaaga
tcctttttgataatctcatgaccaaaatcccttaacgtgagttttcgttccactgagcgtcagaccccgtagaaaagatcaaaggatcttcttg
agatcctttttttctgcgcgtaatctgctgcttgcaaacaaaaaaaccaccgctaccagcggtggtttgtttgccggatcaagagctaccaact
cttttttccgaaggtaactggcttcagcagagcgcagataccaaatactgtccttctagtgtagccgtagttaggccaccacttcaagaactctg
tagcaccgcctacatacctcgctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtcggaacaggagagcgca
cgagggagcttccaggggaaacgcctggtatctttatagtcctgtcgggtttcgccacctctgacttgagcgtcgatttttgtgatgctcgtc
agggggggcggagcctatggaaaaacgccagcaacgcggcctttttacggttcctggccttttgctggccttttgctcacAAATAAAGTAGTTGA

| Phagemid sequences |
| --- |
| GCTGTCACAGAATGTGACGTTGAAGCTTTATTTTCAAAAAAATTATCAGCAGCTATCTCCGTAACACTGAGTACGTTGAAGCGTTACCTGTTAG |
| GTAACGTAGTTGAGCTGTACTCAGTGTTTTTTGAAATTTAGTTGAGCTGTCACAGAATGTGACGTTGAAGAATTTCAACAGTTTCTTTTTTTT |
| TTAGCGGAGTGAGAAACAACAACACGTTGAAGCGTTACCTGTTAGGTAACGTAGTTGAGCTGTGTTGTTGTTTTTGGCTGCTATAGTTGAGCT |
| GTCACAGAATGTGACGTTGAAGTAGCAGCCTTTACAGTTTTTTTTTAGAGAATAACATAACGTTGAAGCGTTACCTGTTAGGTAACGTAGTTG |
| AGCTGTTATGTTATTTTTTGACGTTGGTAGTTGAGCTGTCACAGAATGTGACGTTGAAGCCAACGTCTAAGAACGCGAGGCAACTAATAACTCC |
| AACGCGAACGACAACGTTGAAGCGTTACCTGTTAGGTAACGTAGTTGAGCTGTTGTCGTTCTTTTTATGGCGAATAGTTGAGCTGTCACAGAAT |
| GTGACGTTGAAGTTCGCCATATTAGGGTAATTGAGCGCTTAAGCCCAATACCGATAAACGTTGAAGCGTTACCTGTTAGGTAACGTAGTTGAGC |
| TGTTTATCGGTTTTTTACTATTTTTAGTTGAGCTGTCACAGAATGTGACGTTGAAGAAAATAGTTGCTATCCTTATCACTCATCGAATAATATC |
| GTCAGAAGCAATATAACTACGTTGAAGCGTTACCTGTTAGGTAACGTAGTTGAGCTGTAGTTATATTTTTGGATTGGGTAGTTGAGCTGTCAC |
| AGAATGTGACGTTGAAGCCCAATCCAAATAAGAAACTGAATCTAAAATCTCCATCGTAGCCGCTTACGTTGAAGCGTTACCTGTTAGGTAACGT |
| AGTTGAGCTGTAAGCGGCTTTTTTGCTCTGTGTAGTTGAGCTGTCACAGAATGTGACGTTGAAGCACAGAGCCTAAGGAATTAGCAAATCTTCG |
| GTCGGTTTTAATAAGAAACCCTACGTTGAAGCGTTACCTGTTAGGTAACGTAGTTGAGCTGTAGGGTTTCTTTTTCCTGTTTTTAGTTGAGCTG |
| TCACAGAATGTGACGTTGAAGAAAACAGGAAGAAAAGCTGTCTTTATAAACAACAAGAAAATAATAAGAACACGTTGAAGCGTTACCTGTTAGG |
| TAACGTAGTTGAGCTGTGTTCTTATTTTTCTTTTGCGTAGTTGAGCTGTCACAGAATGTGACGTTGAAGCGCAAAAGGAGCTTTGCACCCGAC |
| TTGCGGGAGGTTTTAATTGCAAACGTTGAAGCGTTACCTGTTAGGTAACGTAGTTGAGCTGTTTGCAATTTTTTATTGTTCATAGTTGAGCTG |
| TCACAGAATGTGACGTTGAAGTGAACAATAGCAATTTGCTTTCACTCATCTGCAACGGCATACGTTGAAGCGTTACCTGTTAGGTAACGTAGTT |
| GAGCTGTATGCCGTTTTTTTTACTTATTAGTTGAGCTGTCACAGAATGTGACGTTGAAGATAAGTAACTTTTTTTTTGATCTAAAGTTTTAG |
| TTACAAAATAAAACGTTGAAGCGTTACCTGTTAGGTAACGTAGTTGAGCTGTTTATTTTTTTACTCAATTTAGTTGAGCTGTCACAGAATG |
| TGACGTTGAAGAATTGAGTAATATCAGAACAACTAAATTTGCCCTGTATGGAGATATAGCAACGTTGAAGCGTTACCTGTTAGGTAACGTAGTT |
| GAGCTGTTGCTATATTTTTTTCAAAAATAGTTGAGCTGTCACAGAATGTGACGTTGAAGTTTTGAACACAGGGATAGCAAGCCCCCACCACC |
| CGACGACAACCGACACGTTGAAGCGTTACCTGTTAGGTAACGTAGTTGAGCTGTGTCGGTTGTTTTGCGGTTAATAGTTGAGCTGTCACAGAA |
| TGTGACGTTGAAGTTAACCGCCATTGTATCACATCTTCTATTCTTACGCGATAGCTACATAACGTTGAAGCGTTACCTGTTAGGTAACGTAGTT |
| GAGCTGTTATGTAGCTTTTTAGGCGTTGTAGTTGAGCTGTCACAGAATGTGACGTTGAAGCAACGCCTGTAGCAGTACTCAGCCGCGACCGAAA |
| ACTTTAGGGCTTATACGTTGAAGCGTTACCTGTTAGGTAACGTAGTTGAGCTGTATAAGCCCTTTTTAGTCTTATTAGTTGAGCTGTCACAGAA |
| TGTGACGTTGAAGATAAGACTCATAGACGGATATTCATGAGCCGCCGCCAGCATCGCCTCACGTTGAAGCGTTACCTGTTAGGTAACGTAGTTG |
| AGCTGTGAGGCGATTTTTTGTATCATGTAGTTGAGCTGTCACAGAATGTGACGTTGAAGCATGATACCGCCACGCACCATTACCATTAGTTTCA |
| TCGTAAACAGTGTACGTTGAAGCGTTACCTGTTAGGTAACGTAGTTGAGCTGTACACTGTTTTTTGGCGGTACTAGTTGAGCTGTCACAGAAT |
| GTGACGTTGAAGGTACCGCCACCAATGAAACCATCGAAGTTTGCCCTATTACGTTGAAGCGTTACCTGTTAGGTAACGTAGTTGAGCTGTAATA |
| GGGCTTTTTCTCGACGGTAGTTGAGCTGTCACAGAATGTGACGTTGAAGCCGTCGAGAGGGTCAGGCGCATGCTCCATATCATAAGTGAGGAAG |
| GCGGAACAGCCACGTTGAAGCGTTACCTGTTAGGTAACGTAGTTGAGCTGTGGCTGTTCTTTTTAGTAAAAATAGTTGAGCTGTCACAGAATGT |
| GACGTTGAAGTTTTTACTCCTCAATTTTTTTTTTAAGCAGTAGCGACAGAATCATAGCAGCATTAGGATGTACGTTGAAGCGTTACCTGTTA |
| GGTAACGTAGTTGAGCTGTACATCCTATTTTTGGAAAAATAGTTGAGCTGTCACAGAATGTGACGTTGAAGTTTTTCCAAGAAGGAATTTTTT |
| TTTTACCGAGGATTAAATAAGAATTTTTTTTTTAAACACCGACGTTGAAGCGTTACCTGTTAGGTAACGTAGTTGAGCTGTCGGTGTTTTTTT |
| TATTCACATTAGTTGAGCTGTCACAGAATGTGACGTTGAAGATGTGAATTAAATACCCAACCAGCGCTCCGGCTTAGGTTGGGAGAAGAACGTT |
| GAAGCGTTACCTGTTAGGTAACGTAGTTGAGCTGTTCTTCTCCTTTTTCTGAGGTATAGTTGAGCTGTCACAGAATGTGACGTTGAAGTACCTC |
| AGAGAATAGGAAATACCAAGCTTTAATTCAGCAGCGGAACAAACGTTGAAGCGTTACCTGTTAGGTAACGTAGTTGAGCTGTTTGTTCCGTTTT |
| TGGCCTTGATAGTTGAGCTGTCACAGAATGTGACGTTGAAGTCAAGGCCGCGTAGAAACTTATTACTTGTCACAAAATGCTGATGCAAATAAAC |
| GTTGAAGCGTTACCTGTTAGGTAACGTAGTTGAGCTGTTTATTTGCTTTTTAGAAAAAATAGTTGAGCTGTCACAGAATGTGACGTTGAAGTTT |
| TTTCTTTTCATAATCCCTTGATATTTTTTTTTTTCACAAACAAATAACGTTGAAGCGTTACCTGTTAGGTAACGTAGTTGAGCTGTTATTTGT |

```
                              Phagemid sequences

TTTTTTAATAGGCATAGTTGAGCTGTCACAGAATGTGACGTTGAAGTGCCTATTAGCAAAGAAACGTCACCCTCAGCGTCACCAACTAAAACGA

ACGTTGAAGCGTTACCTGTTAGGTAACGTAGTTGAGCTGTTCGTTTTATTTTTACACTCATTAGTTGAGCTGTCACAGAATGTGACGTTGAAGA

TGAGTGTACAGAGCCACTTTTTTTTTTCACCCTCAGAGCCGACGTTGAAGCGTTACCTGTTAGGTAACGTAGTTGAGCTGTCGGCTCTGTTTTT

CTCTACTTTAGTTGAGCTGTCACAGAATGTGACGTTGAAGAAGTAGAGAAGGACCGTAATGTATCACCTTCCACAGACCAACCTAGTTGCGCCC

ACGTTGAAGCGTTACCTGTTAGGTAACGTAGTTGAGCTGTGGGCGCAATTTTTTGACAAGGTAGTTGAGCTGTCACAGAATGTGACGTTGAAGC

CTTGTCAGAGCCGCCACCCTCAGAACCGACCAGAACCCACGTTGAAGCGTTACCTGTTAGGTAACGTAGTTGAGCTGTGGGTTCTGTTTTTAAT

CGTTTTAGTTGAGCTGTCACAGAATGTGACGTTGAAGAAACGATTGGAAAATCACGGTTGAGGAACCGATTGAGGGAGGTATGGTACGTTGAAG

CGTTACCTGTTAGGTAACGTAGTTGAGCTGTACCATACCTTTTTTGCGCTTTTAGTTGAGCTGTCACAGAATGTGACGTTGAAGAAAGCGCAGT

CCGGGGTCATAATGCCCCACCACCAACATAAAGGTGGCAACGTTGAAGCGTTACCTGTTAGGTAACGTAGTTGAGCTGTTGCCACCTTTTTCA

TGTATGTAGTTGAGCTGTCACAGAATGTGACGTTGAAGCATACATGGCTTTTTTTTTTTTGATGATACAGTCTGAAACATGAACGTTGAAGC

GTTACCTGTTAGGTAACGTAGTTGAGCTGTTCATGTTTTTTTGGGTGGGGTAGTTGAGCTGTCACAGAATGTGACGTTGAAGCCCCACCCTCT

GGTAATAAGTTTTAATCTGAATTTCAGACTGTAGCGCACGTTGAAGCGTTACCTGTTAGGTAACGTAGTTGAGCTGTGCGCTACATTTTTCTGA

CCTGTAGTTGAGCTGTCACAGAATGTGACGTTGAAGCAGGTCAGACCGGAACTGACAGGACGGAACCACATTAAAGCACCAGACGTTGAAGCGT

TACCTGTTAGGTAACGTAGTTGAGCTGTCTGGTGCTTTTTTGTTACTGGTAGTTGAGCTGTCACAGAATGTGACGTTGAAGCCAGTAACAGGAG

CCACCTCCTCATTGGTCATAGCCCCCTTAAGCAAAACGTTGAAGCGTTACCTGTTAGGTAACGTAGTTGAGCTGTTTGCTTATTTTTTCTTT

AATAGTTGAGCTGTCACAGAATGTGACGTTGAAGTTAAAGAACTTTTGAAATCGCGAAACCGAGCCAGAAAGACAGCAATTCACGTTGAAGCGT

TACCTGTTAGGTAACGTAGTTGAGCTGTGAATTGCTTTTTTGAATTTTTAGTTGAGCTGTCACAGAATGTGACGTTGAAGAAAATTCAGAAGG

TAAAAATTATTTGCCCGTAGCATTTTCAAAGCCAGAATGACGTTGAAGCGTTACCTGTTAGGTAACGTAGTTGAGCTGTCATTCTGGTTTTTA

AACTGTTAGTTGAGCTGTCACAGAATGTGACGTTGAAGACAGTTTATTGCAGTATGGTTAATTTTCGCCTGAACGCCAACTACAGAGGTTATCA

TCAGACGTTGAAGCGTTACCTGTTAGGTAACGTAGTTGAGCTGTCTGATGATTTTTAATTTTATTAGTTGAGCTGTCACAGAATGTGACGTTG

AAGATAAAATTTTGCTCTTTCGGAACTTTAGCGTACCGTTCCAGTAAGCGTACGTTGAAGCGTTACCTGTTAGGTAACGTAGTTGAGCTGTACG

CTTACattaagcgcggcgggtgtggtggttacgcgcagcgtgaccgctacacttgccagcgccctagcgcccgctcctttcgctttcttccctt cctttctcgccacgttcgccggctttccccgtcaagctctaaatcggggctccctttagggttccgatttagtgctttacggcacctcgaccc caaaaaacttgattagggtgatggttcacgtagtgggccatcgccctgatagacggttttcgcccttttgacgttggagtccacgttctttaat agtggactcttgttccaaactggaacaacactcaaccctatctcggtctattcttttgatttataagggatttgccgatttcggcctattggt taaaaaatgagctgatttaacaaaaatttaacgcgaattttaacaaaatattaacgcttacaatttaggtggcacttttcggggaaatgtgcgc ggaaccctatttgtttattttctaaatacattcaaatatgtatccgctcatgagacaataaccctgataaatgcttcaataatattgaaaaa ggaagagt
```

The features disclosed in the foregoing description, in the claims and/or in the accompanying drawings may, both separately and in any combination thereof, be material for realizing the invention in diverse forms thereof.

REFERENCES

Bai X, Martin T, Scheres S, and Dietz H. Cryo-EM structure of a 3D DNA-origami object. *P Natl Acad Sci USA*, vol 109 (2012), 20012.

Breaker R R. DNA enzymes. *Nat Biotechnol.* 1997; 15(5):427-31.

Carmi N, Shultz L A, Breaker R R. In vitro selection of self-cleaving DNAs. *Chem Biol.* 1996; 3(12):1039-46.

Chandra M, Sachdeva A, Silverman S K. DNA-catalyzed sequence-specific hydrolysis of DNA. *Nat Chem Biol.* 2009; 5(10):718-20. doi: 10.1038/nchembio.201.

Ducani C, Kaul C, Moche M, Shih W M, Hogberg B. Enzymatic production of 'monoclonal stoichiometric' single-stranded DNA oligonucleotides. *Nat Methods.* 2013; 10(7):647-52. doi: 10.1038/nmeth.2503.

Gu H, Furukawa K, Weinberg Z, Berenson D F, Breaker R R Small, highly active DNAs that hydrolyze DNA. *J Am Chem Soc.* 2013; 135(24):9121-9. doi: 10.1021/ja403585e.

Gu H, Breaker R R. Production of single-stranded DNAs by self-cleavage of rolling-circle amplification products. Biotechniques. 2013; 54(6):337-43. doi: 10.2144/000114009.

Jones M R, Seeman N C, Mirkin C A. Nanomaterials. Programmable materials and the nature of the DNA bond. *Science* 2015;347(6224):1260901. doi: 10.1126/science.1260901.

Keefe A D, Pai S, Ellington A. Aptamers as therapeutics. *Nat Rev Drug Discov.* 2010 Jul;9(7):537-50. doi: 10.1038/nrd3141.

Kick B, Praetorius F, Dietz H, Weuster-Botz D. Efficient Production of Single-Stranded Phage DNA as Scaffolds for DNA Origami. *Nano Lett.* 2015; 15(7):4672-6. doi: 10.1021/a cs.nanolett.5b01461.

Krug N, Hohlfeld J M, Kirsten A M, Kornmann O, Beeh K M, Kappeler D, Korn S, Ignatenko S, Timmer W, Rogon C, Zeitvogel J, Zhang N, Bille J, Homburg U, Turowska A, Bachert C, Werfel T, Buhl R, Renz J, Garn H, Renz H. Allergen-induced asthmatic responses modified by a GATA3-specific DNAzyme. *N Engl J Med.* 2015; 372(21):1987-95. doi: 10.1056/NEJ-Moa1411776.

Marchi A N, Saaem I, Vogen B N, Brown S, LaBean T H. Toward larger DNA origami. *Nano Lett.* 2014; 14(10): 5740-7. doi: 10.1021/n1502626s.

Ng E W, Shima D T, Calias P, Cunningham E T Jr, Guyer D R, Adamis A P. Pegaptanib, a targeted anti-VEGF aptamer for ocular vascular disease. *Nat Rev Drug Discov.* 2006; 5(2):123-32.

Rothemund P W. Folding DNA to create nanoscale shapes and patterns. *Nature.* 2006; 440(7082):297-302.

Schmidt T L, Beliveau B J, Uca Y O, Theilmann M, Da Cruz F, Wu C T, Shih W M. Scalable amplification of strand subsets from chip-synthesized oligonucleotide libraries. *Nat Commun.* 2015; 6:8634. doi: 10.1038/ncomms9634.

Sheppard T L, Ordoukhanian P, Joyce G F. A DNA enzyme with N-glycosylase activity. *Proc Natl Acad Sci USA.* 2000; 97(14):7802-7.

Torabi S F, Wu P, McGhee C E, Chen L, Hwang K, Zheng N, Cheng J, Lu Y. In vitro selection of a sodium-specific DNAzyme and its application in intracellular sensing. *Proc Natl Acad Sci USA.* 2015; 112(19):5903-8. doi: 10.1073/pnas.1420361112.

The invention claimed is:

1. A method for the recombinant production of DNA single strand molecules, comprising the steps of:
   (1) providing a pseudogene nucleic acid,
      wherein said pseudogene nucleic acid is a nucleic acid that comprises (i) at least one target DNA oligo- or polynucleotide sequence and (ii) at least one cleavage set of two self-cleaving DNA sequences flanking each target DNA oligo- or polynucleotide sequence, wherein said pseudogene nucleic acid comprises one cleavage set per the one target DNA oligo- or polynucleotide sequence, and two self-cleaving DNA sequences are linked in inverted order to each other to form the one cleavage set;
   (2) integrating the pseudogene nucleic acid into a vector;
   (3) transforming bacterial cells in a bacterial culture with said vector
   (4) producing a precursor ssDNA from said vector under bacterial culture conditions, wherein said precursor ssDNA comprises the pseudogene nucleic acid;
   (5) isolating the precursor ssDNA from the bacterial culture;
   (6) digesting the precursor ssDNA under reaction conditions where the self-cleaving DNA sequences become active and cut off the at least one cleavage set;
   (7) separating the at least one target single stranded DNA oligo- or polynucleotide sequence; and
   (8) obtaining the at least one target single stranded DNA oligo- or polynucleotide sequence.

2. The method of claim 1, wherein the self-cleaving DNA sequences are self-cleaving desoxyribozymes or DNAzymes.

3. The method of claim 2, wherein the self-cleaving DNA sequences are $Zn^{2+}$-dependent DNAzymes.

4. The method of claim 1, wherein the pseudogene nucleic acid comprises two, three, four or more than about 50 target DNA oligonucleotide sequences.

5. The method of claim 1, wherein the at least one target DNA oligo- or polynucleotide sequence has a length in the range from about 20 nucleotides to about eleven thousand nucleotides.

6. The method of claim 1, wherein the bacterial cells are from bacteria selected from K12-derived *E. coli* safety strains.

7. The method of claim 6, wherein the bacterial cells are DH5alpha, XL-1blue or JM109.

8. The method of claim 1, wherein the vector in step (2) is at least one phagemid, comprising
   a packaging sequence,
   component(s) ensuring propagation of the phagemid during cell division,
   a selection marker, and
   an antibiotic resistance gene.

9. The method of claim 8, further comprising a helper plasmid or a helper phage comprising
   genes encoding the proteins of a bacteriophage
   component(s) ensuring propagation of the helper plasmid during cell division,
   a selection marker, and
   an antibiotic resistance gene.

10. The method of claim 1, wherein the vector in step (2) is at least one phagemid and is amplified inside the bacterial cells via rolling circle amplification (RCA) resulting in phagemid ssDNA.

11. The method of claim 10, wherein the phagemid ssDNA is packaged into phage-like particles.

12. The method of claim 11, wherein step (5) comprises extracting the phage-like particles from the bacterial culture and extracting the phagemid ssDNA from the phage-like particles.

13. The method of claim 1, wherein said digestion of step (6) is triggered by the addition of $Zn^{2+}$ ions.

14. The method of claim 1, wherein separating the at least one target single stranded DNA oligo- or polynucleotide sequence in step (7) comprises separating from the cleavage sets of two self-cleaving DNA sequences linked in inverted order to each other.

15. The method of claim 1, comprising the further step of
   (9) self-assembly and/or folding into DNA origami structures, tile-based DNA nanostructures, or crystalline DNA nanomaterials,
   or the use as aptamers or DNAzymes to bind, detect, or process other molecules.

16. The method of claim 1, wherein the bacterial culture is carried out in a stirred-tank bioreactor.

* * * * *